(12) United States Patent
Zharov

(10) Patent No.: US 9,144,383 B2
(45) Date of Patent: Sep. 29, 2015

(54) DEVICE AND METHOD FOR IN VIVO NONINVASIVE MAGNETIC MANIPULATION OF CIRCULATING OBJECTS IN BIOFLOWS

(75) Inventor: Vladimir Pavlovich Zharov, Little Rock, AR (US)

(73) Assignee: The Board of Trustees of the University of Arkansas, Little Rock, AR (US)

(*) Notice: Subject to any disclaimer, the term of this patent is extended or adjusted under 35 U.S.C. 154(b) by 1357 days.

(21) Appl. No.: 12/945,576

(22) Filed: Nov. 12, 2010

(65) Prior Publication Data

US 2011/0117028 A1 May 19, 2011

Related U.S. Application Data

(63) Continuation-in-part of application No. 12/334,217, filed on Dec. 12, 2008, now abandoned.

(60) Provisional application No. 61/013,543, filed on Dec. 13, 2007.

(51) Int. Cl.
| | |
|---|---|
| A61B 8/00 | (2006.01) |
| A61B 6/00 | (2006.01) |
| A61B 5/00 | (2006.01) |
| A61K 49/22 | (2006.01) |
| B03C 1/28 | (2006.01) |
| B03C 1/30 | (2006.01) |
| A61B 8/08 | (2006.01) |
| A61B 18/18 | (2006.01) |

(Continued)

(52) U.S. Cl.
CPC ............ *A61B 5/0059* (2013.01); *A61B 5/0095* (2013.01); *A61B 5/412* (2013.01); *A61B 5/415* (2013.01); *A61B 5/416* (2013.01); *A61B 5/418* (2013.01); *A61B 8/481* (2013.01); *A61K 49/22* (2013.01); *B03C 1/288* (2013.01); *B03C 1/30* (2013.01); *A61B 8/08* (2013.01); *A61B 18/1815* (2013.01); *A61B 18/20* (2013.01); *B03C 2201/06* (2013.01); *B03C 2201/26* (2013.01); *G01N 15/147* (2013.01); *G01N 15/1425* (2013.01); *G01N 15/1434* (2013.01); *G01N 2015/1477* (2013.01)

(58) Field of Classification Search
None
See application file for complete search history.

(56) References Cited

U.S. PATENT DOCUMENTS

| | | | | |
|---|---|---|---|---|
| 4,333,474 | A | | 6/1982 | Nigam |
| 5,972,721 | A | * | 10/1999 | Bruno et al. ................ 436/526 |
| 6,710,871 | B1 | * | 3/2004 | Goix ............................ 356/318 |

(Continued)

FOREIGN PATENT DOCUMENTS

DE          10343442 A1 *   4/2005

OTHER PUBLICATIONS

English abstract of DE 10343442A1.*

(Continued)

*Primary Examiner* — Sanjay Cattungal
*Assistant Examiner* — Bradley Impink
(74) *Attorney, Agent, or Firm* — Polsinelli PC

(57) ABSTRACT

A device and methods for the non-invasive manipulation and detection of target objects such as cells, pathogens, microparticles, and nanoparticles in vivo using an external magnetic field are described. In one aspect, a device and method for capturing and detecting intrinsically magnetic target objects or target objects labeled with at least one magnetic particle within the area of interest using an in vivo flow cytometer are described.

50 Claims, 29 Drawing Sheets

(51) Int. Cl.
*A61B 18/20* (2006.01)
*G01N 15/14* (2006.01)

(56) References Cited

U.S. PATENT DOCUMENTS

| | | | |
|---|---|---|---|
| 6,833,540 B2 | 12/2004 | MacKenzie et al. | |
| 7,220,385 B2 * | 5/2007 | Blecka et al. | 422/64 |
| 2002/0099283 A1 | 7/2002 | Christ et al. | |
| 2003/0216663 A1 | 11/2003 | Jersey-Willuhn et al. | |
| 2004/0039379 A1 | 2/2004 | Viator et al. | |
| 2004/0188602 A1 | 9/2004 | Chinn et al. | |
| 2005/0124869 A1 | 6/2005 | Hefti et al. | |
| 2005/0175540 A1 | 8/2005 | Oraevsky et al. | |
| 2006/0078949 A1 * | 4/2006 | Offer et al. | 435/7.21 |
| 2007/0015978 A1 | 1/2007 | Kanayama et al. | |
| 2007/0015992 A1 | 1/2007 | Filkins et al. | |
| 2007/0121697 A1 | 5/2007 | Burgholzer et al. | |
| 2007/0213613 A1 | 9/2007 | Ishida et al. | |
| 2007/0269345 A1 * | 11/2007 | Schilffarth et al. | 422/73 |
| 2009/0093713 A1 | 4/2009 | Hyde et al. | |
| 2009/0156932 A1 | 6/2009 | Zharov | |
| 2009/0227997 A1 | 9/2009 | Wang et al. | |
| 2013/0030307 A1 | 1/2013 | Rajan et al. | |
| 2013/0060122 A1 | 3/2013 | Zharov | |

OTHER PUBLICATIONS

English translation of DE 10343442A1.*
Galanzha et al.; "Photoacoustic Flow Cytometry"; Methods; Jul. 2012; vol. 57; No. 3; pp. 280-296.
PCT/US13/61673 International Search Report and Written Opinion mailed Dec. 16, 2013 (8 pages).
U.S. Appl. No. 13/661,551 Office Action mailed Feb. 13, 2014 (14 pages).
Givan; "Flow Cytometry: An Introduction in Flow Cytometry Protocols"; Second Edition, Methods in Molecular Biology, vol. 263; pp. 1-31; Humana Press; 2004.
Hawley et al.; "Flow Cytometry Protocols" Second Edition; Methods in Molecular Biology, vol. 263; Books, Software, and Web Site Reviews; Clinical Chemistry vol. 51; No. 3; pp. 678-679; 2005.
Office Action from related U.S. Appl. No. 13/253,767, dated Oct. 6, 2014, 18 pgs.
Office Action from related U.S. Appl. No. 13/661,551, dated Oct. 7, 2014, 10 pgs.
Zharov, "Photothermal image flow cytometry in vivo", Optics Letters, 2005, pp. 628-630, vol. 30, No. 6.
Ara et al, "Irradiation of pigmented melanoma cells with high intensity pulsed radiation generates acoustic waves and kills cells." Lasers in Surgery and Medicine, 1990, pp. 52-59, vol. 10 No. 1.
Kim et al, "In situ fluorescence microscopy visualization and characterization of nanometer-scale carbon nanotubules labeled with 1-pyrenebutanoic acid, succinimdylester," Applied Physics Letters, 2006, pp. 213110, vol. 88.
Lapotko et al, "Spectral evaluation of laser-induced cell damage with photothermal microscopy," Lasers in Surgery and Medicine, 2005, pp. 22-30, vol. 36, No. 1.
Liao et al, "Gold nanorod bioconjugates," Chemistry of Materials, 2005, pp. 4636-4641, vol. 17, No. 18.
Weight et al, "Photoacoustic detection of metastatic melanoma cells in the human circulatory system.", Optics Letters, 2006, pp. 2998-3000, vol. 31, No. 20.
Zharov et al, "Photothermal imaging of nanoparticles and cells" IEEE Journal of Selected Topics in Quantum Elextronics, 2005, pp. 733-751, vol. 11, No. 4.
Zharov et al, "In vivo photothermal flow cytometry: imaging and detection of individual cells in blood and lymph flow", Journal of Cellular Biochemistry, 2006, pp. 916-932, vol. 97, No. 5.
Office Action from related U.S. Appl. No. 12/334,217, dated Apr. 26, 2012, 10 pgs.
Interview Summary dated Aug. 13, 2012 from related U.S. Appl. No. 12/334,217; 3 pages.
Office Action from U.S. Appl. No. 12/334,217, dated Nov. 30, 2011, 12 pages.
Zharov et al., "In vivo photoacoustic flow cytometry for monitoring of circulating single cancer cells and contrast agents", Optics Letters (2006), pp. 3623-3625, vol. 31, No. 24.

* cited by examiner

DEVICE AND METHOD FOR IN VIVO NONINVASIVE MAGNETIC MANIPULATION OF CIRCULATING OBJECTS IN BIOFLOWS

CROSS REFERENCE TO RELATED APPLICATION

This application is a continuation-in-part of U.S. patent application Ser. No. 12/334,217, entitled "Device and Method for In Vivo Flow Cytometry Using the Detection of Photoacoustic Waves" filed on Dec. 12, 2008, which is hereby incorporated by reference in its entirety.

GOVERNMENTAL RIGHTS IN THE INVENTION

This work was supported in part by the National Institutes of Health grants number R01EB000873, R21EB0005123, R01CA131164, R21CA139373, and R01EB009230, as well as the National Science Foundation grant number DBI-0852737. The U.S. Government may have certain rights in this invention.

FIELD OF THE INVENTION

This application relates to a device and methods for the non-invasive manipulation of target objects such as cells, pathogens, proteins, microparticles, and nanoparticles in vivo using an external magnetic field. In one aspect, this application relates to manipulating and detecting intrinsically magnetic target objects or target objects labeled with magnetic labeling compounds within the area of interest using an in vivo flow cytometer.

BACKGROUND

Advancements in medical research have led to unprecedented characterization of a plethora of factors involved in the development and progression of many diseases on cellular, subcellular, and molecular levels. Using advanced measurement techniques such as reverse transcriptase polymerase chain reaction (RT-PCR), advanced in vitro flow cytometry, and microchip fluid technology, researchers have gained valuable insights with potential applications in the treatment of many diseases.

A particularly challenging issue in medical research is the detection and characterization of relatively rare cells such as tumor-initiating cancer stem cells (CSCs), a treatment-resistant subclass of tumor cells thought to be responsible for the growth and regrowth of primary and metastatic tumors. The development of metastatic disease may be governed by the migration of CSCs from an existing tumor mass to remote locations via the circulatory or lymphatic system. The circulating tumor cells (CTCs) migrating within the circulatory or lymphatic systems typically include a relatively large number of differentiated tumor cells, and a tiny subset of undifferentiated stem circulating tumor cells (stem CTCs) associated with metastatic disease. Because of the rarity of the stem CTCs in circulation, their detection is exceedingly difficult due to limitations of existing measurement methods.

The sensitivity threshold of existing stem CTC assays, such as reverse transcriptase polymerase chain reaction (RT-PCR) assays, CellSearch system technology, in vitro flow cytometry, and microchip fluid technology is limited to approximately 1 cell per mL of sample due to the relatively small volume processed by the assay's instrumentation, which is typically about 10 mL or less. This sensitivity is inadequate to reliably detect these rare stem CTCs, which may circulate in concentrations of about 1 cell per 50 mL of blood or at even lower concentrations.

In vivo flow cytometry techniques, which detect cells as they circulate within the blood vessels of a living subject, overcome the sample volume limitation, since these techniques are capable of processing the entire blood volume of the subject as it passes through a particular blood vessel. However, for the detection of rare cells such as stem CTCs, the cell must pass though the area of interest of the instrumentation, typically a superficial blood vessel or lymph vessel. The amount of time required to observe a large volume of blood passing through the area of interest may be significant, especially when detecting and characterizing both the undifferentiated stem CTCs and the differentiated CTCs.

A need exists in the art to selectively enrich the concentration of cells circulating in vivo in order to enhance the sensitivity of the detection using in vivo flow cytometry techniques, among other needs. Such an enhancement would make possible the detection of relatively rare cells in a shorter amount of time, significantly increasing the cell detection sensitivity of the in vivo flow cytometry instrumentation. The increased cell detection sensitivity may allow for the earlier detection and treatment of diseases related to circulating rare cells such as the development of metastatic diseases from circulating stem CTCs.

SUMMARY

Aspects of the present invention provide a device for the manipulation and detection of a magnetic target object within a moving biofluid of a living organism such as blood, lymph or cerebrospinal fluid. The device includes an in vivo flow cytometer for detecting the magnetic target object within an area of interest such as within a circulatory vessel through which the biofluid moves. The device also includes at least one magnet situated from about 0.1 mm to about 20 cm of the area of interest, depending on magnetic field strength, which may range from about 0.1 Tesla to about 20 Tesla. The at least one magnet may produce a magnetic field that manipulates the magnetic target object within the area of interest.

By using an external magnetic field to manipulate magnetic target objects, the magnetic target objects may be enriched, sorted, separated, captured, and/or immobilized as they are carried into the area of interest by the moving biofluid. For example, the magnetic target objects may be locally concentrated within the area of interest of the in vivo flow cytometer, significantly enhancing the detection sensitivity of the device, in particular if the magnetic target objects occur at extremely low concentrations within the moving biofluid.

In one particular arrangement, the device may be used to detect the presence of magnetic target objects within the moving biofluid of the living organism using a method that includes situating at least one magnet from about 0.1 mm to about 20 cm of an area of interest to alter the movement of the moving magnetic target objects within a magnetic field produced by the at least one magnet. The method further includes detecting the magnetic target objects using an in vivo flow cytometer.

In another aspect, a method is provided for detecting the presence of target cells within a moving biofluid of a living organism that includes injecting magnetic nanoparticles conjugated with a first targeting moiety into the moving biofluid to produce magnetic target cells that include the magnetic particles attached to the target cells. In this method, photoacoustic contrast agents conjugated with a second targeting moiety different than the first targeting moiety may be injected into the moving biofluid to produce magnetic target cells labeled with the photoacoustic contrast agents. The first and second targeting moieties are different from each other, but both specifically target the attachment of the magnetic particle and the photoacoustic contrast agent to the same target cell type, which may be a cancer stem cell or other cell associated with a disease or disorder.

This method further includes situating at least one magnet from about 0.1 mm to about 20 cm from an area of interest to alter the movement of the magnetic target cells within a magnetic field produced by the at least one magnet, and detecting the magnetic target objects using an in vivo photoacoustic flow cytometer. The method also includes subjecting the magnetic target cells to an additional process that may include removing the target cells for biochemical or genetic analysis; non-invasive eradication using high-energy pulses chosen from laser pulses, microwave pulses, or ultrasound pulses; magnetic purging; mechanical removal; needle extraction; or any combination thereof.

Additional objectives, advantages and novel features will be set forth in the description which follows or will become apparent to those skilled in the art upon examination of the drawings and the detailed description which follows.

BRIEF DESCRIPTION OF THE DRAWINGS

FIG. 23A is a fluorescent microscopic image of the suspension with no external magnetic field applied. FIG. 23B is a fluorescent microscopic image of the same suspension after the end of a magnet is attached to the top of the slide cover.

FIG. 24A is a non-linear photothermal (PT) signal obtained from the suspension with no external magnetic field applied. FIG. 24B is a non-linear photothermal (PT) signal obtained from the same suspension after the end of a magnet is attached to the top of the slide cover.

FIG. 25A is a fluorescent microscopic image of the labeled cancer cell with no external magnetic field applied. FIG. 25B is a fluorescent microscopic image of the same labeled cancer cell after the end of a magnet is attached to the top of the slide cover.

FIG. 26A is a non-linear photothermal (PT) signal obtained from the labeled cancer cell with no external magnetic field applied. FIG. 26B is a non-linear photothermal (PT) signal obtained from the same labeled cancer cell after the end of a magnet is attached to the top of the slide cover.

Corresponding reference characters indicate corresponding elements among the views of the drawings. The headings used in the figures should not be interpreted to limit the scope of the claims.

DETAILED DESCRIPTION

Figure 1:
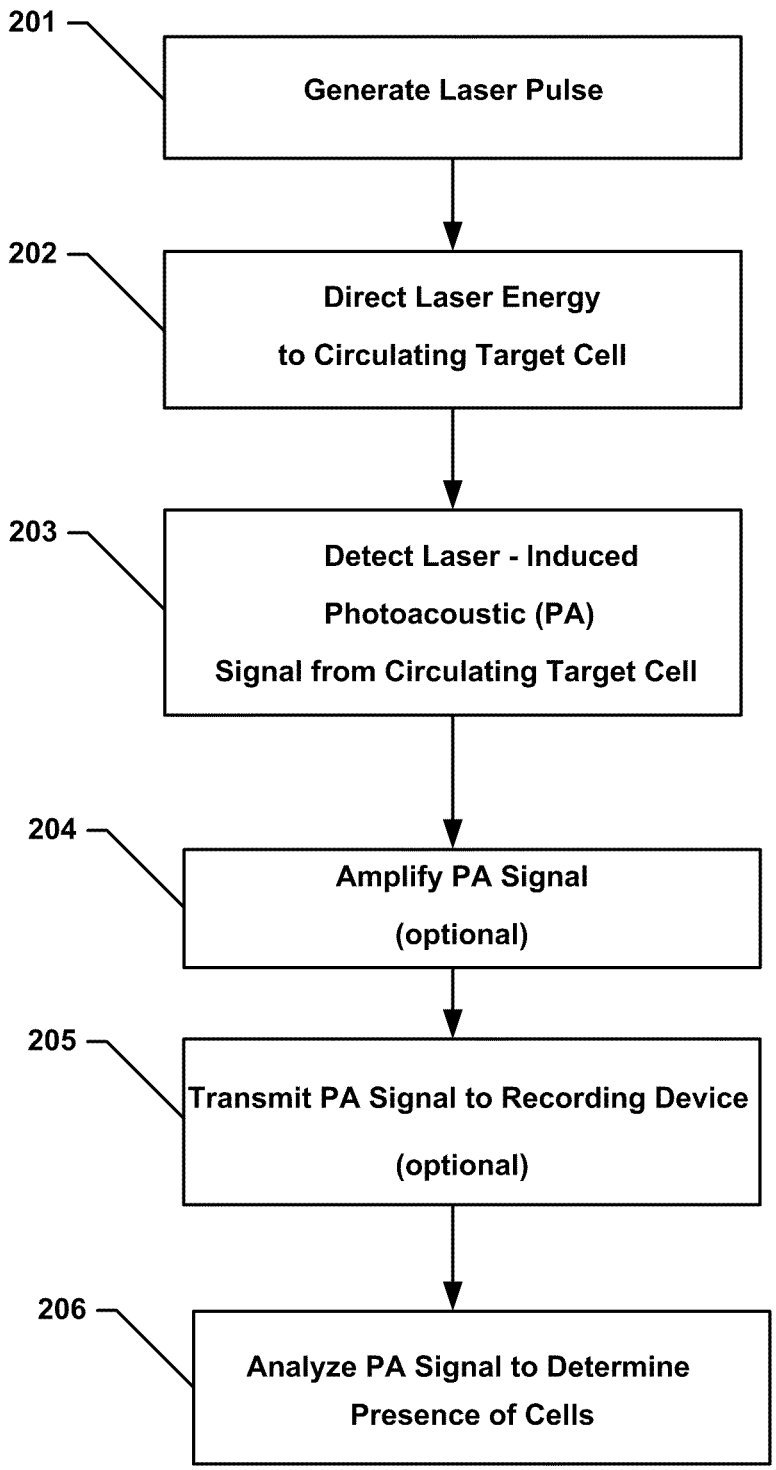
FIG. 1 is a flow chart of a photoacoustic in vivo flow cytometry method.

A device for detecting the presence of target objects within a moving biofluid of a living organism is provided in one aspect. This device incorporates the manipulation of magnetic target objects within a magnetic field applied to the area of interest of an in vivo flow cytometer, resulting in a detection sensitivity that is significantly enhanced relative to previously described in vivo flow cytometry systems. The manipulation of the target objects may include but is not limited to locally enriching the concentration of target objects within the area of interest, capturing or immobilizing the target objects within the area of interest, spatially separating or sorting two or more target objects within the area of interest, concentrating the target objects within a selected region of the biofluid, or any combination thereof. The target objects may be intrinsically magnetic, or the target objects may be rendered magnetic by the attachment of magnetic particles to the target cells. The magnetic particles specifically bind to the desired target particles due to the conjugation of the magnetic particles with targeting moieties such as antibodies or ligand proteins that are characteristic components of the target objects. The target objects may be biomarkers, pathogens such as viruses or bacteria, normal cells such as circulating red blood cells, or abnormal cells such as circulating cancer stem cells. The device may further be capable of non-invasively eradicating the target objects captured within the area of interest once the identity of the target objects has been confirmed using the detection device.

In another aspect, a method of using the device to detect the presence of target objects within a moving biofluid of a living organism is provided. The method may include labeling the target object by injecting magnetic particles conjugated to targeting moieties into the moving biofluid, as well as injecting contrast agents conjugated to second targeting moieties into the moving biofluid, producing a target object labeled with both a magnetic particle and a contrast agent. The type of contrast agent may be any contrast agent compatible with the detection sensors of the in vivo flow cytometry device, including but not limited to photoacoustic contrast agents, ultrasound contrast agents, and fluorescent markers. Once the targeting agent has been labeled, a magnet is situated in the vicinity of the area of interest to alter the movement of the labeled target objects, and the in vivo flow cytometry device is used to detect the labeled target objects within the area of interest. The target objects may also be removed for further biochemical or genetic analysis, or may be eradicated using a technique including but not limited to overheating by excessive photoabsorption effects.

The device and methods of using the device, as well as the target objects, magnetic particles and contrast agents used to label the target objects are described in detail below.

I. Description of Device

In various aspects, the device may include an in vivo flow cytometer and at least one magnet, described below.

a. In Vivo Flow Cytometer

In an aspect, the device includes an in vivo flow cytometer that may be any known in vivo flow cytometer, including, but not limited to, the photoacoustic flow cytometry device (PAFC) described in U.S. patent application Ser. No. 12/334,217, the contents of which are incorporated herein in their entirety. Although any in vivo flow cytometer may be included in the device, the device will be described herein assuming the inclusion of a PAFC.

Referring to FIG. 1, the PAFC detects target objects in a moving biofluid by generating a laser pulse at step 201 and directing the laser energy resulting from the laser pulse to the area of interest containing the circulating target cell at step 202. The target cell, which may either possess intrinsic photoacoustic (PA) properties or may be labeled with a PA contrast agent, emits a PA signal that is detected at step 203. The detected PA signal may be amplified at step 204, recorded at step 205, and analyzed at step 206 to determine the presence of the target cell in the area of interest.

Figure 2A:
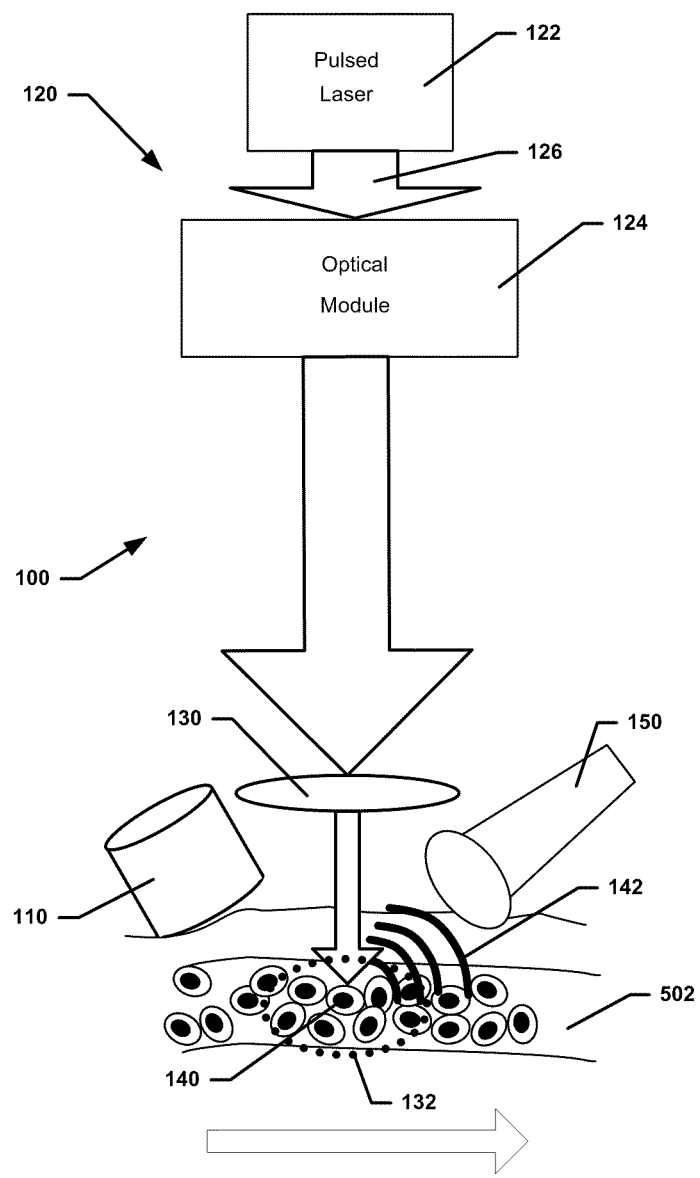
FIG. 2 includes two schematic diagrams illustrating an in vivo flow cytometry device with an external magnet attached near the area of interest (FIG. 2A) and an in vivo flow cytometry device that includes a magnet integrated into the optical module (FIG. 2B).

Referring to FIG. 2A, in one aspect the device 100 includes an in vivo flow cytometer 120 used to detect the presence of target objects 140 within the area of interest 132 of a moving biofluid 502. In this aspect, the in vivo flow cytometer 120 may be a PAFC that includes a pulsed laser 122 capable of emitting laser energy 126 ranging between wavelengths of about 400 nm and about 2500 nm, and may further include an optical module 124 to convert the wavelength, pulse duration, or both wavelength and pulse duration emitted by the pulsed laser 122 to desired values. For example, a Raman shifter may be used to deliver a probe pulse having a wavelength and pulse duration that are different from the pump pulse received from the pulsed laser 122. In addition, the in vivo flow cytometer 120 may further include optical elements 130 such as lenses or optic fibers to direct the laser energy 126 to the target objects 140. The in vivo flow cytometer 120 may also include at least one ultrasound transducer 150 to detect photoacoustic waves 142 emitted by the target objects 140.

In other aspects, the in vivo flow cytometer 120 may utilize one or more known detection methods to detect the target objects 140. Non-limiting cell detection methods suitable for use by an in vivo flow cytometer 120 include photoacoustic methods, photothermal methods, fluorescent methods, Raman and other scattering methods, and any combination thereof.

Figure 48:
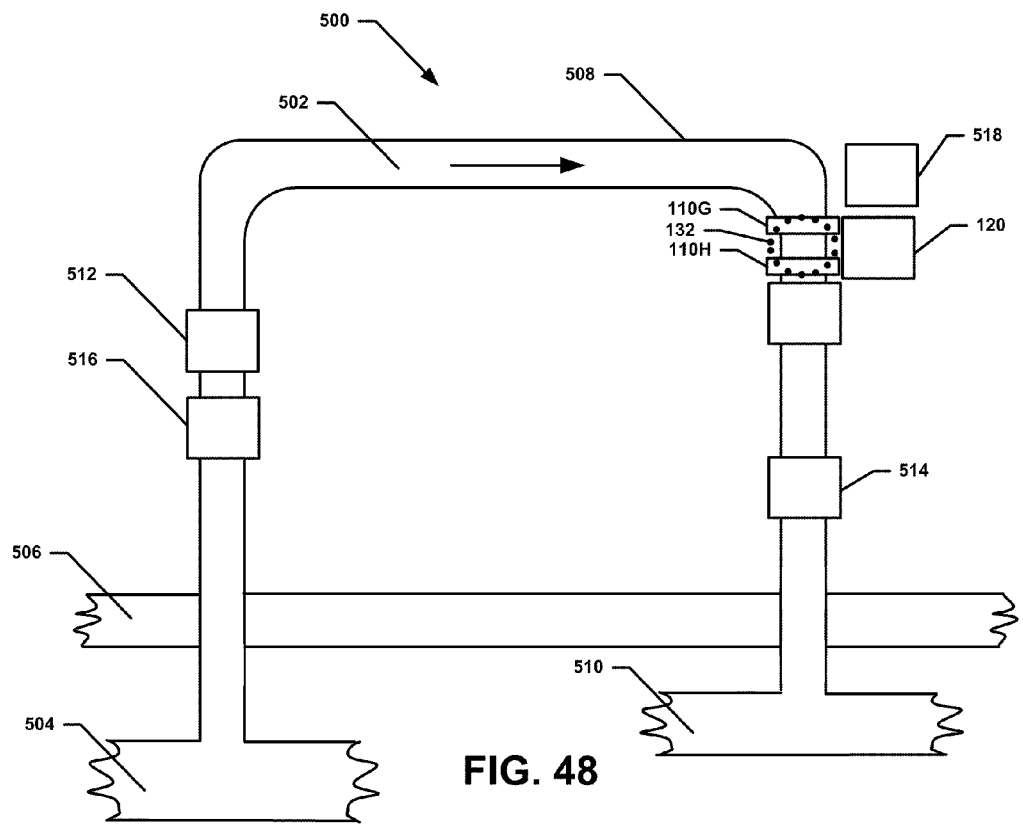
FIG. 48 is a diagram of an extracorporeal shunt inserted into an organism to direct the flow of a biofluid outside of the organism and to return the biofluid back into the organism.

As shown in FIG. 48, the in vivo flow cytometer 120 may detect target objects 140 in a moving biofluid 502 flowing through an extracorporeal shunt 500. The extracorporeal shunt 500 directs the moving biofluid 502 from an afferent circulatory vessel 504 such as an artery within the integument 506 of an organism to a circulatory bypass tube 508 outside of the organism. The target objects 140 may be detected as they move through an area of interest 132 by the in vivo flow cytometer 120. The moving biofluid 502 is returned back into an efferent circulatory vessel 510 such as a vein within the integument 506 of an organism. A pump 516 such as a peristaltic pump may be further included to move the biofluid 502 through the circulatory bypass tube 508. A high speed high resolution imaging mode optical system 518 may be used to provide visualization of individual moving cells at single cell level, as well as to guide the placement of the elements of the in vivo flow cytometer 120. Other aspects of the extracorporeal shunt 500, such as the manipulation of the movement of the target objects 140 using magnets 110G and 110H, are discussed in further detail below.

If the target objects 140 are immobilized within the area of interest 132, either within the organism or within an extracorporeal shunt 500, other methods and devices in addition to an in vivo flow cytometer 120 may be used to detect and characterize the target objects 140. Non-limiting examples of suitable devices for the detection and characterization of immobilized target objects 140 include MRI, CT, PET, ultrasound, and conventional or fluorescent microscopy devices.

b. Magnet

The device 100 may further include a magnet 110 situated in close proximity to the area of interest 132 such that the magnetic field induced by the magnet 110 alters the movement of the target objects flowing past the area of interest 132, as shown in FIG. 2A. The target objects 140 may be intrinsically magnetic or may be labeled with attached magnetic particles, rendering them susceptible to the forces induced by a magnetic field produced by the magnet 110. The magnetic field may manipulate the target objects 140 within the area of interest 132. Non-limiting examples of manipulations of the target objects 140 include: immobilization, enrichment, sorting, separating, concentration within a selected region of the biofluid, and combinations thereof within the area of interest 132.

Figure 2B:
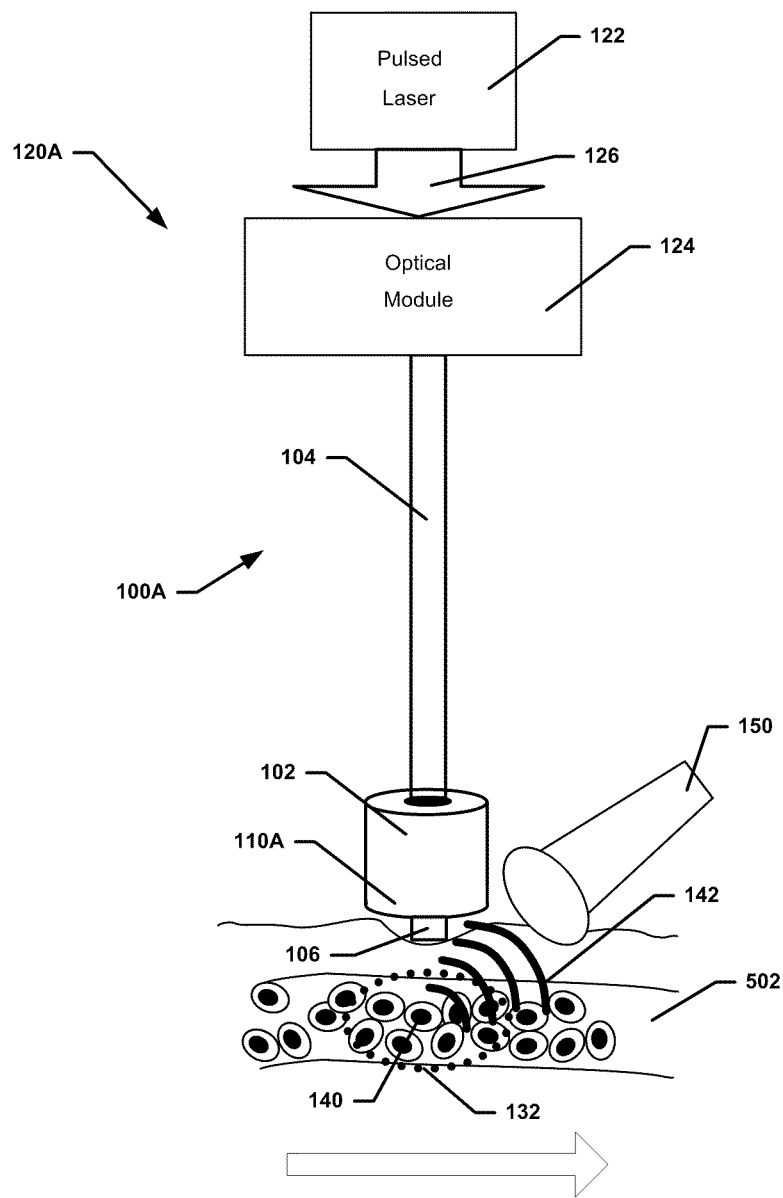

The magnet 110A may also be incorporated into the in vivo flow cytometer 120, as shown in FIG. 2B. In this aspect, the laser energy 126 may be directed to the area of interest 132 using an optic fiber 104 that includes a focusing tip 106. The material of the magnet 110A may form a channel 102 through which the laser fiber 104 may pass in order to situate the focusing tip 106 in a laser pulse location that is essentially coincident with the corresponding magnetic field produced by the magnet 110A.

As shown in FIG. 48, one or more magnets 110H-110G may be situated in close proximity to a circulatory bypass tube 508. The target objects may be captured, sorted, or otherwise manipulated by a magnetic field produced by the one or more magnets 100G-110H within the area of interest 132 in which the in vivo flow cytometer 120 detects the target objects.

The magnet 110 may be any existing permanent magnet or electromagnet capable of producing a steady or pulsed magnetic field at the magnet surface of at least 0.1 T. In other aspects, the magnetic field strength at the magnet surface may be from about 0.1 T to about 7 T, from about 0.1 T to about 0.5 T, from about 0.25 T to about 0.75 T, from about 0.5 T to about 1 T, from about 0.75 T to about 1.5 T, from about 1 T to about 2 T, from about 1.5 T to about 2.5 T, from about 2 T to about 4 T, from about 3 T to about 5 T, from about 4 T to about 6 T, from about 5 T to about 7 T, from about 6 T to about 8 T, from about 7 T to about 9 T, from about 8 T to about 10 T, from about 9 T to about 11 T, from about 10 T to about 12 T, from about 11 T to about 13 T, from about 12 T to about 14 T, from about 13 T to about 15 T, from about 14 T to about 16 T, from about 15 T to about 17 T, from about 16 T to about 18 T, from about 17 T to about 19 T, and from about 18 T to about 20 T. The strength of the magnetic field at the magnetic surface may be selected to be sufficiently strong to capture the target objects 140 moving through the area of interest 132. The strength of the magnetic field sufficient for the capture of moving target objects 140 may be influenced by any one or more of at least several factors including, but not limited to, the size of the circulatory vessel through which the biofluid 500 may flow, the depth of the circulatory vessel relative to the skin surface of the organism, the flow speed of the biofluid 500 through the area of interest 132, the separation distance between the magnet 110 and the area of interest 132, the duration of the magnetic pulse produced by a pulsed electromagnet, the intrinsic magnetic properties of the target object 140, and the amount of magnetic material used to label the target object 140, among other possible factors.

The magnet 110 may be constructed using any known magnetic material, including but not limited to hematite ($Fe_2O_3$), magnetite ($Fe_3O_4$), manganese-zinc ferrite ($Mn_aZn_{(1-a)}Fe_2O_4$), nickel-zinc ferrite ($Ni_aZn_{(1-a)}Fe_2O_4$), barium oxide, strontium oxide, and combinations thereof. In an aspect, the magnet may be a cylindrical neodymium-iron-boron (NdFeB) magnet with Ni—Cu—Ni coating. Any known electromagnet may be used including but not limited to resistive electromagnets and superconducting magnets.

In an aspect, the magnet 110 may be situated at a distance ranging from about 50 μm to about 20 cm from the area of interest 132, depending on the strength of the magnet 110. In other aspects, the magnet 110 may be situated at a distance ranging from about 50 μm to about 200 μm, from about 100 μm to about 300 μm, from about 200 μm to about 400 μm, from about 300 μm to about 500 μm, from about 400 μm to about 600 μm, from about 500 μm to about 700 μm, from about 600 μm to about 800 μm, from about 700 μm to about 900 μm, from about 800 μm to about 1 mm, from about 0.9 mm to about 1.1 mm, from about 1 mm to about 1.4 mm, from about 1.2 mm to about 1.6 mm, from about 1.4 mm to about 1.8 mm, from about 1.6 mm to about 2.0 mm, from about 1.8 mm to about 2.2 mm, from about 2 mm to about 2 cm, from about 1 cm to about 3 cm, from about 4 cm to about 6 cm, from about 5 cm to about 7 cm, from about 6 cm to about 8 cm, from about 7 cm to about 9 cm, from about 8 cm to about 10 cm, from about 9 cm to about 11 cm, from about 10 cm to about 15 cm, and from about 14 cm to about 20 cm from the area of interest 132. In another aspect, the magnet 110 may be attached externally to the integument surface of the organism in close proximity to the area of interest 132.

Figure 47:
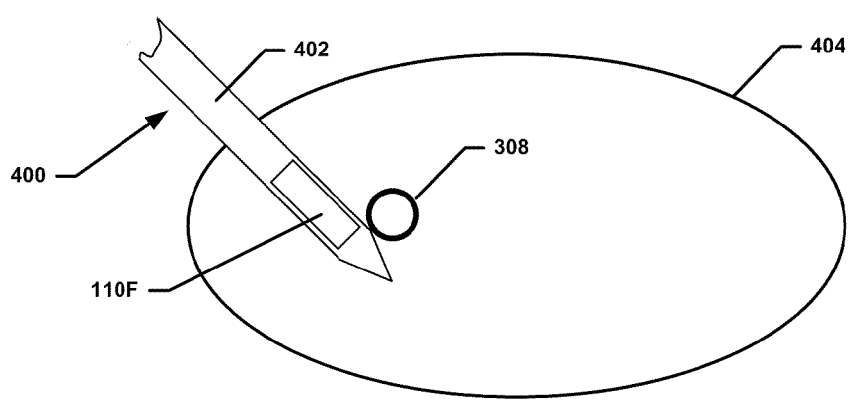
FIG. 47 is a diagram of a minimally invasive needle device shown inserted into an organism to situate a magnet in close proximity to a circulatory vessel.

In another aspect, the magnet 110 may be situated in close vicinity of the area of interest 132 using a minimally invasive needle delivery device. In yet another aspect, the magnet 110 may be situated in close vicinity of the area of interest 132 using a magnet 110 mounted in a catheter device. An illustration of a minimally invasive needle device 400 in one particular aspect is shown in FIG. 47. In this device 400, the magnet 110F may be situated within a needle 402 which may be inserted into the organism 404 so that the magnet 110F is in close proximity to a circulatory vessel 308, shown here in cross-section.

Figure 44:
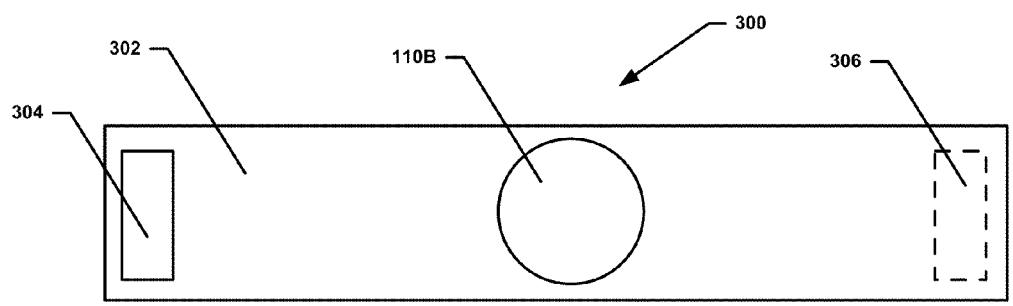
FIG. 44 is a diagram of a magnetic cuff.
Figure 45:
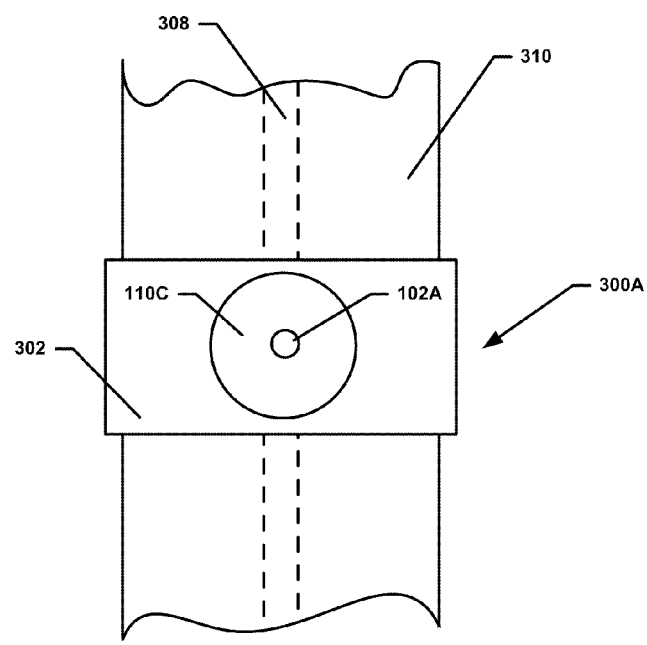
FIG. 45 is a diagram of a magnetic cuff secured to an extremity of an organism.

In still yet another aspect, the magnet 110 may be placed in close proximity to the area of interest 132 using a magnetic cuff that includes the magnet attached to a securing cuff. A schematic drawing of a magnetic cuff 300 is illustrated in FIG. 44. The magnetic cuff 300 includes a securing cuff 302 with an attached magnet 100B. The magnetic cuff 300 may also include a means of securing the cuff 302 such as a VELCRO hook strip 304 and loop strip 306. As shown in FIG. 45, the magnetic cuff 300A may be situated such that the magnet 110C is in close proximity to a circulatory vessel 308, and secured around an extremity 310 of the organism such as an arm to hold the magnet 110C in place. Once secured, the magnetic cuff 300 may be worn by the organism in order to alter the movement of the magnetic target objects within the circulatory vessel 308. While wearing the magnetic cuff 300, the organism may move without disturbing the placement of the magnet 110C relative to the circulatory vessel 308. In an aspect, the magnet 110C may further contain a channel 102A through which an optic fiber 104 (not shown) may be threaded in order to direct the laser pulses used for in vivo flow cytometry without removing or repositioning the magnet 110C.

The securing cuff 302 may be of any known design including a flexible strip secured using Velcro straps, a belt strap, releasable buckles, releasable clamps, or any other known securing means. The magnetic cuff may be worn by an organism for a period of time ranging from about 30 minutes to about 12 hours prior to the detection of the target objects 140 using the in vivo flow cytometer 120. The magnetic cuff may be secured around any extremity of the organism, including, but not limited to, an arm, a leg, a finger, a toe, a wrist, an elbow, a shoulder, an ankle, a knee, a hip, and a neck. In an additional aspect, the magnet may be attached to the external integument of the organism using an adhesive device including but not limited to an adhesive bandage or adhesive tape.

In an additional other aspect, the magnet 110 may be a pulsed magnet including but not limited to an MRI pulsed electromagnet to hold the target objects 140 within the area of interest 132. In this aspect, rather than capturing the target objects 140 using a time-invariant magnetic field, the pulsed magnet may produce a series of magnetic field pulses within the area of interest 132 that periodically alters the velocity of movement of the target objects 140 within the biofluid 500. For example, the magnetic pulses produced by the pulsed magnet may reverse the velocity of movement of the target objects 140 so that they move upstream into the area of interest 132 for the duration of the magnetic pulse, and then the velocity of the target objects 140 may gradually reverse direction and start to move downstream and away from the area of interest 132 before the next magnetic pulse returns the target objects to the area of interest 132.

Figure 49:
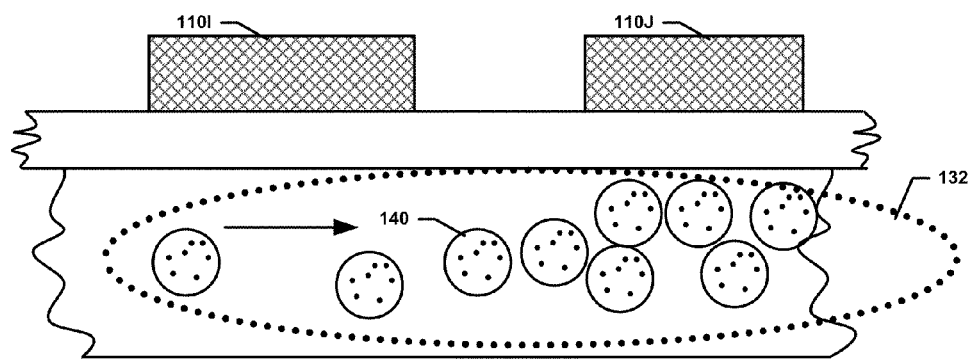
FIG. 49 is a diagram of an array of magnets enriching the concentration of magnetic target objects within an area of interest.

In still yet another aspect, the magnet 110 may include two or more magnets 110 arranged in an array to capture the target objects 140 within the area of interest 132; the array of magnets 110 may have any desired geometrical arrangement. For example, as shown in FIG. 49, the array of magnets may include two or more magnets 110I-100J arranged along the length of a circulatory vessel through which the biofluid 500 moves. In this example, the most upstream magnet 110I may only be capable of slowing the velocity of the target objects 140 relative to the surrounding biofluid movement, and the more downstream magnet 110J may then be capable of capturing the slowed target objects 140. In another example (not shown), the two or more magnets 110I-110J arranged along the length of the circulatory vessel may be of sufficient strength to capture the target objects 140 and immobilize the target objects 140 within the volume of the circulatory vessel that is situated between the two or more magnets 110 in the array.

Figure 50:
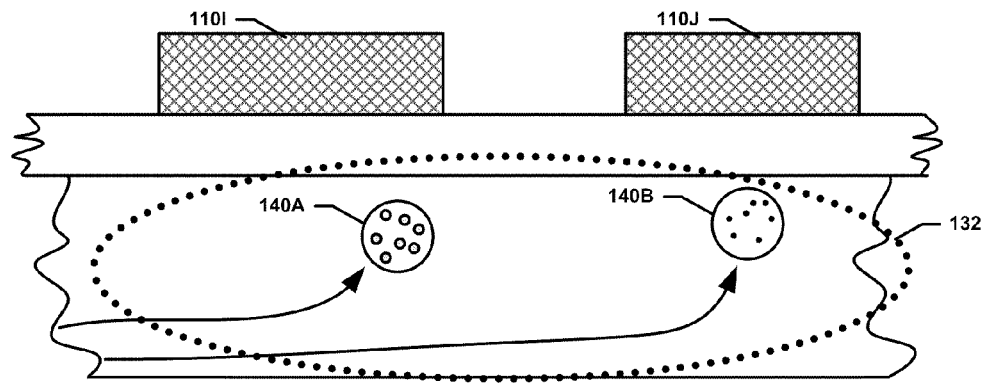
FIG. 50 is a diagram of an array of magnets spatially sorting a mixture of magnetic target objects within an area of interest.
Figure 51:
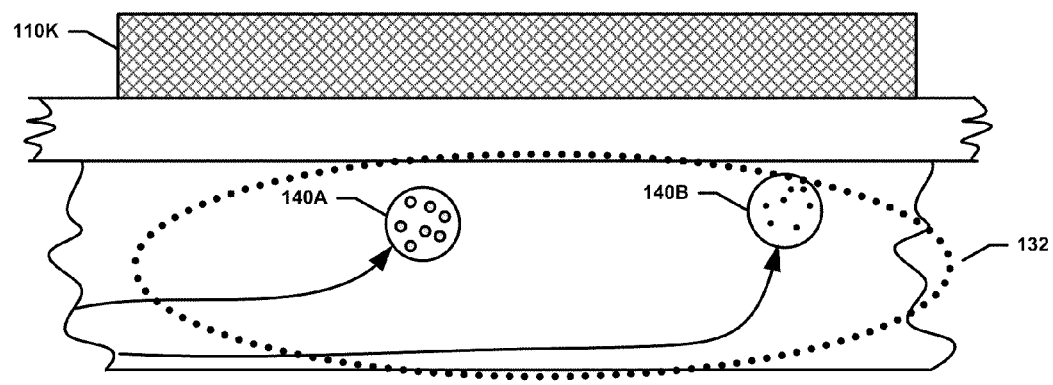
FIG. 51 is a diagram of a single magnet spatially sorting a mixture of magnetic target objects within an area of interest.

Referring to FIG. 50, an array of magnets 110I-110J may also provide the capability to sort and capture two or more different target objects 140A and 140B. In this aspect, the more upstream magnet 110I may produce a magnetic field of sufficient strength to capture target objects 140A, which may be more susceptible to capture due to one or more factors including but not limited to a smaller size or mass relative to target object 140B, a smaller concentration of magnetic materials relative to target objects 140B, a smaller size of magnetic particles attached to the target objects 140A relative to target objects 140B, or a smaller number of magnetic particles attached to the target objects 140A relative to target objects 140B. Further, the more downstream magnet 100J may produce a magnetic field of sufficient strength to capture target objects 140B, which were slowed relative to the flow of the biofluid by the more upstream magnet 100I. As a result, target objects 140A and 140B may be spatially separated and captured using an array of magnets 110I-110J as shown in FIG. 50. In another aspect, a single long magnet 110K may be used in place of the array of magnets in order to spatially separate and capture two or more different target objects 140A and 140B, as shown in FIG. 51.

Figure 46:
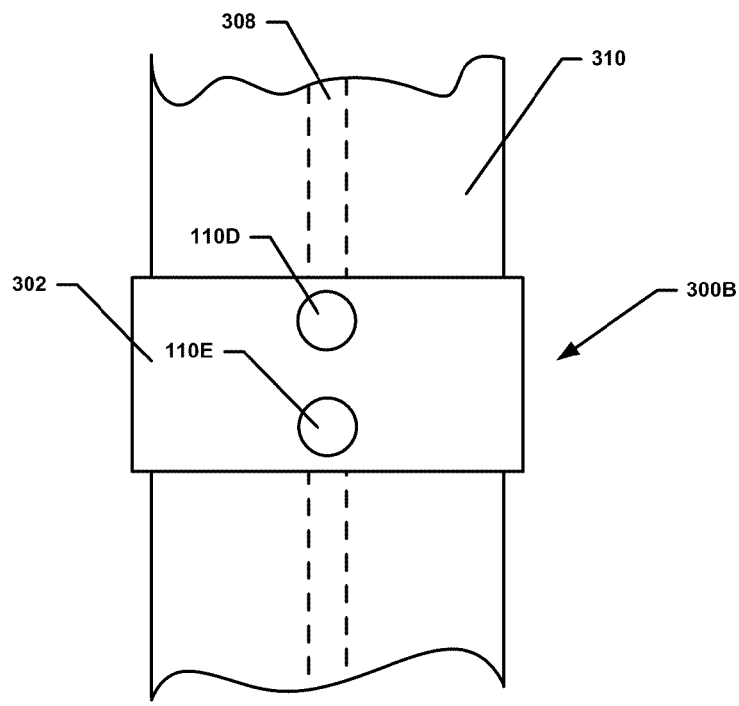
FIG. 46 is a diagram of a magnetic cuff that includes an array of two magnets, shown secured to an extremity of an organism.

A magnetic cuff 300B that incorporates two magnets 110D and 100E is illustrated in FIG. 46. In this aspect, the two magnets 110D and 110E are situated along the length of circulatory vessel 308 in close proximity to the vessel 308. The securing cuff 302 may then be secured around the extremity 310 of the organism to hold the magnets 110D and 110E in place relative to the circulatory vessel 308.

The target objects 140 may be concentrated near the area of interest using methods other than applied magnetic fields. For example, target objects 140 possessing a larger diameter than the surrounding cells may be concentrated by reducing the cross-sectional area of the lumen of a circulatory vessel through which the biofluid 500 flows in the vicinity of the area of interest 132 using gentle mechanical pressure on the tissue surrounding the circulatory vessel, thereby retaining the larger diameter target objects 140, while allowing the surrounding cells with smaller diameter than the target objects 40 to flow away unimpeded from the area of interest 132. The amount of pressure applied to the tissue surrounding the circulatory vessel may be regulated using cell detection rates obtained using the in vivo flow cytometer 120 at different levels of mechanical pressure.

II. Target Objects

The device 100 may be used to detect target objects 140 in a moving biofluid of a living organism. The devices and methods discussed herein may be used on any organisms that possess a moving biofluid. Non-limiting examples of living organisms that possess a moving biofluid include vertebrates such as mammals, reptiles, birds, amphibians, and fish; plants; fungi; mollusks; insects; arachnids; annelids; arthropods; roundworms; and flatworms. Non-limiting examples of suitable moving mammalian biofluids include blood, lymph, cerebrospinal fluid, urine, chyme, cytosol, tears, and interstitial fluid. Other non-limiting examples of non-mammalian moving biofluids include hemolymph and intracellular fluid.

The moving biofluid and target objects 140 may flow through a circulatory vessel, defined herein as any fluid-containing space within a living organism through which the flow of a biofluid is directed. Non-limiting examples of circulatory vessels in vertebrate living organisms include blood or lymphatic vessels. Other non-limiting examples of circulatory vessels include capillaries, arterioles, venules, arteries, veins, lymphatic vessels, hyphae, phloem, xylem, hemocoels, and sinuses. The circulatory vessels may be located in many different organs and tissues, including, but not limited to, skin, lip, eyelid, interdigital membrane, retina, ear, nail pad, scrotum, lymph nodes, brain, breast, prostate, lung, colon, spleen, liver, kidney, pancreas, heart, testicular, ovarian, lung, uterus, bone, bone marrow, peritoneum, skeletal muscle, smooth muscle, and bladder tissues.

The area of interest through which a moving biofluid flows may be at a depth ranging from about 10 m to about 15 cm below the surface of the integument of a living organism. If the moving biofluid is detected within a circulatory vessel or an extracorporeal shunt, the diameter of the circulatory vessel or shunt may range from about 10 µm to about 2 cm.

In another aspect, the target objects 140 may be magnetic target objects in order to be susceptible to the magnetic forces produced by the magnet 110 within the area of interest 132. In this aspect, magnetic target objects 140 may include intrinsically magnetic target objects, target objects labeled with magnetic particles, and any combination thereof. Non-limiting examples of target objects 140 suitable for detection by the device 100 include unlabeled biological cells having intrinsic magnetic properties such as red blood cells and iron-containing siderophilic bacteria, biological cell products having intrinsic magnetic properties, unbound contrast agents having intrinsic magnetic properties, unbound magnetic particles, biological cells labeled using magnetic particles, biological cell products or active pharmaceutical compounds labeled using magnetic particles, and any combination thereof. The target objects 140 may be endogenous or exogenous biological cells or cell products that may possess intrinsic magnetic properties or may be labeled using magnetic particles. Non-limiting examples of suitable cells or cell products include normal, apoptotic and necrotic red blood cells and white blood cells; aggregated red blood cells or white blood cells or clots; infected cells; inflamed cells; stem cells; dendritic cells; platelets; metastatic cancer cells resulting from melanoma, leukemia, brain cancer, breast cancer, colon cancer, prostate cancer, ovarian cancer, pancreatic cancer, and testicular cancer; bacteria; viruses; fungal cells; protozoa; microorganisms; pathogens; animal cells; plant cells; and leukocytes activated by various antigens during an inflammatory reaction and combinations thereof. Non-limiting examples of biological cell products include products resulting from cell metabolism or apoptosis, cytokines or chemokines associated with the response of immune system cells to infection, exotoxins and endotoxins produced during infections, specific gene markers of cancer cells such as tyrosinase mRNA, p97, MelanA/Mart1 produced by melanoma cells, PSA produced by prostate cancer, and cytokeratins produced by breast carcinoma.

In yet another aspect, the target objects 140 that are unlabeled biological cells may possess intrinsic magnetic properties due to the inclusion of magnetic materials such as iron in the composition of the unlabeled biological cells. For example, red blood cells contain iron within the enclosed hemoglobin, rendering the unlabeled red blood cells susceptible to capture by magnetic forces of sufficiently high magnetic field strength. Other non-limiting examples of metal-containing cell-specific markers that confer at least some degree of intrinsic magnetism to an unlabeled cell include hemoglobin (Hb), HbH, $HbO_2$, metHb, HbCN, HbS, HbCO, HbChr, myoglobins, cytochromes, catalase, porphyrins, chlorophylls, and combinations thereof.

In still yet another aspect, the target objects 140 may be labeled using attached magnetic particles to render the target objects 140 susceptible to capture by the magnetic field within the area of interest 132. The magnetic particles may be nanoparticles or microparticles ranging in size from about 5 nm to 10 µm. Non-limiting examples of suitable magnetic particles include ferromagnetic materials such as iron, nickel, cobalt, iron oxides, nickel oxides, cobalt oxides, alloys of rare earth metals, and any mixture or alloy thereof. In an additional aspect, the magnetic particles may include a magnetic material and an external coating of a biocompatible and/or non-toxic material including but not limited to gold, silver, titanium, and platinum. In order to selectively label the target objects 140, the magnetic particles may be conjugated with a cell-specific targeting moiety that has a high affinity for some unique feature of the target object 140 such as a cell membrane marker or receptor. Non-limiting examples of targeting moieties suitable for conjugation with a magnetic particle include antibodies, proteins, folates, ligands for specific cell receptors, receptors, peptides, viramines, wheat germ agglutinin, and combinations thereof. Non-limiting examples of suitable ligands include ligands specific to folate, epithelial cell adhesion molecule (Ep-CAM), Hep-2, PAR, CD44, epidermal growth factor receptor (EGFR), as well as receptors of cancer cells, stem cells receptors, protein A receptors of *Staphylococcus aureus*, chitin receptors of yeasts, ligands specific to blood or lymphatic cell endothelial markers, as well as polysaccharide and siderophore receptors of bacteria.

Two or more different magnetic particles conjugated with different cell-specific targeting moiety may be used to label each of two or more different cell types with one of the magnetic particles. For example, one cell type may be labeled with larger magnetic particles and another cell type may be labeled with smaller magnetic particles in order to facilitate the spatial sorting of the two cell types within the area of interest, as shown in FIGS. 50-51.

In an additional aspect, the magnetic particles may be eliminated relatively quickly from the circulation of the organism. For example, if the magnetic particles are magnetic nanoparticles conjugated to targeting moieties with an affinity to circulating tumor cells, the unbound conjugated magnetic nanoparticles in circulation may bind to the circulating tumor cells within about 15 minutes. Any unbound conjugated magnetic particles remaining in circulation only add to any background noise in the signals used to detect the circulating tumor cells by the in vivo flow cytometer 120. In this aspect, magnetic particles may be used that are eliminated a time period ranging from about 15 minutes to about 60 minutes.

In an additional other aspect, in order to enhance the detection sensitivity of the device 100, the target objects 140 may be labeled using a contrast agent to enhance a signal. Any existing contrast agent may be used that is compatible with the detection method used by the in vivo flow cytometer 120. Non-limiting examples of suitable contrast agents include an ultrasound contrast agent, a photoacoustic contrast agent, a hybrid contrast agent, a fluorescent contrast agent, a Raman contrast agent, an MRI contrast agent, a superconductivity quantum interference device contrast agent, a PET contrast agent, and a CT contrast agent. Non-limiting examples of specific contrast agents include indocyanine green dye, melanin, fluoroscein isothiocyanate (FITC) dye, Evans blue dye, Lymphazurin dye, trypan blue dye, methylene blue dye, propidium iodide, Annexin, Oregon Green, Cy3, Cy5, Cy7, Neutral Red dye, phenol red dye, AlexaFluor dye, Texas red dye, gold nanospheres, gold nanoshells, gold nanorods, gold cages, carbon nanoparticles, prefluorocarbon nanoparticles, carbon nanotubes, carbon nanohorns, magnetic nanoparticles, quantum dots, binary gold-carbon nanotube nanoparticles, multilayer nanoparticles, clustered nanoparticles, liposomes, liposomes loaded with contrast dyes, liposomes loaded with nanoparticles, micelles, micelles loaded with contrast dyes, micelles loaded with nanoparticles, microbubbles, microbubbles loaded with contrast dyes, microbubbles loaded with nanoparticles, dendrimers, aquasomes, lipopolyplexes, nanoemulsions, polymeric nanoparticles, and combinations thereof.

Hybrid contrast agents may include nanoparticle complexes or microparticle complexes that function simultaneously as contrast agents, depending on the particular materials and geometry of the magnetic particles. Non-limiting examples of suitable hybrid contrast agents include gold-magnetic complexes, quantum dot-magnetic complexes, carbon nanotube-magnetic complexes, radionucleotide-magnetic complexes, surface enhanced resonance scattering-magnetic complexes, or any combination thereof. In addition, the contrast agents described previously may also simultaneously function as magnetic particles depending on the materials included in the contrast agents.

The multilayer nanoparticles used as photoacoustic contrast agents for the target objects 140 may include two or more layers of materials with optical, thermal, and acoustic properties that enhance the PA signals 142 emitted by the target objects 140. Non-limiting examples of the effects of the multilayered nanoparticles on the PA pulses 142 emitted by the target objects 140 labeled with the multilayered nanoparticles include enhancing absorption of the laser pulse energy, increasing thermal relaxation time, increasing acoustic relaxation time, increasing the coefficient of thermal expansion, decreasing the coefficient of thermal diffusion, decreasing the local speed of sound near the target object 140, decreasing the threshold of bubble formation of the target object 140 and combinations thereof.

Exogenous target objects 140 such as unbound contrast agents and exogenous unlabeled biological cells may be introduced into the biofluid 500 of the organism perenterally, orally, intradermally, subcutaneously, or by intravenous or intraperitoneal administration. For example, unbound magnetic particles conjugated to targeting moieties may be injected intravenously into the moving biofluid 500 within a circulatory vessel in order to label the target objects 140.

To further increase the contrast between PA signals 42 or originating from the target objects 40 and the background PA signals from surrounding cells and tissues, a variety of approaches may be used. The organism may be exposed to hyperoxic or hypoxic atmospheric conditions to induce different levels of oxygenation, which in turn alters the light absorption properties of the red blood cells. The osmolarity of the biofluid 500 may be altered by injecting hypertonic or hypotonic solutions into the biofluid 500, thereby causing physical swelling or shrinking of surrounding cells, and further altering the light absorption characteristics of the surrounding cells. The hematocrit of the biofluid 500 may be altered by the injection of a diluting solution into the biofluid 500, thereby reducing the density of surrounding cells in the biofluid 500, and the resulting light absorption characteristics of the surrounding cells.

III. Methods of Manipulating and Detecting Target Objects

In an aspect, the device 110 may be used to detect the presence of a target object 140 with a detection sensitivity ranging from about 1 to about 100 target objects per L of biofluid. A method of detecting the presence of magnetic target objects 140 within a moving biofluid of a living organism may include situating at least one magnet 110 in close proximity an area of interest to alter the movement of the magnetic target objects 140 within a magnetic field produced by the at least one magnet 110. In this aspect, the captured magnetic target objects 140 may be detected using the in vivo flow cytometer 120.

As described previously, the magnetic target objects 140 may be intrinsically magnetic objects, or non-magnetic objects with attached magnetic particles. For example, the magnetic target object may be a circulating cancer stem cell labeled using an iron oxide nanoparticle conjugated with a protein ligand of a cell receptor characteristic of the circulating cancer stem cell.

In an aspect, the target objects 140 may be labeled using magnetic particles conjugated with a targeting moiety by injecting the conjugated magnetic particles into the moving biofluid within the organism. In this aspect, the conjugated magnetic particles may take a period of time ranging from about 15 minutes to about 60 minutes to selectively bind to the target objects 140. In addition, unbound magnetic particles are typically cleared from circulation about 20 minutes to about 60 minutes after injection, so that any magnetic particles captured after this time period are most likely to be labeled magnetic target objects 140.

In another aspect, the target objects 140 may be labeled using magnetic particles conjugated with a targeting moiety by injecting the conjugated magnetic particles into the biofluid 502 moving through an extracorporeal shunt 500 via an injection port 512, as shown in FIG. 48. Further, the method of labeling the target objects 140 within the extracorporeal shunt 500 may reduce the interaction time between the magnetic particles and the biofluid and other cells not targeted by the magnetic particles, resulting in a reduced risk of toxicity. To further reduce the risk of toxicity, a second, more powerful magnetic array 514 or other means of recapturing the unbound magnetic particles may be included to reclaim the magnetic particles prior to the reintroduction of the biofluid 502 into the vein 510 of the living organism.

In order to verify that the captured magnetic particles are attached to target objects 140, the target objects 140 may be additionally labeled with a contrast agent chosen from an ultrasound contrast agent, a photoacoustic contrast agent, a fluorescent contrast agent, a Raman contrast agent, an MRI contrast agent, a PET contrast agent, or a CT contrast agent, depending on the method of detection used by the in vivo flow cytometer 120. The contrast agents may also be conjugated to a second targeting moiety to facilitate the specific binding of the contrast agent to the target object 140. To avoid interfering with specific binding of the magnetic particles to the target objects 140 the second targeting moiety is chosen to be a different compound from the targeting moiety conjugated to the magnetic particles.

The target objects 140 may be additionally labeled with a contrast agent conjugated with a second targeting moiety by injecting the conjugated contrast agents into the biofluid 500 of the organism. Further, the injection containing the conjugated contrast agents may be administered at a different time than the injection containing the conjugated magnetic particles at the same or different locations. Alternatively, the injection containing the conjugated contrast agents may be administered at a different time than the injection containing the conjugated magnetic particles at the same or different locations. The conjugated contrast agents may also be combined with the conjugated magnetic particles and administered as a single injection.

One or more magnets 110 may be situated in close proximity to the area of interest 132 as described herein after labeling the target objects 140 using the magnetic particles and/or contrast agents in order to manipulate the target objects 140 within the area of interest 132. The magnets 110 may be an integrated component of the in vivo flow cytometer 120, or may be separate components. The magnets 110 or may be supported in a separate item such as a magnetic cuff 300, in a minimally invasive needle device 400 or catheter device, or in an extracorporeal shunt 500, as described herein.

The magnets may be used to manipulate the labeled target objects 140 for a capture period ranging from about 10 minutes to about 2 hours. The length of the capture period may be selected based on one or more of several possible factors including but not limited to the effectiveness of the one or more magnets 110 at capturing the labeled target objects 140 based on magnetic field strength, flow speed of the biofluid, the magnetic dipole of the labeled target object 140, and the amount of time taken for the entire volume of biofluid to pass through the area of interest. The capture period in one particular implementation may be the time for the entire biofluid volume within the organism to pass through the area of interest 132. In this aspect, essentially all labeled target objects within the moving biofluid may be captured and detected within the area of interest 132, resulting in significantly enhanced detection sensitivity.

For example, if the area of interest 132 is a human artery or vein having a diameter ranging from about 2 mm to about 3 mm, the total blood volume of 5 L may circulate through the artery or vein within about one hour, particularly of an artery or vein in close proximity to the heart is chosen and if few alternative flow paths exist between the target artery or vein and the heart. Accordingly, the capture period may be selected to be about one hour in order to capture essentially all labeled target objects 140 circulating in the blood volume within the area of interest 132.

If the one or more magnets 110 are incorporated into the in vivo flow cytometer 120, the organism may be immobilized or otherwise constrained such that the area of interest 132 is kept in close proximity to the one or more magnets 110. If the one or more magnets 110 are included in a magnetic cuff 300, the patient may wear the magnetic cuff independently of the in vivo flow cytometer 120, as illustrated in FIG. 45 and FIG. 46 and described herein, and may further move freely until the captured target objects 140 are detected by the in vivo flow cytometer 120. In various aspects, the magnetic cuff 300 may be removed just prior to the detection of the captured target objects 140, the magnetic cuff 300 may be designed to be worn while the captured target objects 140 are detected by the in vivo flow cytometer 120. For example, if the in vivo flow cytometer 120 is a photoacoustic flow cytometer (PAFC) similar to the PAFC illustrated in FIG. 2B, the magnetic cuff 300 may be designed as illustrated in FIG. 45 to include a channel 102A through the magnet 110C so that an optic fiber 104 (not shown) may be inserted through the magnetic cuff 300A during detection of the captured target objects 140 (not shown) by the in vivo flow cytometer 120 (not shown).

Although various aspects of the method for capturing and detecting target objects 140 have been described in terms of a photoacoustic detection methods, other detection methods may be used either individually or in combination. In various aspects the in vivo flow cytometer 120 may incorporate elements to detect conventional and Raman scattering of the laser pulses by the target objects 140, photothermal effects induced by laser pulses on the target objects 140, and the fluorescence of the target objects 140 induced by absorbed laser pulses.

Once the target objects 140 within the area of interest 132 have been detected by the in vivo flow cytometer 120, the target objects 140 may be removed from the area of interest 132 using known microsurgical techniques and subsequently analyzed using techniques including but not limited to biochemical, histological, or genetic analysis techniques in an aspect. For example, the analysis may be used to identify the phenotype and metastatic activity of captured cells in order to assess the stage of a disease, such as cancer, to provide information to determine an appropriate course of treatment, or to assess the efficacy of a previously-administered course of treatment.

In another aspect, the target objects 140 may be purged from the moving biofluid using the extracorporeal shunt 500 shown in FIG. 48. In this aspect, target objects 140 such as stem circulating tumor cells may be magnetically labeled by injecting magnetic particles conjugated with a targeting moiety into the biofluid 502 via the injection port 512. The targeting moieties specifically bind to the target objects 140 and the attached magnetic particles cause the target objects 140 to be captured within the magnetic field in the area of interest 132 produced by magnets 110G and 110H. Once the target objects 140 are detected within the area of interest 132 by the in vivo flow cytometer 120, the target objects 140 may be removed from the area of interest 132 through a withdrawal port 516. For example, the magnetic purging of the undesirable target objects 140 including but not limited to toxins, high concentration drugs, sickle cells, or tumor cells may be accomplished using a means such as the extracorporeal shunt 500 shown in FIG. 48.

The captured target objects 140 may also be eliminated using non-invasive techniques. For example, if the in vivo flow cytometer 120 is a photoacoustic flow cytometer, the target objects 140 may be eliminated by illuminating the target objects 140 using laser pulses having a pulse wavelength and laser fluence chosen to cause the selective destruction of the target objects 140. Because the absorption of the laser pulses of the target objects 140 is much higher than the surrounding cells and tissue, the laser fluence may be increased beyond the level normally used for detection to levels that selectively damage the target objects 140 without harming the surrounding cells and tissues. Non-limiting examples of target objects 40 that may be selectively eliminated include tumor cells, bacteria, viruses, clots, thromboses, plaques, and combinations thereof.

In various aspects, the method of manipulating and detecting target objects 140 in the moving biofluid 500 of an organism may be used for a variety of medical applications, including but not limited to monitoring of circulating cancer cells for the early diagnosis and treatment of metastasis, inflammations, sepsis, immunodeficiency disorders, strokes, and heart attacks.

EXAMPLES

The following examples illustrate the invention.

Example 1

In Vitro Photothermal (PT) Imaging was Used to Determine the Effect of Laser Energy Levels on Laser-Induced Cell Damage to Blood Cells and Subsequent Cell Viability To determine whether the laser pulses produced during in vivo flow cytometry caused any significant damage to cells or tissues of the organism, the following experiment was conducted. The laser-induced damage threshold of single cells was evaluated as a function of the pumped-laser energy levels at a range of wavelengths using established methods (Zharov and Lapotko 2005, Lapotko and Zharov 2005). In vitro measurements of specific changes in photothermal (PT) images and PT responses from individual cells were used to determine cell damage. During the PT imaging, individual cells were illuminated with a pulse of laser light at a specified energy level and wavelength. After absorbing the energy of the laser pulse, the short-term temperature of the cell increased by as much as 5° C. The laser-induced temperature-dependent refractive heterogeneity in the vicinity of cells caused defocusing of a collinear He—Ne laser probe beam (model 117A; Spectra-Physics, Inc.; 633 nm, 1.4 mW) that illuminated the cell immediately after the initial laser pulse. This defocusing caused a subsequent reduction in the beam's intensity at its center, which was detected with a photodiode (C5658; Hamamatsu Corp.) through a 0.5-mm-diameter pinhole.

PT measurements were performed in vitro using mouse blood cells in suspension on conventional microscope slides. To simulate blood flow conditions, a flow module fitted with a syringe pump-driven system (KD Scientific, Inc.) was used with glass microtubes of different diameters in the range of 30 μm to 4 mm that provided flow velocities of 1-10 cm/sec, which were representative of the diameters and flow rates of animal microvessels.

Individual cells flowing through the glass microtubes were exposed to an 8 ns burst of laser light in a 20-m circular or elongated beam at a variety of wavelengths ranging between 420 nm and 2300 nm. At each wavelength of the initial laser pulse, the laser fluence, defined as the energy contained in the laser beam, was varied between 0.1 mJ/cm$^2$ and 1000 J/cm$^2$. Damage to the cells was determined by assessing the changes in the PT imaging response of cells to laser pulses of increasing fluence. In addition, cell viability after exposure to laser energy was assessed using a conventional trypan blue exclusion assay. Cellular damage was quantified as ED50, the level of laser fluence at which 50% of the measured cells sustained photodamage in vitro. The ED50 values measured for rat red blood cells (RBC), white blood cells (WBC) and K562 blast cells using laser pulses in the visible light spectrum are summarized in Table 1. The ED50 values measured for rat red blood cells (RBC) and white blood cells (WBC) using laser pulses in the near-infrared (NIR) light spectrum are summarized in Table 2.

TABLE 1

Photodamage thresholds for single rat blood cells in the visible light spectrum.

| Wavelength of laser pulse (nm) | Photodamage threshold ED50 (J/cm$^2$) | | |
|---|---|---|---|
| | Rat RBC | Rat WBC | Rat K562 blast cell |
| 417 | 1.5 | 12 | 36 |
| 555 | 5 | 42 | 90 |

TABLE 2

Photodamage thresholds for single rat blood cells in near-IR spectral range.

| Wavelength of laser pulse (nm) | Photodamage threshold ED50 (J/cm$^2$) | |
|---|---|---|
| | Rat RBCS | Rat WBCs |
| 740 | 6.9 | 21.7 |
| 760 | 6.8 | |
| 780 | 17.7 | 152 |
| 800 | 17.5 | 219 |
| 820 | 28.0 | 251 |
| 840 | 43.5 | |
| 860 | 43.8 | 730 |
| 880 | 76.5 | |
| 900 | 69.4 | |
| 920 | 77.7 | 357 |
| 960 | 33.5 | 48.8 |

In the visible spectral range, the relatively strong light-absorbing RBCs sustained cell damage at much lower intensities of laser energy, resulting in ED50 values that were about an order of magnitude lower than the ED50 values measured for WBC or K562 blasts. In the NIR spectral range, where most cells, including RBC, have minimal absorption, cells did not sustain damage until much higher laser energy levels compared to the energy levels at which cellular damage occurred to cells exposed to laser energy in the visible spectrum. The damage thresholds (ED50) for RBCs and WBCs in the spectral range of 860-920 nm were more than one order magnitude higher compared to those in the visible spectrum as shown in Tables 1 and 2.

The results of this experiment established the levels of laser energy at which laser-induced cellular damage may occur. In the NIR spectrum, in which cells exhibited the strongest photoacoustic effects, the damage thresholds are several orders of magnitude above the maximum safety level of approximately 20-100 mJ/cm$^2$ set by ANSI safety standards. Thus, photoacoustic flow cytometry may be performed in vivo with little risk of cell or tissue damage.

Example 2

Prototype In Vivo Photoacoustic Flow Cytometry System Used to Detect Contrast Dye Circulating in Mice The following experiment was conducted to demonstrate the feasibility of in vivo photoacoustic flow cytometry (PAFC) for real-time, quantitative monitoring in the blood circulation of a conventional contrast agent, Lymphazurin. In this experiment, a prototype PAFC system was used to detect Lymphazurin circulating in the blood vessels of a mouse ear.

The prototype PAFC system was built on the platform of an Olympus BX51 microscope (Olympus America, Inc.) and a tunable optical parametric oscillator (OPO) pumped by a Nd:YAG laser (Lotis Ltd., Minsk, Belarus). The general layout of the PAFC system is shown in FIG. 2. Laser pulses had an 8 ns pulse width, a regular repetition rate of 10 Hz with the ability to provide short-term pulses at 50 Hz, and a wavelength in the range of 420-2,300 nm. Laser energy was directed to the blood vessels using a conventional lens, or an optical fiber. PA waves emitted by the cells were detected by ultrasound transducers (unfocused Panametrics model XMS-310, 10 MHz; focused cylindrical Panametrics model V312-SM, 10 MHz, focused lengths of 6 mm, 12 mm, and 55 mm; and customized resonance transducers), and the ultrasound transducer outputs were conditioned by an amplifier (Panametrics model 5662, bandwidth 50 kHz-5 MHz; Panametrics model 5678, bandwidth 50 kHz-40 MHz; customized amplifiers with adjustable high and low frequency boundaries in the range to 50-200 KHz and 1-20 MHz, respectively; resonance bandwidth of 0.3-1.0 MHz). The amplifier output signals were recorded with a Boxcar data acquisition system (Stanford Research Systems, Inc.) and a Tektronix TDS 3032B oscilloscope, and were analyzed using standard and customized software. The Boxcar data acquisition technique provided averaging of the PA waves from cells in the blood vessels, and discriminated the PA waves from background signals from surrounding tissue on the basis of the difference in time delays between the two signals. The signals from the oscilloscope screen were recorded with a digital camera (Sony, Inc.) and video camera (JVC, Inc.).

A high-speed computer (Dell Precision 690 workstation with a quadcore processor, 4 GB of RAM and Windows Vista 64 bit operating system) and digitizer (National Instruments PCI-5124 high speed digitizer) were used to acquire the PA signal data from the PAFC device. National Instruments software (Labview Version 8.5 and NI Scope Version 3.4) was used to control the digitizer and create a data logging user interface. The hardware and supporting program were capable of collecting data at a rate of 200 megasamples per second, corresponding to a time resolution of 5 ns.

A laser beam with a circular cross section and a diameter of approximately 50 m, a wavelength of 650 nm, and a fluence of 35 mJ/cm$^2$ was used to illuminate the flow in the blood vessels. The 650 nm wavelength used was near the wavelength of maximum absorption of Lymphazurin, the contrast dye used in this experiment, and well separated from the wavelengths of maximum absorption of other blood components. Navigation of the laser beams was controlled with transmission digital microscopy (TDM) at a resolution of approximately 300 nm using a Cascade 650 CCD camera (Photometrics).

All in vivo experiments described below were performed using a nude mouse ear model. PAFC detection was performed using relatively transparent, 270 μm thick mouse ears with well-distinguished blood microvessels. The ear blood vessels examined were located at a depth of 30-100 μm, had diameters in the range of 30-50 μm, and blood velocities of 1-5 mm/sec. After undergoing anesthesia using ketamine/xylazine at a dosage of 50/10 mg/kg, each mouse was placed on a customized heated microscope stage, together with a topical application of warm water, which provided acoustic matching between the transducer and mouse ear.

The contrast dye used for the experiments described below was Lymphazurin, a contrast agent commonly used for the delineation of lymphatic vessels. A 1% solution of Lymphazurin (Isosulfan Blue) was purchased from Ben Venue Labs Inc., USA.

After anaesthetizing each mouse and placing the mouse on the microscope stage as described above, 200 µl of a 1% aqueous solution of Lymphazurin was injected into the tail vein of the mouse.

Figure 3:
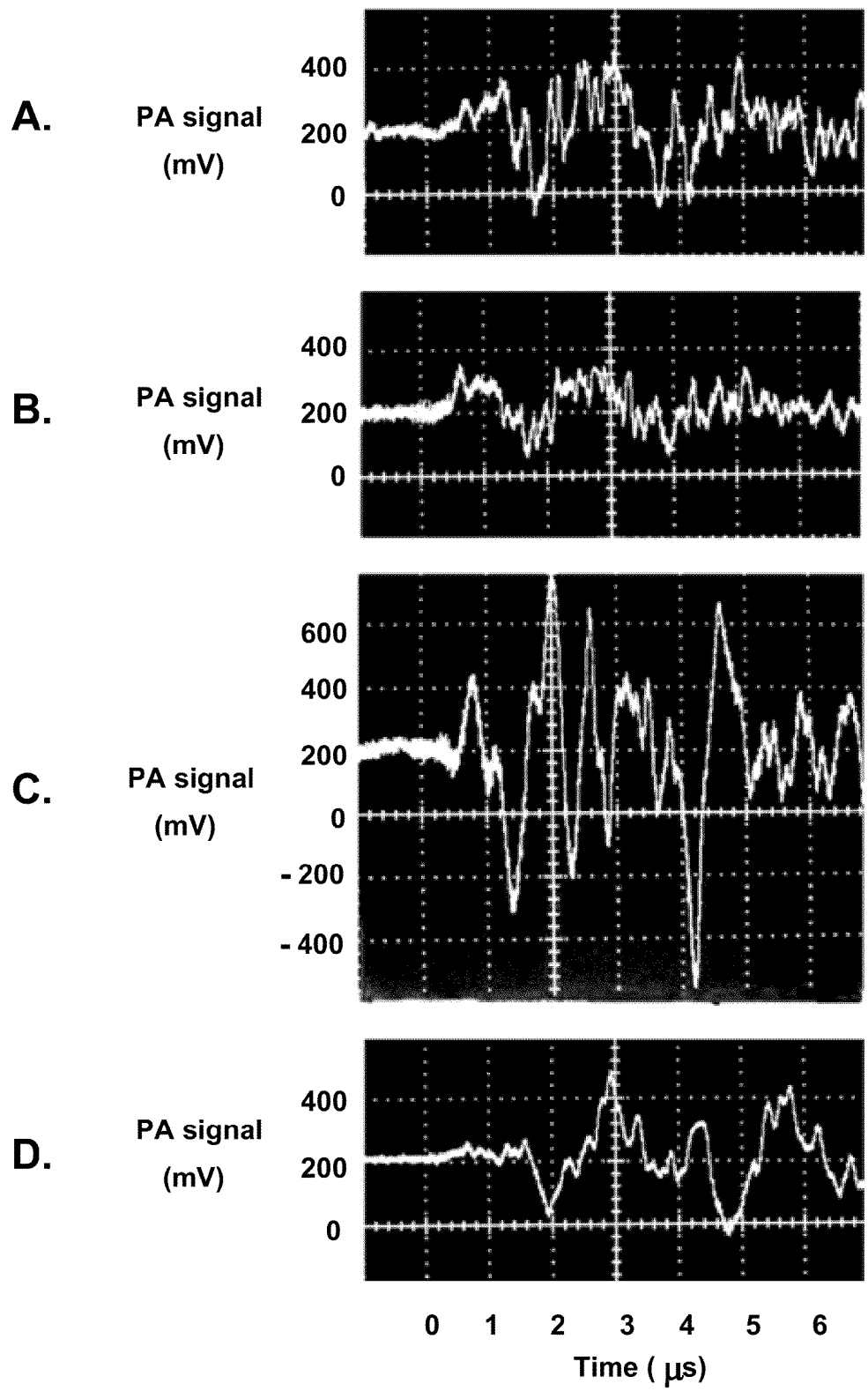
FIG. 3 shows the oscilloscope trace recordings of PA signals: (A) from blood flow in a rat ear vessel with diameter of 50 µm, (B) from skin surrounding a rat ear vessel before dye injection, (C) from blood flow in a rat ear vessel 5 min after the injection of Lymphazurin, and (D) from the skin surrounding a rat ear vessel measured 20 min after dye injection.

PAFC measurements of the circulating dye were performed at a laser pulse wavelength of 650 nm. FIG. 3 shows oscilloscope traces of PAFC signals from the blood vessels and surrounding tissues in the rat ear before and after injection with Lymphazurin. Prior to injection, the maximum 240 mV PA signals from blood vessels, shown in FIG. 3A, were approximately 1.5 times higher than the 160 mV PA background signals from surrounding tissue, shown in FIG. 3B. Maximum PA signals from the blood vessel after dye administration, shown in FIG. 3C, increased approximately three-fold over pre-injection levels. The PA signals from tissue around vessels after dye injections, shown in FIG. 3D, gradually increased approximately 2.5-fold over pre-injection levels during the first 15-20 minutes, and then remained relatively constant for the next 1-1.5 hours, possibly due to the passage of the Lymphazurin out of the blood vessels and into nearby lymphatic vessels.

Figure 4:
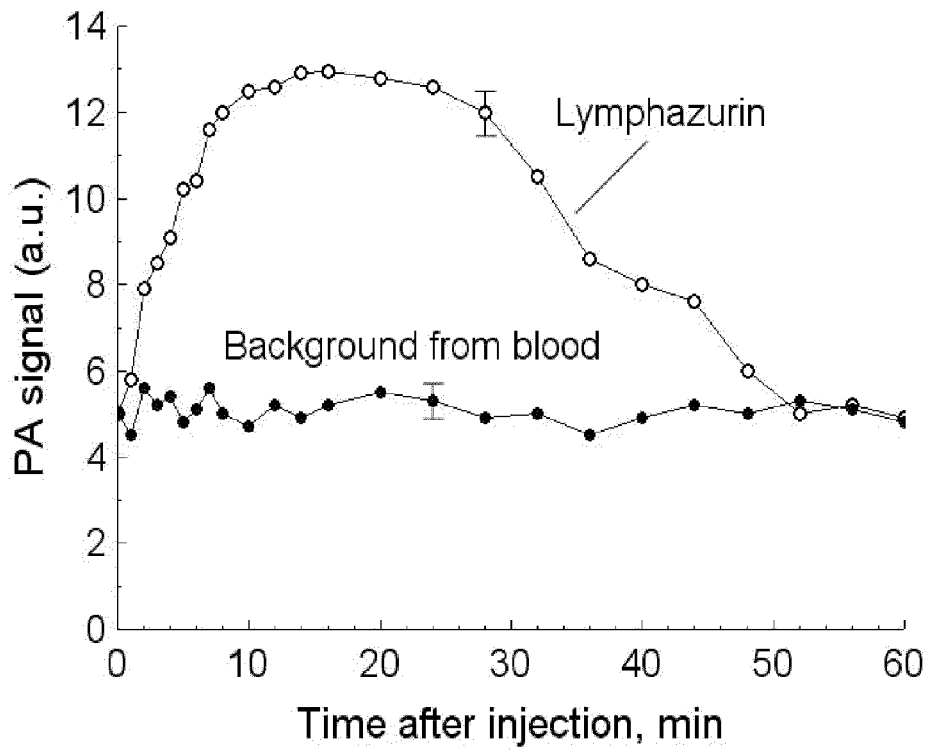
FIG. 4 shows the PA signal detected from the monitoring of the blood flow in a 50-µm rat ear microvessel with diameter after intravenous injection of Lymphazurin dye in the tail vein.

FIG. 4 summarizes the maximum PAFC signals from Lymphazurin compared to background PAFC signals from the blood vessels, observed for one hour after the injection of Lymphazurin. As shown in FIG. 4, continuous monitoring of PA signals from the ear blood microvessels revealed a rapid appearance of Lymphazurin in the blood flow within a few minutes after injection, followed by clearance of Lymphazurin from the blood over the next 50 minutes.

The results of this experiment demonstrated that the prototype PAFC system exhibited sufficient sensitivity to detect the presence of ultrasonic contrast dyes in circulation.

Example 3

Prototype In Vivo Photoacoustic Flow Cytometry System Used to Detect Nanoparticles Circulating in Rats To demonstrate the sensitivity of a prototype in vivo photoacoustic flow cytometry (PAFC) system described in Example 2 an experiment was conducted using the prototype PAFC system to detect nanoparticles intravenously injected into the tail veins of rats.

The in vivo measurements in this experiment were performed using the rat mesentery model. The rat (White Fisher, F344) was anesthetized using ketamine/xylazine at a dosage of 60/15 mg/kg, and the mesentery was exposed and placed on a heated microscope stage, and bathed in Ringer's solution at a temperature of 37° C. and a pH of 7.4. The mesentery consisted of transparent connective tissue of 7-15 µm thickness, and a single layer of blood and lymph microvessels.

The nanoparticles used in this experiment were gold nanorods (GNR), obtained from the Laboratory of Nanoscale Biosensors at the Institute of Biochemistry and Physiology of Plants and Microorganisms in Saratov, Russia. On the basis of TEM and dynamic light scattering analyses, the GNR were estimated to be approximately 15 nm in diameter and approximately 45 nm in length on average. The nanoparticles were used either uncoated or functionalized using thiol-modified polyethylene glycol (PEG) (Liao and Hafner 2005).

A 250-µL suspension of GNR with a concentration of $10^{10}$ particles/ml was injected into the tail veins of three rats, followed by the continuous monitoring of PA signals measured from 50-µm diameter blood vessels in the rat mesentery using the PAFC system described in Example 2. PAFC measurements were taken using a laser fluence of 100 mJ/cm$^2$, a laser beam diameter of approximately 50 µm, and a laser wavelength of 830 nm, near the maximum absorption of the GNR.

Figure 5:
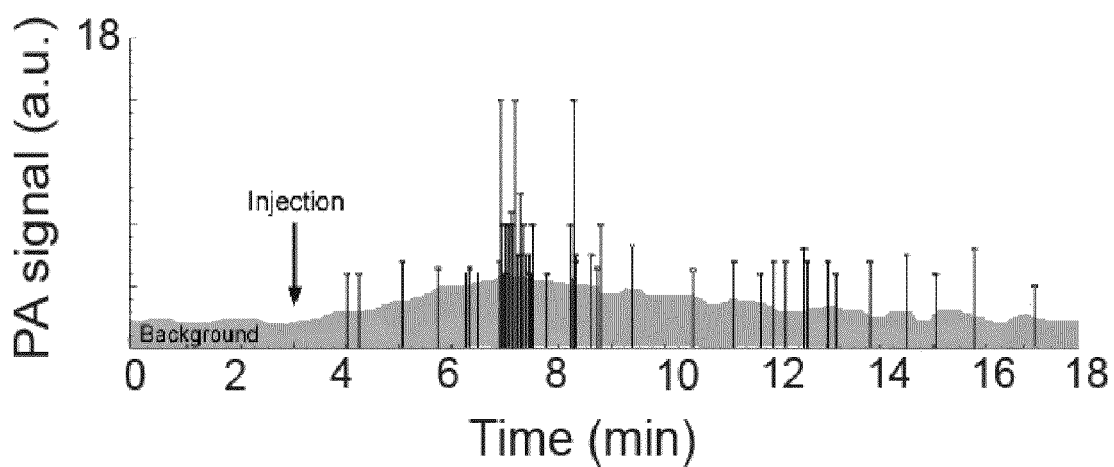
FIG. 5 shows the PA signal from circulating GNR in 50-µm rat mesentery microvessels as a function of post-injection time.

Uncoated GNR were rapidly cleared from the blood circulation within 1-3 minutes preferentially by the reticuloendothelial system (data not shown). After PEGylated GNR injection, strong fluctuating PA signals appeared with amplitudes significantly exceeding the PA background signals from blood vessels within the first minute and continued for 14-25 minutes, depending on the individual animal. In addition, the PA background signal from the blood vessel increased approximately 1.5-2 times above the pre-injection background levels, reaching a maximum level between four and nine minutes after injection, as shown in FIG. 5.

Figure 6:
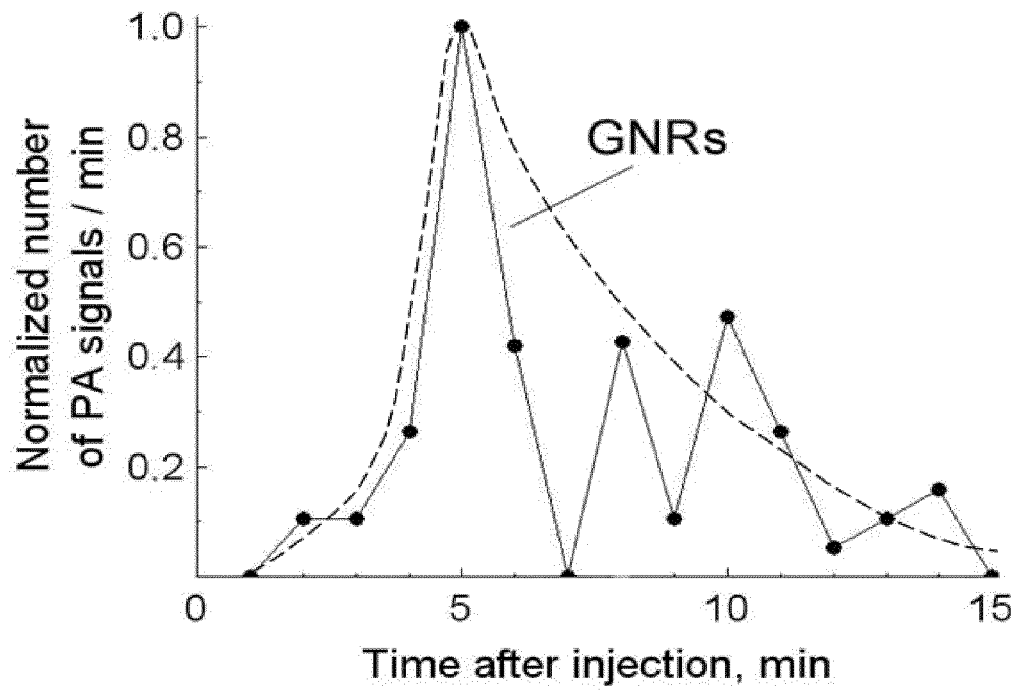
FIG. 6 is a graph of the normalized number of circulating GNR in blood microvessels of the rat mesentery as a function of post-injection time and a dashed curve showing averaged data (N=3).

The averaged PA signals from three animals, measured for 15 minutes after injection with GNR suspensions, are summarized in FIG. 6. The maximum rate of individual PA signals per minute, representing the number of GNR in circulation, was achieved approximately 5 minutes after injection, with a gradual decrease in the signal rate over the next 10 minutes.

The results of this experiment demonstrated that the prototype PAFC system possessed sufficient spatial and temporal resolution to continuously monitor the circulation of nanoparticles as small as 15 nm in diameter. In addition, the prototype PAFC system was sufficiently sensitive to track fluctuations of the concentration of circulating particles from the time that they were injected to the time that the particles were cleared from circulation.

Example 4

Prototype In Vivo Photoacoustic Flow Cytometry System Used to Detect *S. aureus* Bacteria Circulating in Mice To demonstrate the ability of the prototype photoacoustic flow cytometry (PAFC) system to detect bacteria cells in vivo under biological conditions, the following experiment was conducted. The prototype PAFC system, previously described in Example 2, was used to measure *S. aureus* bacteria in the circulation of nude mice.

The mouse ear model described in Example 2 was used for all measurements of circulating bacteria in the experiment. Because the endogenous light absorption of *S. aureus* bacteria was relatively weak compared to the absorption of other blood components in the NIR spectral range, the bacteria were labeled with the NIR-absorbing contrast substances indocyanine green dye (ICG) and carbon nanotubes (CNT), due to their relatively high labeling efficiency and low toxicity (data not shown).

The *S. aureus* bacterium strain designated UAMS-1 was isolated from a patient with osteomyelitis at the McClellan Veterans Hospital in Little Rock, Ark., USA. The strain was deposited with the American Type Culture Collection and is available as strain ATCC 49230. UAMS-1 was cultured in tryptic soy broth and grown aerobically for 16 h at 37° C. Cells were harvested by centrifugation, resuspended in sterile PBS and incubated with Indocyanine Green (ICG) dye (Akom Inc., USA) or carbon nanotubes (CNT) as described below.

Before incubation, ICG dye was filtered through a 0.22 µm pore size filter. A 150-µl aliquot of bacteria in suspension was incubated with 375 µg of ICG in 150 µl of solution for 30 min at room temperature and then for 2 h at 37° C. Labeled bacteria were centrifuged at 5,000 rpm for 3 min and the resulting pellet was resuspended in PBS.

Single-walled and multi-walled carbon nanotubes (CNT) were purchased from Carbon Nanotechnologies Inc. (Houston, Tex.) and Nano-lab Inc. (Newton, Mass.), respectively. The CNT samples used in this study were processed using known methods (Kim et al. 2006). The average length and diameter of the single-walled CNT were 186 nm and 1.7 nm respectively, and the average length and diameter of the multi-walled CNT were 376 nm and 19.0 nm respectively.

CNT solutions were treated with five cycles of 1.5 min of ultrasound at a power of 3 W followed by 0.5 min of rest, for a total of 10 minutes of interrupted ultrasound. A 150-µl aliquot of bacteria in suspension was incubated with 150 µl of CNT solution for 30 minutes at room temperature followed by 2 additional hours of incubation at room temperature. Labeled bacteria were centrifuged at 10,000 rpm for 5 min and the resulting pellet was resuspended in PBS.

Labeled 100-µl suspensions of *S. aureus* bacteria at a concentration of $5 \times 10^5$ cells/ml were injected into the mouse's tail vein, and the clearance of the labeled bacteria was monitored using PAFC measurements taken from 50-µm diameter microvessels in the ears of mice. Laser energy was delivered at a wavelength of 805 nm for the *S. aureus* that was labeled with ICG, and at a wavelength of 850 nm for the *S. aureus* that was labeled with CNT. For both label types, the laser energy was delivered at a beam diameter of approximately 50 µm and at a fluence ranging between 20 and 50 mJ/cm$^2$.

Figure 7:
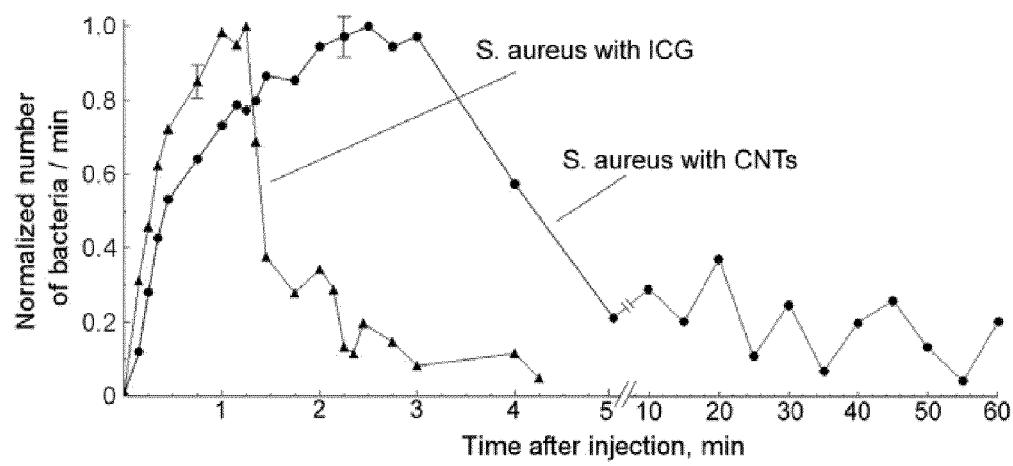
FIG. 7 is a graph of the normalized number of circulating *S. aureus* in blood microvessels of the mouse ear as a function of post-injection time, for bacteria labeled using two different contrast substances, ICG dye and CNT.

*S. aureus* bacteria labeled with ICG and CNT contrast substances yielded similar results, summarized in FIG. 7. After injection of labeled *S. aureus*, PAFC detected a rapid appearance of bacteria in the ear blood microvessels within the first minute, followed by a steady elimination of the bacteria from the blood circulation over the next 3-5 minutes. Periodic PAFC monitoring of mice blood vessels over the next few days revealed that very rare bacteria labeled with CNT or possibly unattached CNT continued to appear at an average rate of one PA signal every three minutes, and the labeled bacteria or CNT was not completely cleared from circulation until about 60 hrs after the initial injection (data not shown).

The results of this experiment established the feasibility of PAFC for the in vivo monitoring of individual cells in the circulatory systems of living organisms. Using appropriate contrast enhancement substances, the laser fluence required for effective detection of cells in circulation was well below the threshold levels for laser-induced cell damage.

Example 5

Prototype In Vivo Photoacoustic Flow Cytometry System Used to Detect *E. coli* Bacteria Circulating in Mice To demonstrate the ability of the prototype photoacoustic flow cytometry (PAFC) system to detect bacteria cells in vivo under biological conditions, the following experiment was conducted. The prototype PAFC system, previously described in Example 2, was used to detect the bacteria *E. coli* strain K12, in the circulation of nude mice.

The mouse ear model described in Example 2 was used for all measurements of circulating bacteria in the experiments described below. Because the endogenous light absorption of *E. coli* bacteria was relatively weak compared to the absorption of other blood components in the NIR spectral range, the bacteria were labeled with NIR-absorbing carbon nanotubes (CNT).

*E. coli* K12 strain was obtained from the American Type Culture Collection (Rockville, Md.) and maintained in Luria-Bertani (LB) medium, a solution consisting of 1% tryptone, 0.5% yeast extract, and 0.5% NaCl at a pH of 7. A 100-µl aliquot of *E. coli* in PBS was incubated with 100 µl of the CNT solution as described in Example 4 for 60 min at room temperature.

Figure 8:
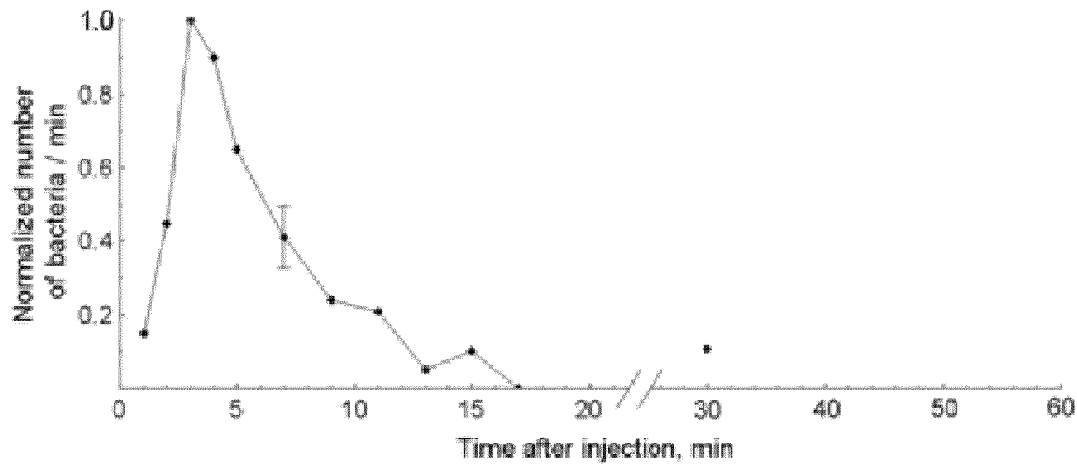
FIG. 8 is a graph of the normalized number of circulating *E. coli* in blood microvessels of the mouse ear as a function of post-injection time.

100-µl suspensions of CNT-labeled *E. coli* bacteria at a concentration of $5 \times 10^5$ cells/ml were injected into the mouse's tail vein, and the clearance of the labeled bacteria was monitored using PAFC measurements taken from 50-µm diameter microvessels in the ears of mice. Laser energy was delivered at a wavelength of 850 nm, a beam diameter of approximately 50 µm and at a laser fluence of 100 mJ/cm$^2$. PAFC measurements, summarized in FIG. 8, detected a rapid appearance of the bacteria in circulation after injection, and the bacterial concentrations in the blood decreased exponentially over the next 15-17 minutes.

The results of this experiment confirmed the feasibility of PAFC for the in vivo monitoring of individual cells in the circulatory systems of living organisms. The laser fluence required for effective detection of *E. coli* cells in circulation was well below threshold levels for laser-induced cell damage.

Example 6

In Vivo PAFC Used to Detect Circulating Exogenous Melanoma Cells

To demonstrate the ability to use in vivo PAFC to detect unlabeled melanoma cells in circulation with extremely high sensitivity through skin cells with varying levels of melanin pigmentation, the following experiment was conducted.

B16F10 cultured mouse melanoma cells (ATCC, Rockville, Md.) were used in this experiment. The cells were maintained using standard procedures (Ara et al. 1990, Weight et al. 2006, Zharov et al. 2006), including serial passage in phenol-free RPMI 1640 medium (Invitrogen, Carlsbad, Calif.) supplemented with 10% fetal bovine serum (FBS, Invitrogen). For comparison to the detection of unlabelled melanoma cells, the endogenous cell absorption was increased by staining with ICG (Akorn Inc., USA), a strongly absorbent dye in the NIR range, for 30 min at 37° C. and in the presence of 5% $CO_2$. No toxicity was observed after labeling as assessed using the trypan blue exclusion assay (data not shown).

Figure 9:
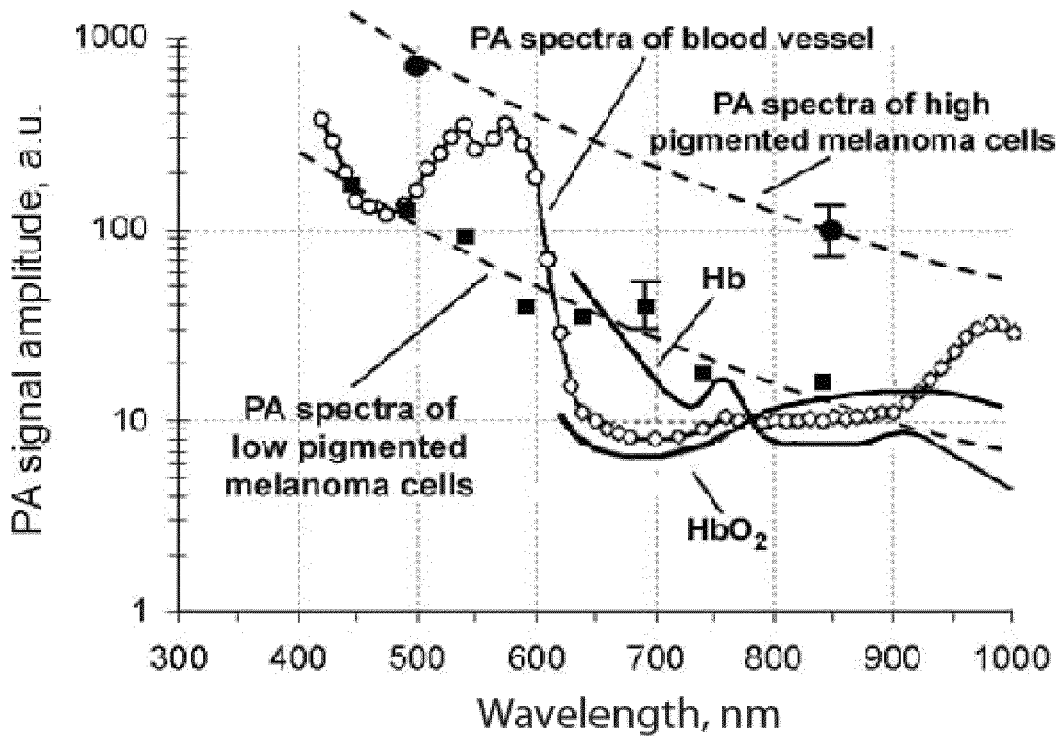
FIG. 9 shows the PA spectra of 50-µm diameter veins in the mouse ear (empty circles), conventional absorption spectra of the B16F10 mouse melanoma cells with strong pigmentation (upper dashed curve) and weak pigmentation (lower dashed curve), spectra normalized using PA signals for the single mouse melanoma cells with strong pigmentation (black circles) and weak pigmentation (black squares), and absorption spectra for pure Hb and $HbO_2$ (fragments of solid curves in the spectral range 630-850 nm).

In vivo measurements of melanoma cells used the PAFC system previously described in Example 2 with a laser wavelength of 850 nm and a laser fluence of 80 mJ/cm$^2$. This wavelength falls within a region in which the absorbance of melanoma cells is relatively high compared to the absorbance of hemoglobin, a major component of blood, as determined by in vitro measurements summarized in FIG. 9.

To estimate the influence of endogenous skin melanin on PAFC detection limits, Harlan Sprague mice, strain: NIH-BG-NU-XID were used in this experiment. Female mice of this strain possess high levels skin pigmentation between 8 and 10 weeks of age. Mice were anaesthetized and placed on the heated microscope stage as previously described in Example 2.

Figure 10:
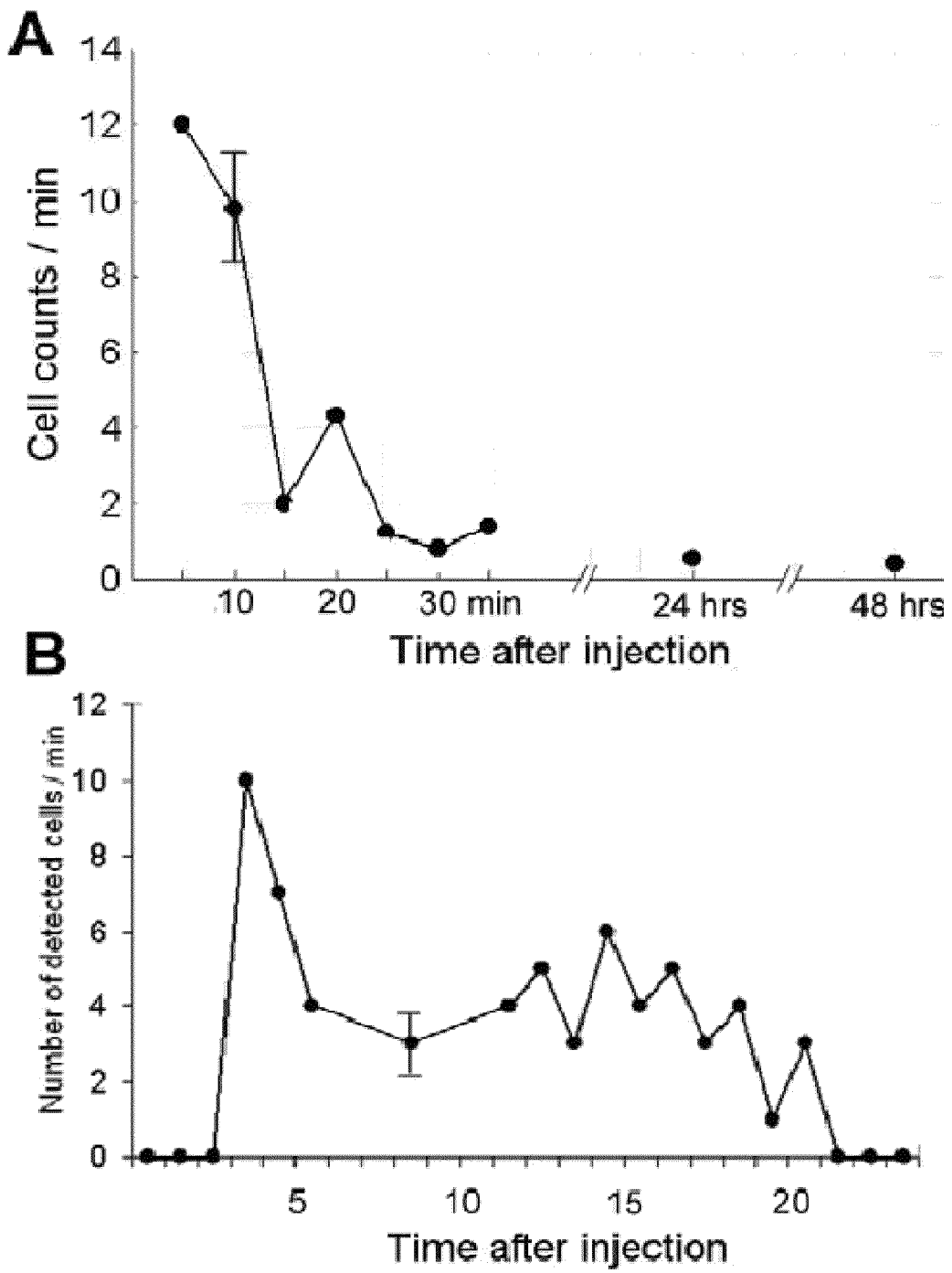
FIG. 10 is a graph showing the frequencies of circulating mouse melanoma cells (B16F10) detected with label-free PAFC in 50-µm mouse ear veins, with a flow velocity of 5 mm/s, in mice with low (A) and high (B) melanin pigmentation as a function of post-injection time.

A 200-µl volume of saline solution containing approximately $10^5$ mouse melanoma cells was injected into the mouse circulatory system through a tail vein and then monitored using the PAFC system. The number of melanoma cells per minute detected using PAFC for melanoma cells after injection are summarized in FIG. 10 for melanoma cells with low melanin content (FIG. 10A) and for melanoma cells with high melanin content (FIG. 10B). In the first 5 minutes of PA detection following intravenous injection of cultured mouse melanoma cells, 600±120 PA signals (representing melanoma cells) per hour were observed, and the rate of detection of melanoma cells steadily decreased over the subsequent 20-30 min. Approximately 20 cells/hour and 4 cells/hour were detected after 24 h and 48 h of monitoring, respectively. The initial PA signal rate after the injection of melanoma cells stained with ICG contrast enhancement substances was 720±105 cells/hour (data not shown). Assuming that all stained melanoma cells were detected by in vivo PAFC, 82.4% of the unlabelled melanoma cells in circulation were detected by in vivo PAFC measurements.

The results of this experiment demonstrated the ability of in vivo PAFC to detect and monitor the appearance and progression of metastatic melanoma cells in circulation non-invasively.

Example 7

In Vivo PAFC was Used to Detect Circulating Spontaneous Metastatic Cells During Tumor Progression An experiment was conducted to determine the ability of in vivo PAFC to detect relatively scarce endogenous metastatic melanoma cells circulating in lymph vessels. The PAFC system described in Example 2 was used to monitor endogenous metastatic melanoma cells in mice. The laser characteristics used in this experiment are identical to those described in Example 5.

Nude mice were anaesthetized and placed on the heated microscope stage as previously described in Example 2. The ear blood vessels under examination were located 50-100 µm deep and had diameters of 35-50 µm with blood velocities of 3-7 mm/sec. To increase the probability of detection of rare metastatic cells, blood vessels with relatively large diameters of 150-300 µm and flow velocities up to 10-30 mm/s in the skin of the abdominal wall were examined using a customized skin fold chamber.

50-µl suspensions containing $10^6$ B16F10 cultured mouse melanoma cells (ATCC, Rockville, Md.) were subcutaneously injected into nude mice. Melanoma tumors subsequently formed in the ears of the mice and in the skin on the backs of the mice. PAFC was performed on ear and abdominal blood vessels to monitor the circulatory system for the appearance of metastatic cells, and PA mapping, described below, was used to monitor the growth of tumors.

During ear tumor development, individual or groups of melanoma cells were first detected in the skin area close to the tumor site on the sixth day following tumor inoculation using PA mapping measurements. PA mapping measurements utilized PA signals derived by scanning a focused laser beam with diameter of 10 µm across ear. Metastatic cells first appeared in ear microvessels near the tumor on the twentieth day after inoculation at a rate of 12±5 cells/hour (data not shown). Surprisingly, during the same time period, no melanoma cells had yet been detected in the abdominal skin blood vessels. 25 days after inoculation, the average count of melanoma cells detected in the ear veins increased to 55±15 cells/hour, and at this same time, melanoma cells were detected in abdominal wall skin vessels at a rate of 120±32 cells/hour. Thirty days after inoculation, the detection rate decreased to 30±10 cells/hour in the abdominal vessel, which may be attributed to inhibition of metastatic cell production in the primary tumor. PA mapping of selected tissue and organs revealed multiple micrometastases in cervical and mesenteric lymph nodes, as well as in lung and liver tissues.

PAFC measurements of the nude mouse back tumor model revealed the appearance of metastatic melanoma in abdominal skin blood vessels close to the tumor site on day 5, much earlier than in the tumor ear model. This indicates a much greater likelihood of detecting the initial metastatic process in the vicinity of the primary tumor.

Thirty days after tumor inoculation, the average concentration of melanoma cells was 150±39 cells/ml, corresponding to a circulating rate of approximately 4-10 cells/min in a 50-mm blood vessel and a flow velocity of 5 mm/s. The ultimate PAFC threshold sensitivity of the nude mouse back tumor model was estimated as 1 cell/ml. This circulating rate corresponded to an incidence of approximately one melanoma cell among 100 million normal blood cells.

The results of this experiment indicated that in vivo PAFC and PA mapping were sensitive methods with which to monitor the development of metastasized melanoma cells non-invasively, with high sensitivity and accuracy.

Example 8

In Vivo PAFC was Used to Detect Spontaneous Metastatic Cells in Lymphatic Vessels During Tumor Progression To determine the feasibility of detecting individual metastatic cells in lymph flow, the following experiment was conducted. A photoacoustic flow cytometer (PAFC) was used to monitor lymph flow for the presence of WBC, RBC, and metastatic melanoma cells.

The animal models used in this experiment were nu/nu nude mice, weighing 20-25 g (Harlan Sprague-Dawley). PAFC measurements were taken using the lymphatic vessels in the ears using a heated platform as described in Example 2. Melanoma tumors in the ear and back skin of the mice were induced by the subcutaneous injection of B16F10 mouse melanoma cells as described in Example 6.

To locate the lymphatic vessels in the mouse ear, a PA mapping process using a PA contrast agent was used. Ethylene blue (EB) dye, commonly used for lymphatic research, was injected into the lymphatic vessel walls. A 639 nm laser beam was then used to illuminate the lymphatic vessel at a wavelength of 639 nm, corresponding to the maximum absorption of EB dye, and the resulting PA signal emitted by the EB dye was monitored. The position of the laser beam on a lymph vessel was fixed when the PA signal amplitude reached its maximum at the laser wavelength of 639 nm.

Figure 11:
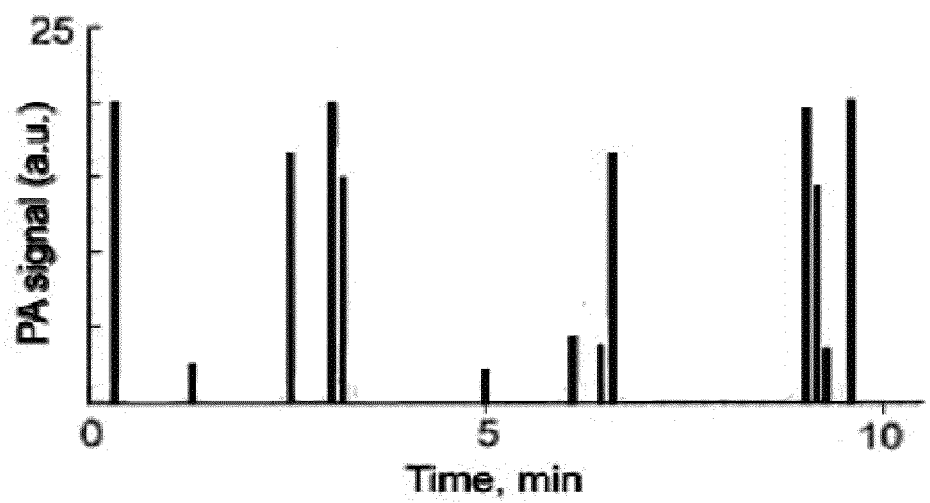
FIG. 11 is a summary of the PA signal rates from single melanoma cells detected in a mouse ear lymph microvessel 5 days after tumor inoculation.

In vivo PAFC detection of unlabeled melanoma cells relied on melanin as an intrinsic cell marker, as in Example 7. Melanoma cells were detected using a laser wavelength of 850 nm, a laser fluence of 35 mJ/cm$^2$, and a laser beam diameter of approximately 50 µm. In mice with induced skin melanomas, metastatic cells were observed to appear in a lymphatic vessel of the mouse's ear on the fifth day after inoculation at a rate of 1.2±0.5 cells/min, which steadily increased over the course of 2 weeks (data not shown). In mice with a melanoma tumor in the ear, melanoma cells appeared in skin lymphatics 20 days after inoculation. 30 days after inoculation strong PA signals detected the presence of metastatic melanoma cells in the sentinel lymph nodes, which was later confirmed by histology (data not shown). FIG. 11 shows the PA signals detected from single metastatic melanocytes circulating in the lymphatic vessel in the mouse ear five days after tumor inoculation.

The results of this experiment demonstrated the feasibility of detecting relatively scarce metastatic melanoma cells circulating in the lymphatic system using in vivo PAFC techniques, with high sensitivity and accuracy.

Example 9

In Vivo PAFC was Used to Detect Red Blood Cells and Lymphocytes Simultaneously Circulating in Lymph Vessels To determine the feasibility of detecting unlabeled individual cells of different types circulating in lymph flow, the following experiment was conducted. A photoacoustic flow cytometer (PAFC) was used to monitor lymph flow for the presence of red blood cells and lymphocytes.

The animal models used in this experiment were 150-200 g rats (Harlan Sprague-Dawley). PAFC measurements were taken using lymphatic vessels in the mesentery of the rat, using the method described in Example 3. Lymphatic vessels were located, and the laser was focused on the lymphatic vessel using the methods described in Example 8.

Spectroscopic studies in vitro revealed that PA signals from lymphocytes reached maximal amplitude in the visible-spectral range near 550 nm, associated with cytochrome c acting as an intrinsic absorption marker (data not shown). Background PA signals from vessels and surrounding tissues were approximately 4-6-fold less than from single lymphocytes at this wavelength due to the low level of background absorption and laser focusing effects.

Figure 12:
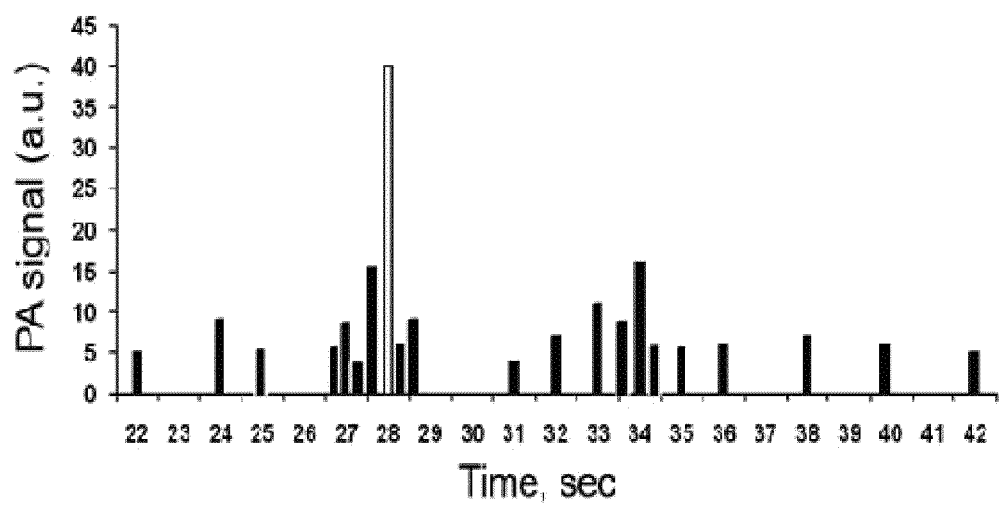
FIG. 12 is a summary of the PA signal rates from a single RBC (white bar) and lymphocytes (black bars) detected by PAFC in the lymph flow of rat mesentery.

The in vitro PAFC system described in Example 2 was used to detect circulating cells in the lymphatic vessels of the rat mesentery. The laser used in the PAFC system had a wavelength of 550 nm and a fluence of 100 mJ/cm$^2$, and a circular beam diameter of approximately 50 µm. The cell detection rate obtained in lymphatic vessels was 60±12 cells/min. A graph showing the PA signals detected by the PAFC system in a rat mesentery lymphatic vessel is shown in FIG. 12. Lymphocyte heterogeneity resulted in 2-2.5-fold fluctuations in PA signal amplitude from cell to cell. A small fraction of the detected cells had strong PA signal amplitudes exceeding those of the lymphocyte signals by a factor of 10 to 20-fold. One such strong PA signal is shown as a white bar in FIG. 12 at 28 seconds. Subsequent spectral and imaging analysis identified rare single red blood cells (RBCs) as the sources of these excessively strong PA signals.

The results of this experiment demonstrated that the in vivo PAFC system possessed sufficient sensitivity and accuracy for the simultaneous detection of red blood cells and lymphocytes circulating in the lymphatic vesicles.

Example 10

In Vivo Two-Wavelength PAFC was Used to Discriminate Between 3 Different Exogenously Labeled Cell Types in Circulation within Lymph Vessels To demonstrate the ability of the photoacoustic flow cytometry (PAFC) system to detect cells using more than one wavelength of laser light, the following experiment was conducted. In this experiment, a PAFC system was used to detect exogenous blood cells that were labeled with three different nanoparticles, while circulating in blood vessels (data not shown) and in lymphatic vessels. The PAFC system detected the cells by illuminating the cells with laser pulses of two different wavelengths in the near-infrared (NIR) spectrum.

A PAFC system similar to that described in Example 2 was used to detect the circulating cells. However, in the PAFC system used in this experiment, the laser of the PAFC system pulsed light at two different wavelengths, corresponding to the wavelengths of maximum absorption for two of the nanoparticles used to label the cells. The first laser pulse was at a wavelength of 865 nm, a laser fluence of 35 mJ/cm$^2$, and pulse duration of 8 ns. 10 s after the end of the first laser pulse, a second laser pulse was delivered at a wavelength of 639 nm, a laser fluence of 25 mJ/cm$^2$, and pulse duration of 12 ns. The paired laser pulses were repeated at a frequency of 10 Hz.

The animal models used in this experiment were nu/nu nude mice, weighing 20-25 g (Harlan Sprague-Dawley). PAFC measurements were taken using lymphatic vessels in the mesentery of the mouse, using the methods described in Example 3. Lymphatic vessels were located, and the laser was focused on the lymphatic vessel using the methods described in Example 8.

Normal fresh blood cells were obtained from heparinized whole-blood samples of donor mice after terminal blood collection. Red blood cells were isolated by simple centrifugation, and lymphocytes were isolated by Histopaque (Sigma-Aldrich) density gradient centrifugation as recommended by the supplier.

The nanoparticles used to label the various blood cells used in this experiment were gold nanorods (GNR) and gold nanoshells (GNS), provided by The Laboratory of Nanoscale Biosensors at the Institute of Biochemistry and Physiology of Plants and Microorganisms in Saratov, Russia. The GNR had an average diameter of 16 nm, an average length of 40 nm, and a relatively narrow absorption band of 660±50 nm. The GNS had an average diameter of 100 nm, and a maximum absorption near 860 nm. Both GNR and GNS were coated with polyethylene glycol in the process described in Example 3. Single-walled CNT with an average length of 186 nm and an average diameter of 1.7 nm were purchased from Carbon Nanotechnologies Inc. CNT absorb laser energy over a wide range of wavelengths with an efficiency that monotonically decreases as wavelength increases. All particles were in suspension at a concentration of about $10^{10}$ nanoparticles/ml.

Live neutrophils were labeled with the GNS, live necrotic lymphocytes were labeled with the GNR and apoptotic lymphocytes were labeled with the CNT. The cells were labeled by incubating 100-µl aliquots of each cell type in phosphate-buffered saline with 100 µl of CNT, GNR, or GNS for 15 min at room temperature.

The labeled cells, mixed in approximately equal proportions, were intravenously injected into the tail vein of the mouse. After 6 h, mesenteric lymphatics were illuminated with two laser pulses at wavelengths of 865 nm and 639 nm as described above. PA signals at a rate of 1-3 signals/min were detected at this time.

Figure 13:
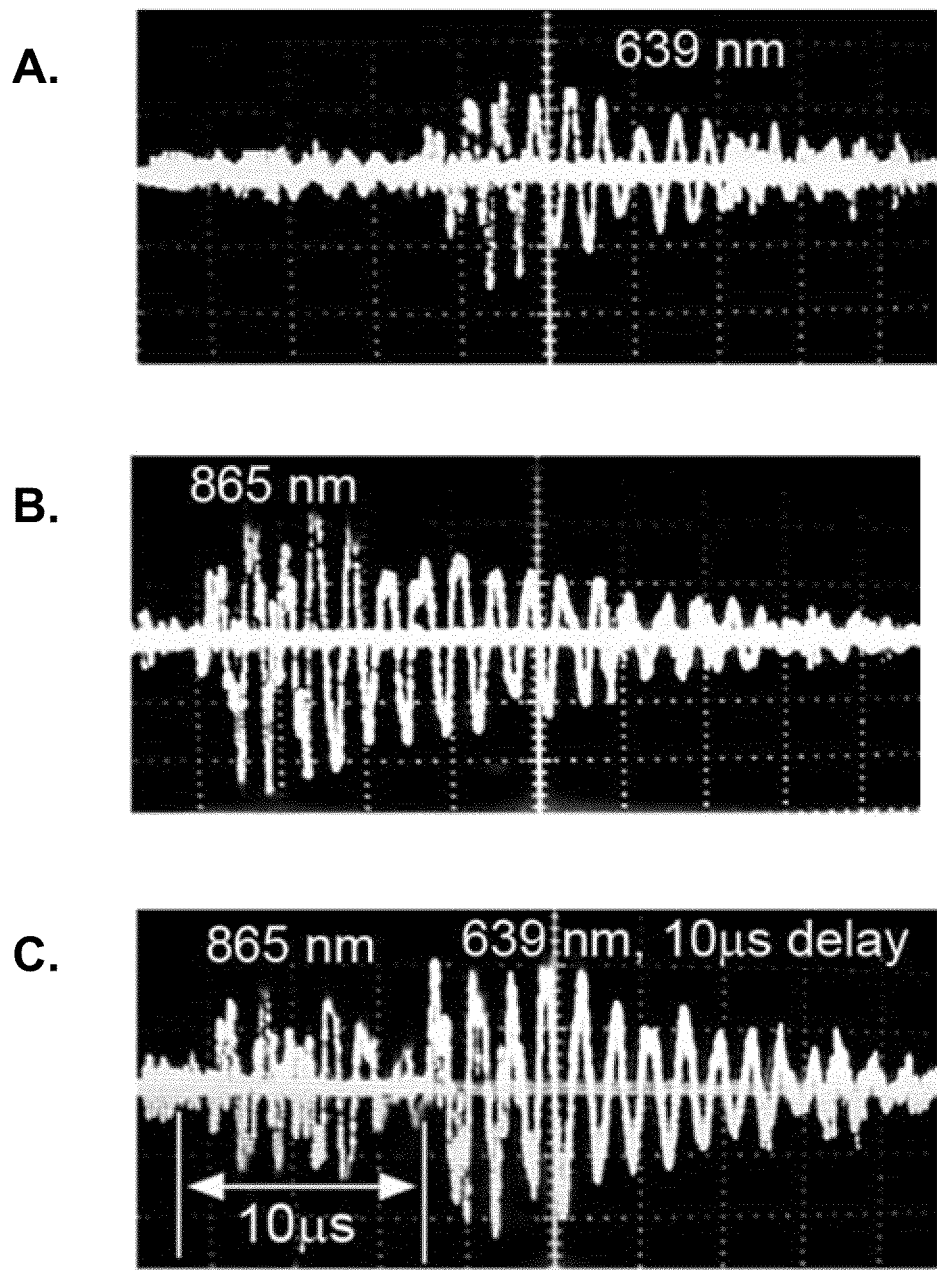
FIG. 13 shows oscilloscope traces of the two-wavelength, time-resolved detection of PA signals from: (A) necrotic lymphocytes labeled with gold nanorods absorbing 639 nm laser pulses, (B) apoptotic lymphocytes labeled with gold nanoshells absorbing 865 nm laser pulses, and (C) live neutrophils labeled with carbon nanotubes absorbing both the 639 nm and the 865 nm laser pulses.

The PA signals had one of three distinctive temporal shapes associated with the response of the three different labels to the paired laser pulses, shown in FIG. 13. PA signals from necrotic lymphocytes marked with GNR were generated in response to the 639 nm laser pulse only, after a 10-µs delay, as shown in FIG. 13A. The apoptotic lymphocytes marked with GNS generated PA signals in response to laser pulse at a wavelength of 865 nm with no delay, as shown in FIG. 13B. Live neutrophils marked with CNT generated two PA signals after a 10-µs delay, as shown in FIG. 13C. One signal was generated in response to the 639 nm laser pulse, and the second PA signal was generated in response to the 850-nm laser pulse, due to comparable CNT absorption at both wavelengths.

The results of this experiment demonstrated that with the use of various contrast substances and two wavelength cell identification techniques, the in vivo PAFC apparatus detected and discriminated between live neutrophils, necrotic lymphocytes, and apoptotic lymphocytes that were circulating in the lymphatic vessels. This method may also be extended to unlabelled cells circulating in the lymphatic or circulatory systems, using a pair of laser pulse wavelengths selected to generate a unique PA signal shape for each cell type to be detected.

Example 11

Spatial Resolution and Maximum Detectible Vessel Depth of a Prototype In Vivo PAFC System was Assessed To determine the maximum spatial resolution and maximum detectible vessel depth of the PAFC system, the following experiment was conducted using the prototype PAFC system described in Experiment 2 and the mouse ear model with circulating melanoma cells, as described in Example 7. Mouse melanoma cells were injected into the tail veins of nude mice and PAFC measurements were conducted as described in Example 7.

The PAFC system achieved a lateral resolution of 5-15 µm when detecting melanoma cells circulating in mouse ear blood vessels with diameters of 10-70 µm at depths of 50-150 µm. However, when melanoma cells circulating in mouse ear blood vessels at a depth of 0.5 mm were measured, the lateral resolution decreased to 30-50 µm due to the scattering of the 850 nm laser pulses by the additional tissue between the PAFC laser and the targeted blood vessels.

The maximum potential of the PAFC to detect cells circulating in deep vessels was estimated by overlaying layers of mouse skin of varying thickness over intact mouse skin containing peripheral blood vessels at a depth of approximately 0.3 mm below the surface of the intact skin. Using the PAFC system described in Example 2 with an unfocused ultrasound transducer (Panametrics model XMS-310, 10-MHz), PA signals were detected at total skin thicknesses up to approximately 4 mm, with a 27-fold signal attenuation due to light scattering. When a focused ultrasound transducer was used (Panametrics model V316-SM, 20 MHz, focal length 12.5 mm), PA signals were detected from melanoma cells circulating in the mouse aorta at a depth of approximately 2.5 mm, resulting from a laser pulse wavelength of 850 nm. Even at a total tissue depth as high as 11 mm, the PA signals emitted by circulating metastatic melanoma cells illuminated by 532 nm laser pulses remained discernible from the background PA signals from surrounding tissues. The lateral resolution at this vessel depth, measured by changing the angle of the ultrasonic transducer, was estimated to be approximately 250 µm (data not shown).

The results of this experiment demonstrated that the PAFC system was capable of detecting circulating melanoma cells at a vessel depth of up to 11 mm with a resolution of approximately 250 µm. This resolution may be improved significantly through the use of higher frequency ultrasound transducers, such as 50 MHz transducers.

Example 12

The Sensitivity of the Spatial Resolution of a Prototype In Vivo PAFC Device to Skin Pigmentation Levels was Assessed Using the Nude Mouse Model To determine the sensitivity of the PAFC system to the level of skin pigmentation, the following experiment was conducted. The PAFC device described in Example 2 was used to measure PA signals from blood vessels in nude mice skin with low and high levels of pigmentation using methods similar to those described in Example 7.

In the low-pigmented nude mouse model, the background PA signal from skin cells was very weak. PA signals measured by a high frequency ultrasound transducer (Panametrics model V-316-SM, 20 MHz) resulting from the simultaneous irradiation of two circulatory vessels at depths of approximately 0.3 mm and 2.4 mm, were determined to have a time separation of approximately 1.4 ms. This delay is consistent with signals emitted by cells with a separation distance of 2.1 mm, assuming a velocity of sound in soft tissue of approximately 1.5 mm/ms. Similar results were obtained for measurements of circulatory vessels in the highly pigmented nude mouse model (data not shown).

The results of this experiment demonstrated that the level of skin pigmentation did not significantly affect the spatial resolution of the PAFC device. For strongly pigmented skin, the assessment of deeper vessels may actually be enhanced because the skin pigmentation may facilitate the discrimination between PA signals from circulating individual cells and PA signals from the skin.

Example 13

Methods of Enriching the Incidence of Circulating Metastatic Cells Measured by PAFC In Vivo were Demonstrated Using the Mouse Ear Model To determine the feasibility of novel methods for increasing the concentrations of circulating metastatic cells detected by the in vivo PAFC device, the following experiment was conducted. Using the mouse ear model to measure the incidence of circulating metastatic melanoma cells, as described in Example 7, the effect of gentle mechanical squeezing of blood microvessels was assessed. This method of enriching the local incidence of rare circulating cancer cells in vivo exploited the size differences between melanoma cells (16-20 mm), WBC (7-8 mm), and RBC (5-6 mm) and the high deformability of RBC compared to cancer cells. The lumen size of the microvessel was decreased to 10-15 m through gentle mechanical squeezing of blood microvessels in 50-m microvessels of mouse ear. After squeezing a 50-m mouse ear blood vessel for 10 min, then quickly releasing the vessel, the rate of metastatic melanoma cells measured by PAFC immediately after vessel release increased approximately 8-fold, relative to the rate measured before squeezing. The degree of blood vessel squeezing could be controlled by monitoring increases and decreases in PA signal amplitudes.

The results of this experiment demonstrated that local enrichment of circulating metastatic melanoma cells was achieved through the mechanical restriction of circulatory vessels.

Example 14

The Background Absorption by Surrounding Blood Cells was Manipulated by Changes in Blood Oxygenation, Hematocrit, and Blood Osmolarity To determine the effects of changes in blood oxygenation, hematocrit, and osmolarity on the background absorption of blood cells during in vivo PAFC, the following experiment was conducted. The absorption of laser energy by hemoglobin in its oxygenated ($HbO_2$) and deoxygenated (Hb) forms differs, depending on the oxygen saturation state of the hemoglobin and the wavelength of the laser pulse. The total absorption of red blood cells decreases as oxygenation increases for laser pulse wavelengths 810-900 nm, and the absorption of red blood cells decreases with increasing blood oxygenation at laser pulse wavelengths of 650-780 nm. Thus, the oxygenation of the red blood cells can be manipulated to minimize the background PA signals emitted by the red blood cells.

Pure oxygen was delivered to a mouse using a mask around the mouse's head, and the background PA signal obtained before and after the increased blood oxygenation was measured using the in vivo PAFC system described in Example 2. The increased blood oxygenation resulting from the exposure of the mouse to pure oxygen for 15 minutes caused the background PA signal from veins to decrease by a factor of 1.36±0.14, using a laser pulse wavelength of 750 nm. Replacing the delivery of pure oxygen with the delivery of pure nitrogen led to a 35% decrease in background PA signal in an arteriole at a laser pulse rate of 900 nm.

Another experiment was conducted to assess the effects of decreasing the density of the circulating RBC as measured by the hemotocrit on the background signal from circulating red blood cells. The hemotocrit of a mouse's blood was temporarily reduced by the intravenous injection of 0.5 ml of standard saline solution into the vein tail. After the saline injection, PA signals from a 50-µm ear mouse vein dropped by a factor of 2.3±0.3, and nearly returned to initial levels within about 1.5 minutes.

Blood osmolarity causes an increase in the RBC volume (swelling) that resulted in a decrease in the average intracellular Hb concentration. Injection of 100-mL of hypertonic NaCl solution into the mouse tail vein led to an approximately 2-fold decrease in the PA signal in the ear vein.

The results of this experiment demonstrated that the background PA signals resulting from the emission of PA signals by red blood cells may be minimized by manipulation of the chemical environment of the blood, including blood oxygenation, hemotocrit, and blood osmolarity. These approaches may be readily applicable to human subjects because the procedures used in this experiment are routinely used in clinical practice.

Example 15

Microbubbles Conjugated with Nanoparticles were Assessed as a Contrast Agent for PAFC To assess the effectiveness of microbubbles conjugated with nanoparticles as a contrast agent in PAFC, the following experiment was conducted. Microbubbles (Definity Inc.) with average diameters of 2-4 m were incubated with PEG-coated gold nanoshells (GNS), previously described in Example 10 for 1 hr at room temperature. The measurement of PA signals in vitro, as described in Example 1 was conducted for microbubbles only, GNS only and microbubbles conjugated with GNS. The microbubbles conjugated with GNS emitted the strongest PA signals, the GNS only emitted somewhat weaker PA signals, and the microbubbles alone emitted negligible PA signals (data not shown).

Increasing the energy of the laser pulses illuminating the GNS-conjugated microspheres led to a dramatic increase of the emitted PA signals, followed by the disappearance of the microbubbles after a single laser pulse. This observation was attributed to the laser-induced overheating of the GNS leading to a dramatic temperature increase of the gas trapped inside of the microbubbles that ultimately ruptured the microbubbles.

The results of this experiment demonstrated that microbubbles conjugated with GNS were an effective contrast agent, but that the energy of the laser pulses must be carefully moderated to avoid bursting the microbubbles. Because the microbubbles may be selectively attached to blood clots or taken up by activated white blood cells, this contrast agent may expand the potential applications of in vivo PAFC to include the detection of blood clots and certain activated white blood cells.

Example 16

Two-Wavelength In Vivo PAFC Used to Detect Circulating Exogenous Melanoma Cells

To demonstrate the ability to use two-wavelength in vivo PAFC to detect injected unlabeled melanoma cells in circulation with extremely high sensitivity, the following experiment was conducted. B16F10 cultured mouse melanoma cells (ATCC, Rockville, Md.) were obtained and maintained as described in Example 6. The experiments were performed using a nude mouse ear model similar, described in Example 2 (n=25). To mimic metastatic cells, approximately $10^5$ tumor-derived B16F10 cells in a 100-µl volume of saline solution were injected into the mouse circulatory system through a tail vein and then monitored in an ear vein using an apparatus and methods similar to those described in Example 10. An ear blood vessel was illuminated by two laser pulses at wavelengths of 865 nm and 639 nm with a 10-ms delay between the pulses.

Figure 14:
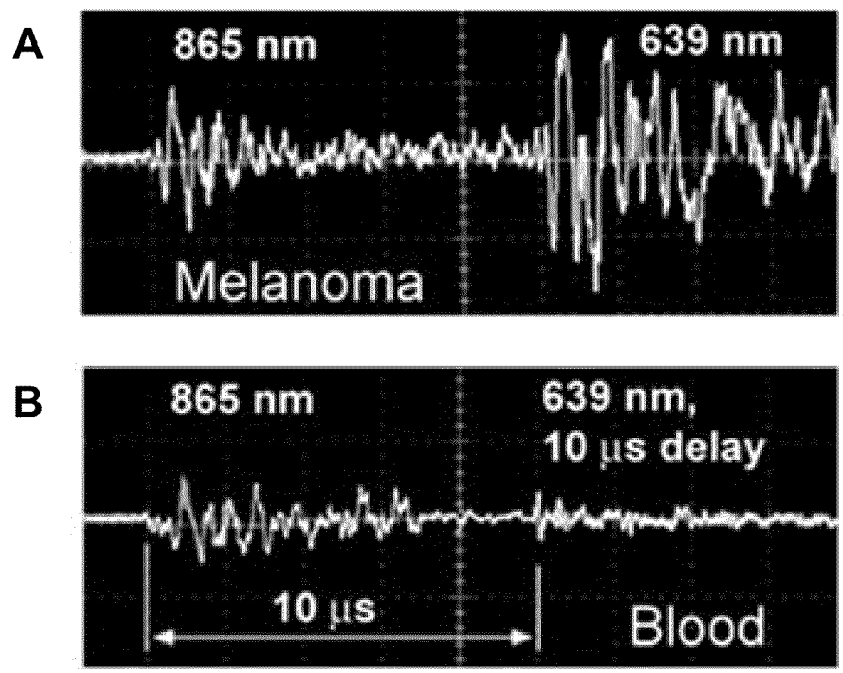
FIG. 14 shows oscilloscope traces of the two-wavelength, time-resolved detection of PA signals from: (A) melanoma cells absorbing 865 nm and 639 nm laser pulses, and (B) red blood cells absorbing 865 nm and 639 nm laser pulses.

The melanoma cells were distinguished from surrounding blood cells, based upon the distinctive absorption spectra of the melanoma cells, as described previously in Example 6 and summarized in FIG. 9. Melanoma cells emitted two PA signals with a 10-ms delay, corresponding to the two laser pulses. The first PA signal, induced by the 639 nm laser pulse, had a higher amplitude than the PA signal induced by the 865 nm pulse, as shown in FIG. 14A. Red blood cells, the most numerous blood cells in circulation, generated two PA signals with lower amplitudes than the corresponding PA signals generated by the melanoma cells. In addition, for the red blood cells, the amplitude of the PA signal induced by the 865 nm pulse was slightly higher than the PA signal induced by the 639 nm laser pulse, as shown in FIG. 14B.

Figure 15:
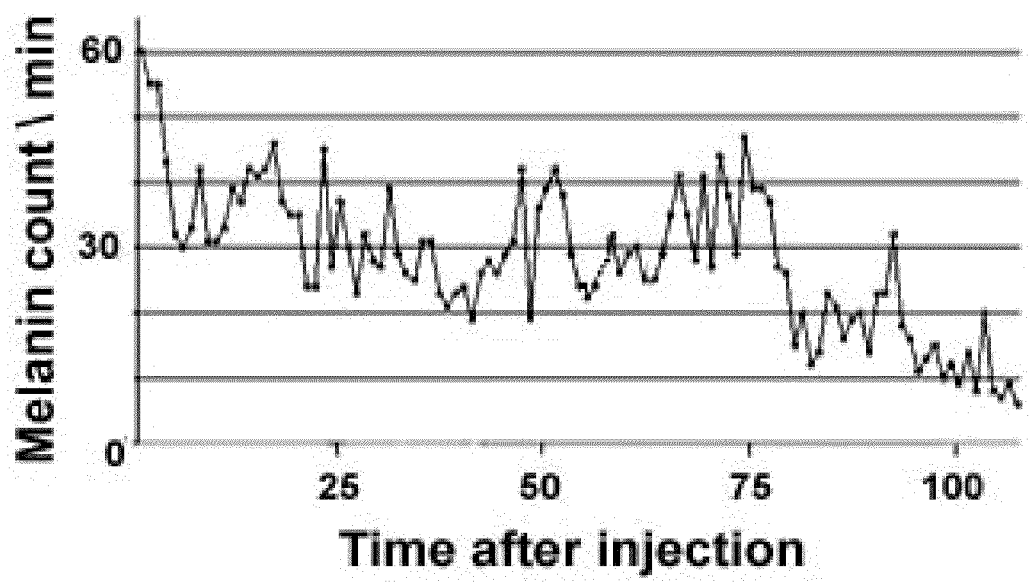
FIG. 15 is a summary of the PA signal rates from melanin particles detected in a mouse ear lymph microvessel 2 hours after injection.

The PA signals corresponding to the melanin particles were cleared over a two-hour period following the injection, as shown in FIG. 15.

Based on comparisons to similar data measured for melanoma cells labeled with markers that emitted strong PA signals, it was estimated that approximately 89% of the unlabelled melanoma cells were detected (data not shown). This percentage was lower than that found in previous in vitro studies (96%) and indicated a false-negative-signal rate of 1.5 cells/min because of the influence of background absorption by RBCs (data not shown). Longer-term monitoring of PA signals from ear blood vessels without prior melanoma cell injection detected no false-positive signals using as its criteria a signal-to-noise ratio≥2, where the signal noise was associated with fluctuations of laser energy and the density of red blood cells in the detected volume.

The results of this experiment demonstrated that two-color in vivo flow cytometry was an effective method of detecting metastatic melanoma cells in circulation. It was estimated that the method described above detected approximately 89% of the melanoma cells in circulation, with slightly lower detection rates due to skin pigmentation.

Example 17

Two-Wavelength In Vivo PAFC was Used to Detect Circulating Spontaneous Metastatic Cells During Tumor Progression An experiment was conducted to determine the ability of two-wavelength in vivo PAFC to detect relatively scarce endogenous metastatic melanoma cells circulating in lymph vessels. The PAFC system described in Example 10 was used to monitor endogenous metastatic melanoma cells in mice. Tumors were induced in nude mice by subcutaneous injections of melanoma cells using methods similar to those described in Example 7. Tumors formed and proliferated in the skin of the ear and the back of the nude mice over a period of 4 weeks, as previously described in Example 7.

Figure 16:
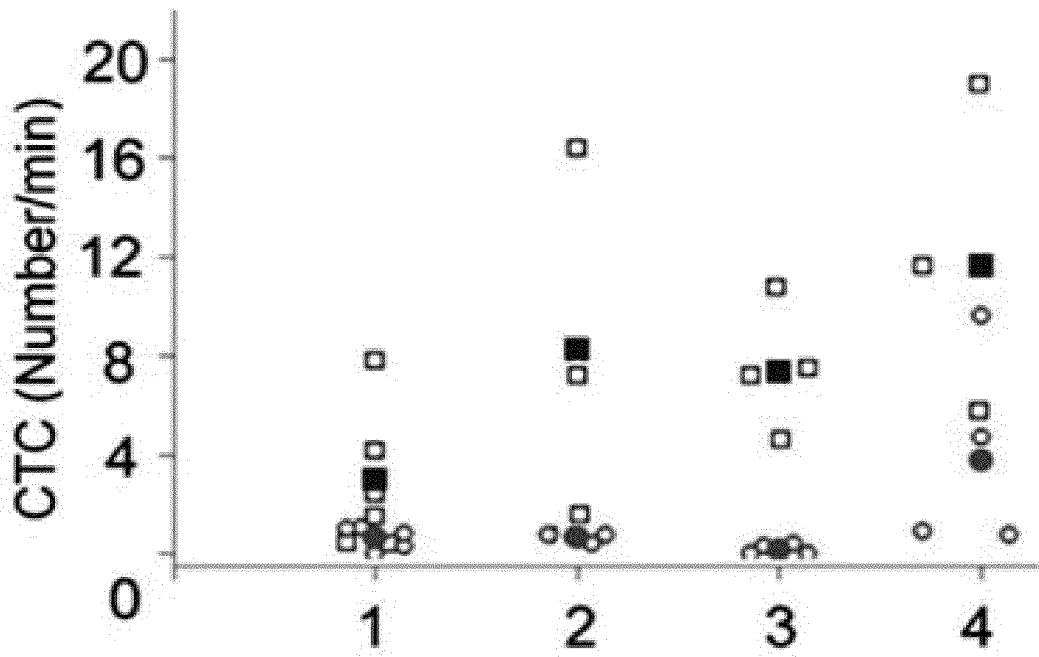
FIG. 16 is a summary of the PA signal rates from single melanoma cells detected in a mouse ear lymph microvessel 4 weeks after tumor inoculation.

PAFC was used to count spontaneous metastatic melanoma cells in a ~50 µm-diameter ear blood vessel and a 100-200-µm-diameter skin blood vessel during tumor progression in the ear and skin of a mouse, as summarized in FIG. 16. As previously described in Example 7, the skin tumor growth rate was faster than that of the ear tumors, and metastatic melanoma cells appeared more quickly in the circulation, as indicated by the mean cell detection rate measured in the skin capillaries, shown as solid square symbols in FIG. 16. In particular, within the first week after the induction of the tumors, about 1-4 melanoma cells/min were detected in the skin vasculature, and as the tumor size increased, the rate of detection of metastatic melanoma cells gradually increased to about 7 cells/min and about 12 cells/min after 3 weeks and 4 weeks, respectively.

The results of this experiment indicated that in vivo PAFC and PA mapping were sensitive methods with which to monitor the development of metastasized melanoma cells non-invasively, with high sensitivity and accuracy.

Example 18

PAFC System was Used to Determine Photoacoustic Response of Quantum Dot Markers In Vitro An experiment was conducted to determine the ability of two-wavelength in vivo PAFC to detect quantum dot cell markers in vitro. The PAFC system described in Example 2 was used to measure photoacoustic pulses emitted by quantum dots in response to laser pulses with wavelengths of 625 nm, pulse widths of 8 ns, and laser fluences ranging 0.001-10 J/m$^2$. The laser beam used to pulse the quantum dots had a diameter of about 20-30 µm in the sample plane. Quantum dots were obtained commercially with a polymer coating as well as with a streptavidin protein coating (Qdot 655 nanocrystals, Invitrogen, Carlsbad Calif.). The quantum dots had diameters of about 15-20 nm and an emission wavelength of about 655 nm. Either single or aggregations of quantum dots were diluted with a buffer of 2% BSA/PBS and mounted in a layer of less than 1 µm on a microscope slide.

Figure 17:
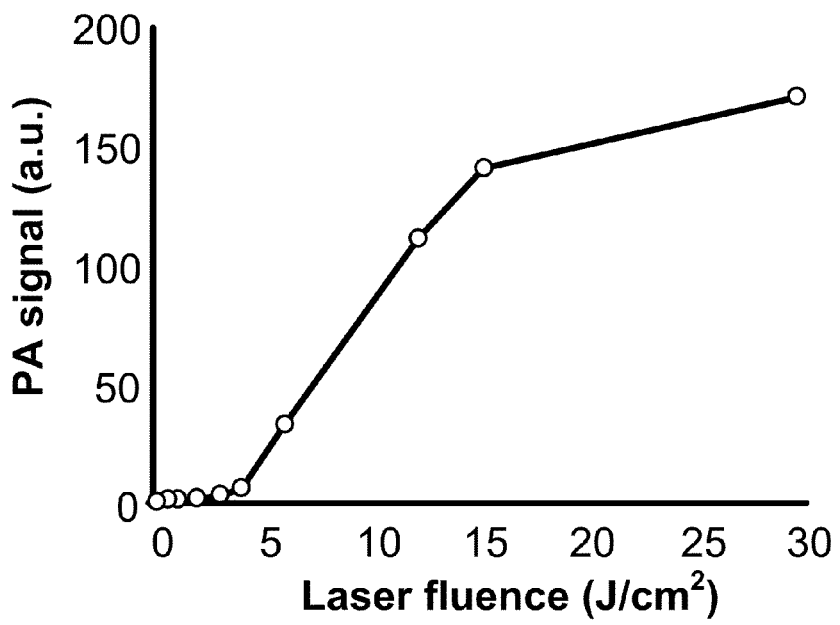
FIG. 17 is a summary of the PA signal amplitude generated by quantum dot markers as a function of laser fluence.

The PAFC system was used to pulse the quantum dot preparation with laser fluences ranging from 0.001-30 J/m$^2$. The magnitudes of the PA signals emitted by the quantum dots are summarized in FIG. 17. The PA signal response of the quantum dot preparations had a non-linear response to the variations in laser fluences. PA signal amplitude gradually increased in the laser fluence range from 0.1-1 J/cm$^2$. Through the laser fluence range between 1.5-7 J/cm$^2$, the response increased dramatically in a non-linear manner, and continued to increase in magnitude up to a laser fluence of 15 J/cm$^2$. At laser fluences above 15 J/m$^2$, the responses of the quantum dot preparations were saturated.

Figure 18:
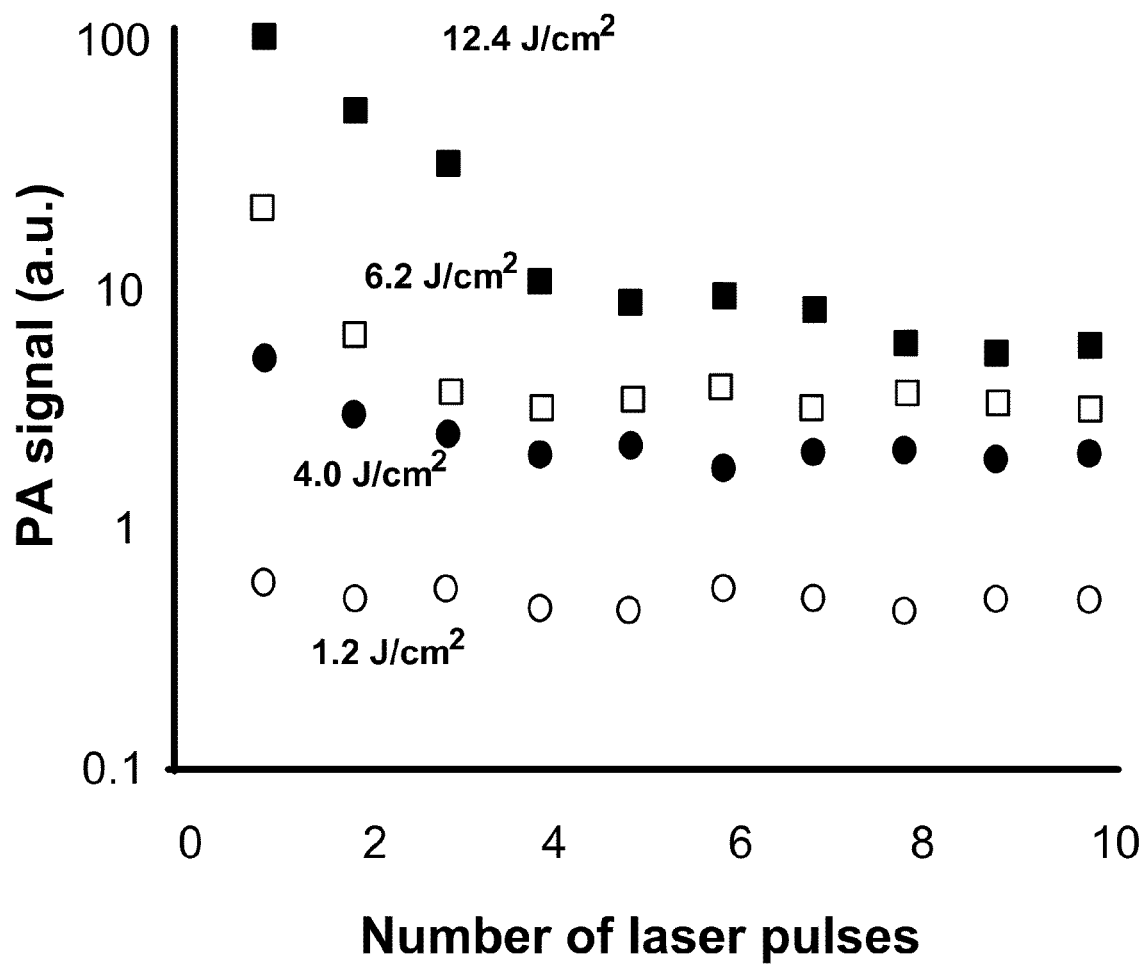
FIG. 18 is a summary of the PA signal amplitude generated by quantum dot markers as a function of the number of laser pulses.

The PA signal response as a function of the number of laser pulses for laser fluences of 1.2, 4.0, 6.2, and 12.4 J/cm$^2$ are summarized in FIG. 18. There was no sign of alteration of the laser pulse-induced PA signals at laser fluences below 3 J/cm$^2$, indicating no blinking behavior, unlike the stereotypical fluorescent blinking behavior observed in quantum dots. At higher laser fluences, significant decreases in the PA signal amplitude were observed with an increase in the number of pulses, possibly due to laser induced melting of thermal-based destruction by explosion of the quantum dots.

The results of this experiment indicated the quantum dots generated strong PA signals in response to laser pulses.

Example 19

PAFC System was Used to Detect Bacteria and Melanoma Cells Marked with Magnetic Nanoparticles In Vivo To demonstrate the application of magnetic nanoparticles as photoacoustic (PA) contrast agents, the following experiment was conducted.

*S. aureus* bacteria, described in Example 4, and melanoma cells, described in Example 6, were labeled with super paramagnetic iron oxide nanoparticles (Clementer Associates, Madison, Conn.). The nanoparticles consisted of a 50-nm core of magnetite ($Fe_3O_4$), coated with a 10-15 nm layer of Dextran and fluorescent dye. Both bacterial cells and melanoma cells were cultured at a density of approximately $10^6$ cells/mL, and magnetic nanoparticles were added to the cell cultures at a density of 0.5 mg/mL, and loaded into the cells by endocytosis for a minimum of 1 hour at 37° C. Labeled cells were centrifuged at 5,000 rpm for 3 minutes and the resulting pellet was resuspended in PBS.

The photoacoustic flow cytometry system (PAFC) system was similar in design to the PAFC system previously described in Example 2, with modifications to the laser, amplifier, and transducer components. A diode laser 905-FD1S3J08S (Frankfurt Laser Company) with driver (IL30C, Power Technology Inc, Little Rock, Ark.) was used to pulse the unbound magnetic nanoparticles and labeled cells with a pulse width of 15 ns, and a pulse repetition rate of 10 kHz. The laser beam dimensions used to pulse the nanoparticles and cells had an elliptical cross-section with minor and major axis dimensions of 11 µm and 75 µm, respectively, and a fluence energy maximum of 0.6 J/cm$^2$. The laser-induced PA signals were detected by a 5.5 mm-diameter, 3.5 MHz ultrasound transducer (model 6528101, Imasonic Inc., Besançon, France), amplified using a 2 MHz amplifier (Panametrics model 5660B) and recorded with a Boxcar data recorder (Stanford Research Systems, Inc.) and a Tektronix TDS 3032B oscilloscope.

To determine the clearance rate of unbound magnetic nanoparticles, the nude mouse ear model described in Example 2 was used. A 100-mL PBS suspension of the magnetic nanoparticles at a concentration of about $10^{11}$ nanoparticles/mL was injected into the vein tail of the mice.

Figure 19:
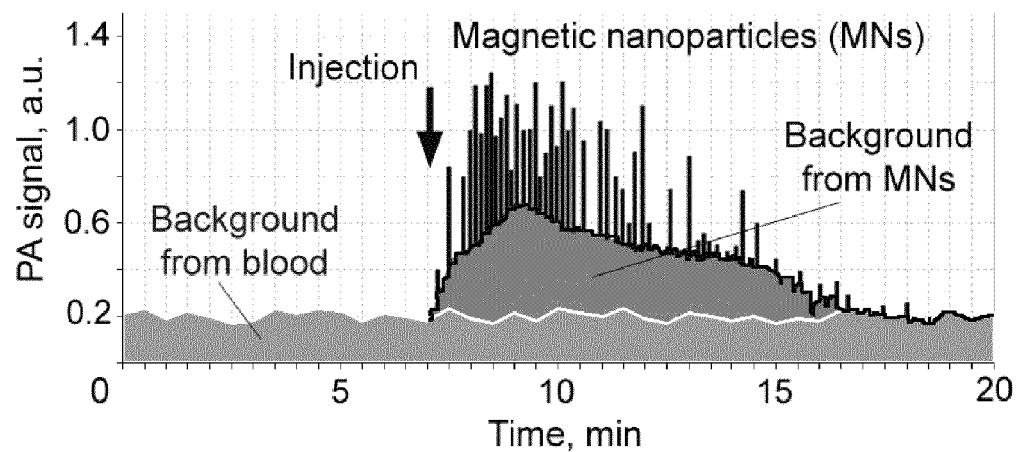
FIG. 19 is a summary of the PA signal amplitudes from a capillary over the 20 minutes following the injection of magnetic nanoparticles.

The magnetic nanoparticles were detected using the PAFC system described above. The laser pulses were delivered to the unbound magnetic nanoparticles at a wavelength of 639 nm and a laser fluence of 1.5 J/cm$^2$. The detection and subsequent clearance of the magnetic particles in the nude mouse ear model are summarized in FIG. 19. PA signals corresponding to the magnetic nanoparticles appeared within the first minute after injection. The PA signals were a combination of a fluctuating continuous PA background with superimposed large-amplitude PA signals. The magnitude of the background signal associated with the magnetic nanoparticles exceeded the PA background signals from the blood vessels by a factor of 2-3. The stronger but less frequent large-amplitude PA signals may be associated with random fluctuations of the number of magnetic nanoparticles in the detected volume and appearance of small aggregates of magnetic nanoparticles. The clearance time of the magnetic nanoparticles from the mouse ear microcirculation was in the range of 10-20 minutes.

Figure 20:
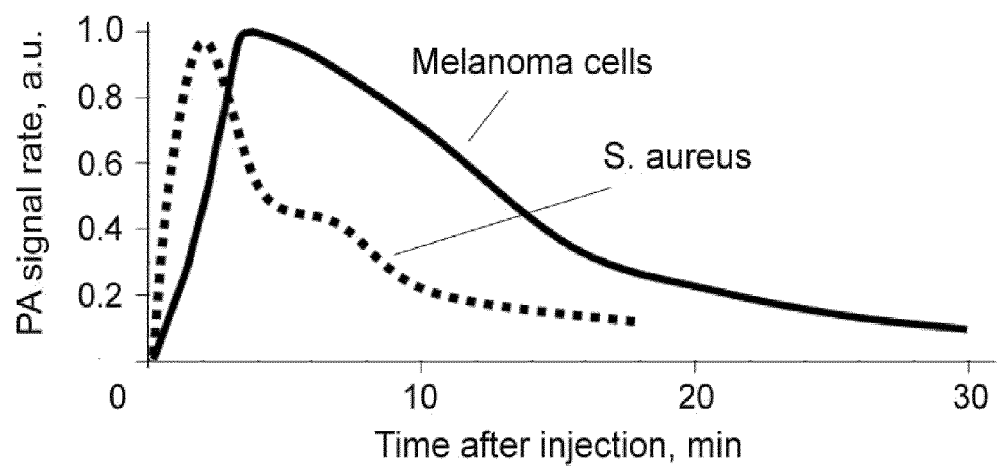
FIG. 20 is a summary of the PA signal rates from single melanoma cells and bacteria cells labeled with magnetic nanoparticles detected in a mouse ear capillary 30 minutes after injection.

Approximately $10^5$ B16F10 melanoma cells or *S. aureus* labeled with magnetic nanoparticles in 100 µL of saline solution were injected into a mouse tail vein and then monitored in the mouse ear using the PAFC system described above. Labeled melanoma cells were detected using a 905 nm, 0.4 J/cm² laser pulse, and the bacterial cells were detected using an 850 nm, 0.9 J/cm² laser pulse. The resulting PA signals emitted by *S. aureus* and melanoma cells labeled with magnetic nanoparticles are summarized in FIG. 20. Numerous PA signals from individual circulating cells were detected, with a maximum rate of detection within the first 1-3 minutes. The average half-life of the labeled bacteria and cancer cells in the blood microcirculation was 4.5 and 12 min, respectively.

Figure 21:
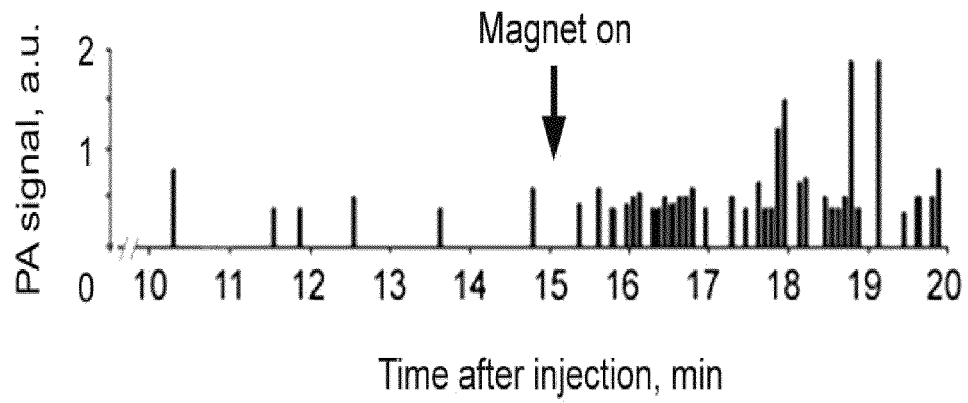
FIG. 21 is a summary of the PA signal rates from melanoma cells labeled with magnetic nanoparticles before and after the application of a magnetic field, detected in a mouse ear capillary 20 minutes after injection.
Figure 22:
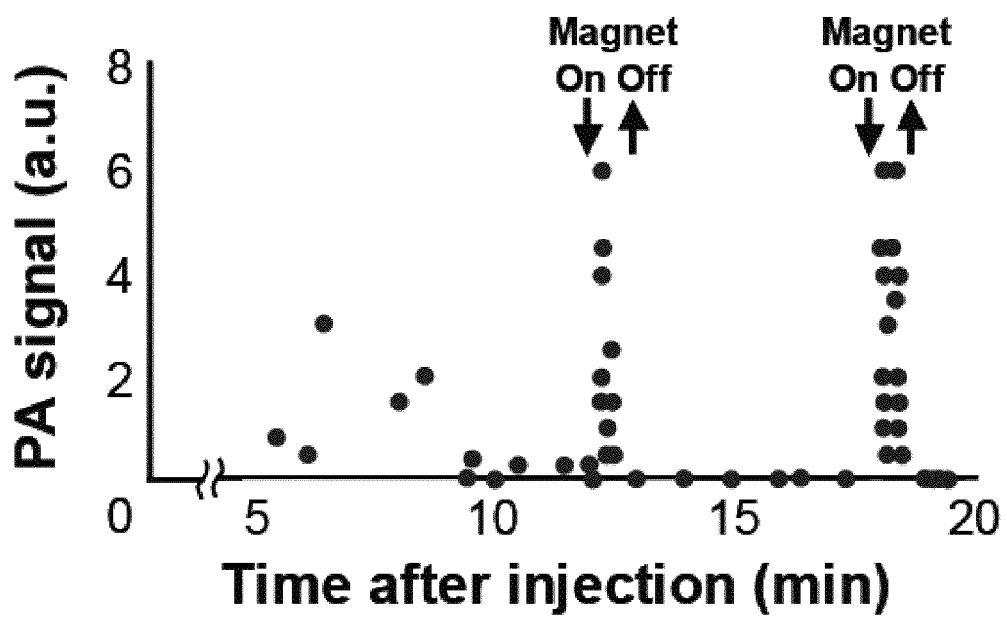
FIG. 22 is a summary of the PA signal rates from bacterial cells labeled with magnetic nanoparticles before and after the application of a magnetic field, detected in a mouse ear capillary 20 minutes after injection.

After the labeled melanoma cells and bacteria were essentially cleared from the circulation and only rare PA signals were detected, a local permanent magnetic field was imposed through intermediate tissue to the blood microvessels. The local permanent magnetic field was provided by a cylindrical Neodymium-Iron-Boron (NdFeB) magnet with Ni—Cu—Ni coating that was 3.2 mm in diameter and 9.5 mm long with a surface field strength of 0.39 Tesla (MAGCRAFT, Vienna, Va.). The distance between the magnet and the microvessel walls ranged between 50-100 µm. As shown in FIGS. 21 and 22, the application of the magnetic field to the blood microvessels led to an immediate increase in both PA signal amplitudes and rate of detection in the vicinity of the magnet for the labeled melanoma cells and bacterial cells respectively.

The results of this experiment demonstrated that magnetic nanoparticles could be used to label circulating melanoma and bacteria cells for use in the prototype PAFC system. Further, a magnetic field applied to the blood microvessel in which the PAFC detected circulating cells was able to locally enrich the concentration of cells to be detected.

Example 20

Magnet-Induced Amplification of Signals from CD44+ Cells Targeted by Magnetic Nanoparticles To assess the viability of manipulating cells labeled with magnetic nanoparticles (MNPs) using an external magnetic field, the following experiments were conducted.

Human breast cancer cells (MDA-MB-231, American Type Culture Collection, Manassas, Va.) were cultured according to the vendor's specifications. The cells were cultured to confluency in vitro, detached with 0.25% trypsin-0.53 mM EDTA, washed and resuspended in PBS. The resuspended cells were then incubated for one hour at 37° C. with 30 nm spherical magnetic nanoparticles (Ocean NanoTech, Springdale, Ark.) conjugated with antibodies targeted to human CD44 receptor (MNP-CD44). In addition, the antibodies were stained with fluorescent labels (fluorescein isothiocyanate-dextran [FITD], BD Pharmaceuticals) according to the manufacturer's specification prior to conjugation to the MNPs. The concentration of MNP-CD44 particles added to the PBS was about $0.1 \times 10^3$-$1 \times 10^3$ particles per suspended cell. The labeled cells were resuspended in PBS, placed in 8.6 ml wells (Molecular Probes) and covered with a top cover. In this example, the cells were triple labeled, since the MNP portion of the MNP-CD44 particle functions as a photoacoustic and photothermal contrast agent, and the FITD staining of the antibody functions as a fluorescent label.

A permanent magnetic field was provided by a magnet tip gently attached to the top cover of the slides for the manipulation of the labeled cells. The magnet was a cylindrical neodymium-iron-boron (NdFeB) magnet with Ni—Cu—Ni coating (MAGCRAFT, Vienna, Va.). This cylindrical magnet had a diameter of 3.2 mm, a length of 9.5 mm, and a surface field strength of 0.39 Tesla.

Figure 23:
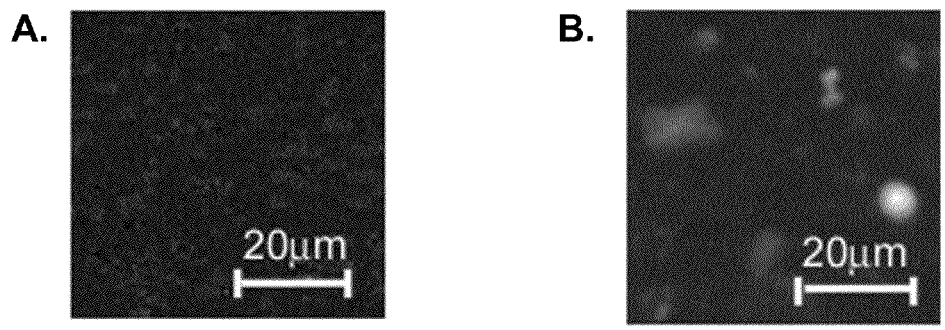
FIG. 23 includes fluorescent microscopic images of a suspension of magnetic nanoparticles conjugated with targeted antibodies.

To assess the effectiveness of the magnet at attracting and clustering the MNP-CD44 particles, the magnetic tip was attached the top cover of a slide containing suspended MNP-CD44 particles only in PBS at a concentration of $10^{11}$ particles/mL. The attachment of the magnet tip to the top cover of the slide induced the migration of the MNPs to the immediate vicinity of the magnet, resulting in a dark spot visible with the naked eye. The identity of the MNP-CD44 particles within the dark spot was verified by fluorescent microscopy. FIG. 23 shows the fluorescent image of the slide before (FIG. 23A) and after (FIG. 23B) the application of the magnetic field to the top cover; the clustered MNP-CD44 particles appear as a bright spot in the lower right corner of FIG. 23B.

Figure 24:
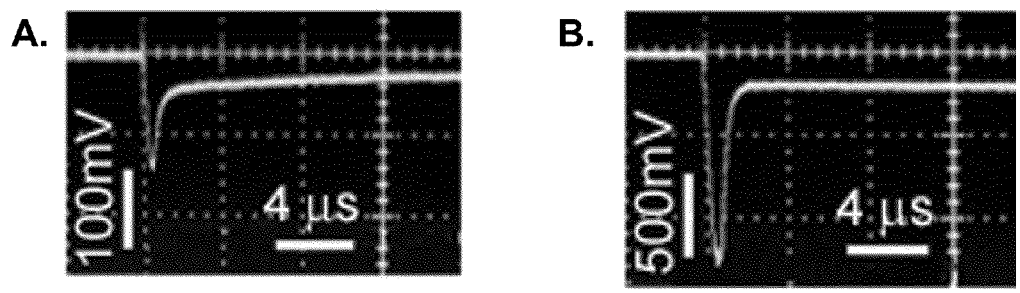
FIG. 24 includes non-linear photothermal (PT) signals obtained from a suspension of magnetic nanoparticles conjugated with targeted antibodies.

Non-linear photothermal (PT) signals were obtained for the same slide before and after the application of the magnetic field, as shown in FIG. 24. The laser used in this experiment had a wavelength of 639 nm, a beam diameter of 15 µm, and a fluence of 50 mJ/cm². The PT signal from the region with a high local concentration of MNP-CD44 particles after the application of the magnetic field (FIG. 24B) was 10-20-fold higher than the PT signal obtained prior to the applied magnetic field (FIG. 24A).

Figure 25:
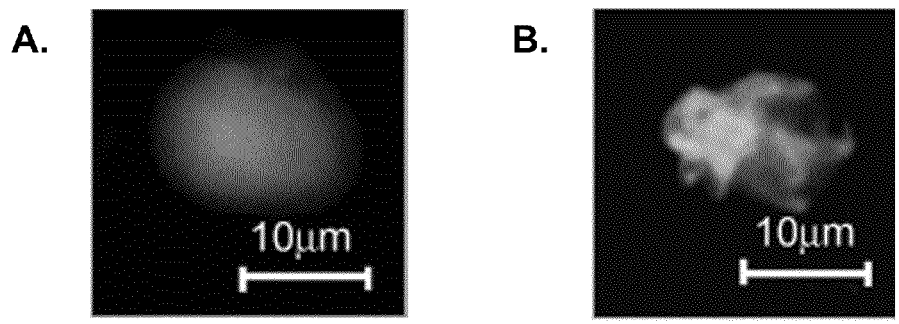
FIG. 25 includes fluorescent microscopic images of a single cancer cell labeled using magnetic nanoparticles conjugated with targeted antibodies.
Figure 26:
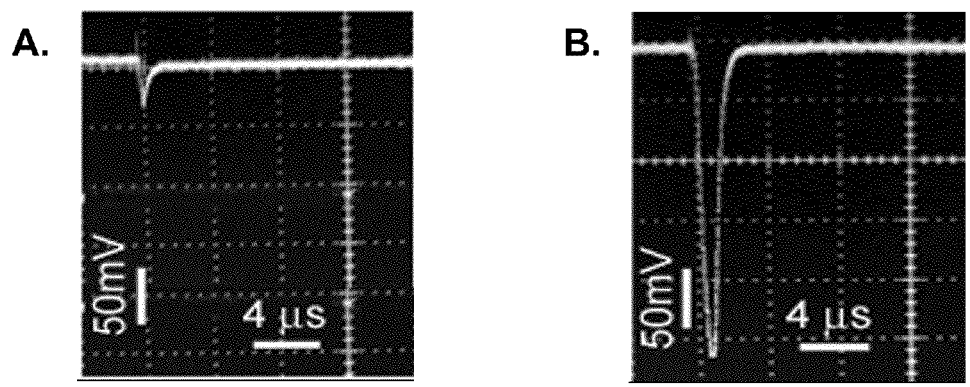
FIG. 26 includes non-linear photothermal (PT) signals obtained from a single cancer cell labeled using magnetic nanoparticles conjugated with targeted antibodies.

Single cancer cells labeled with MNP-CD44 as described above were similarly assessed before and after exposure to the external magnetic field. As shown in FIG. 25, the application of the external magnetic field induced an enhancement of the local fluorescence gradient within the single isolated cell (FIG. 25B) compared to the relatively homogenous spatial fluorescent light distribution prior to exposure to the external magnetic field (FIG. 25A), suggesting magnetic field-induced clustering of the MNPs within the single cell. Further, as shown in FIG. 26, exposure of the isolated labeled cells to the external magnetic field resulted in a 6.6-fold enhancement of the PT signals obtained from these cells (FIG. 26B) relative to the PT signals obtained from the cells before exposure to the magnetic field (FIG. 26A). The appearance of locally dense intracellular clusters of MNPs is likely due to the accumulation of the MNPs under the magnet near cellular structures such as cell membrane that may have acted as mechanical obstacles to impede the further movement of the MNPs.

The results of this experiment indicated that the labeling of cells using MNPs conjugated with antibodies or other biological compounds targeted toward particular cell types renders the cells amenable to manipulation using magnetic fields. Further, the external magnetic field induces the formation of intracellular clusters of MNPs, resulting in the enhancement of PT signals of the labeled cells.

Example 21

Efficacy of Conjugated Nanoparticles Targeted to Circulating Tumor Cells

To assess the efficacy of the binding of nanoparticles conjugated with target compounds directed to receptors specific to circulating tumor cells, the following experiments were conducted. A magnetic nanoparticle (MNP) and a gold nanotube (GNT) were conjugated to known ligands of cancer cell-specific receptors and assessed to determine the contrast of the PA signals produced relative to other blood components, the efficiency of binding to circulating cancer cells, the ability to capture labeled CTCs and circulating MNPs using an external magnetic field, the clearance dynamics of the nanoparticles in vivo, and the clearance dynamics of CTCs labeled using the nanoparticles.

Because human tumor cells are typically heterogeneous, multiplex targeting and a multicolor detection strategy was utilized to increase the specificity of the nanoparticles needed to implement the in vivo identification of circulating tumor cells (CTCs). To this end, the CTCs were labeled with two different labeling particles (magnetic nanoparticles and golden carbon nanotubes), which emitted photoacoustic (PA) signals distinguishable from background PA signals from surrounding blood cells and endothelial tissues. The PA detection of the CTCs labeled using the MNPs and CTCs was conducted by exposing the CTCs to laser pulses at two different wavelengths to enhance the contrast of the PA signal produced by each type of labeling particle.

Figure 27:
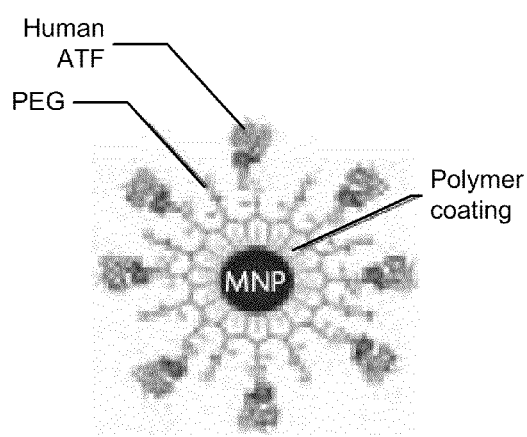
FIG. 27 is a schematic illustration of a conjugated magnetic nanoparticle.

Using methods similar to those described in Example 20, magnetic nanoparticles (MNPs) were conjugated to an amino-terminal fragment (ATF) of the human urokinase plasminogen activator, which serves as specific ligand for the urokinase plasminogen activator receptors that are highly expressed on many types of cancer cells but are expressed at a low level in normal blood and endothelial cells. These conjugated MNPs (MNP-ATFs), illustrated schematically in FIG. 27, served as dual magnetic and photoacoustic contrast agents due to the intrinsic absorption properties of the $Fe_2O_3$ core of the MNPs. In addition, the MNP-ATFs were further conjugated with fluorescein (FITC) to provide additional fluorescence imaging capability in a manner similar to Example 20.

Figure 28:
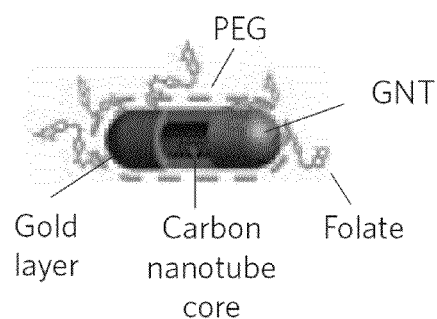
FIG. 28 is a schematic illustration of a conjugated gold nanotube.

The golden carbon nanotubes (GNTs) were conjugated to folate, which serves as a ligand for the folate receptors that are expressed in cancer cells but absent in normal blood. The GNTs selected had average lengths of about 98 nm and average diameters of about 12 nm. The folate was conjugated to the GNTs using electrostatic interactions. The resulting folate-GNT conjugates were washed three times in the presence of 1% polyethylene glycol (PEG) and conjugated with fluorescein (FITC) to provide additional fluorescence imaging capability. These folate-conjugated golden carbon nanotubes (GNT-FOLs) are illustrated schematically in FIG. 28.

Figure 29:
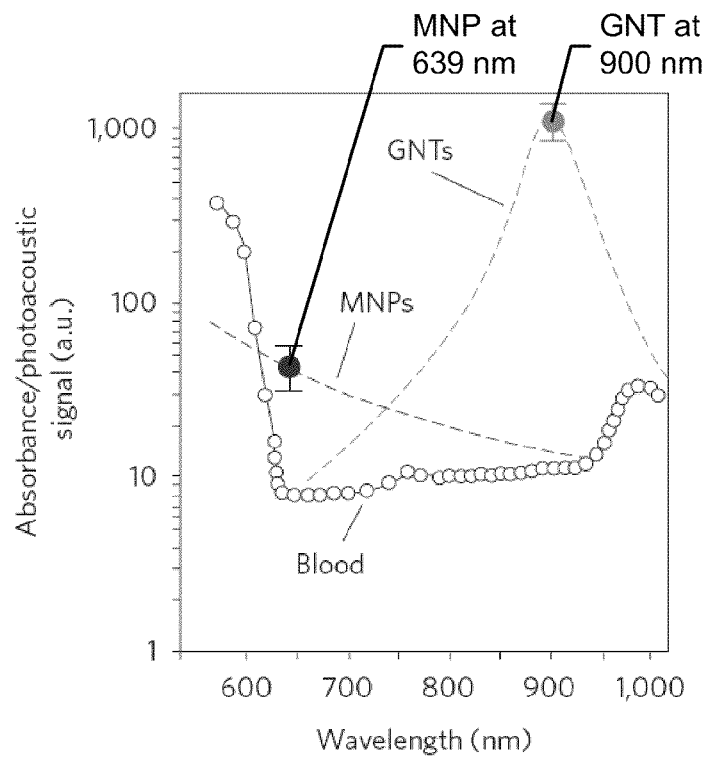
FIG. 29 are estimated photoacoustic spectra showing the PA signals of a magnetic nanoparticle, a gold nanotube, and blood background signals as a function of laser pulse wavelength.

Two laser wavelengths were selected to perform the photoacoustic sensing of the dually-labeled tumor cells. The first wavelength was selected to be 639 nm to provide strong photoacoustic contrast of the PA signal from the MNPs, and the second wavelength of 900 nm was selected to enhance the contrast of the PA signal of the GNTs relative to other blood components. An estimated photoacoustic spectra showing the PA signals of the MNPs, the GNTs, and the blood background signals are shown in FIG. 29, along with the two wavelengths selected for PA sensing.

Figure 30:
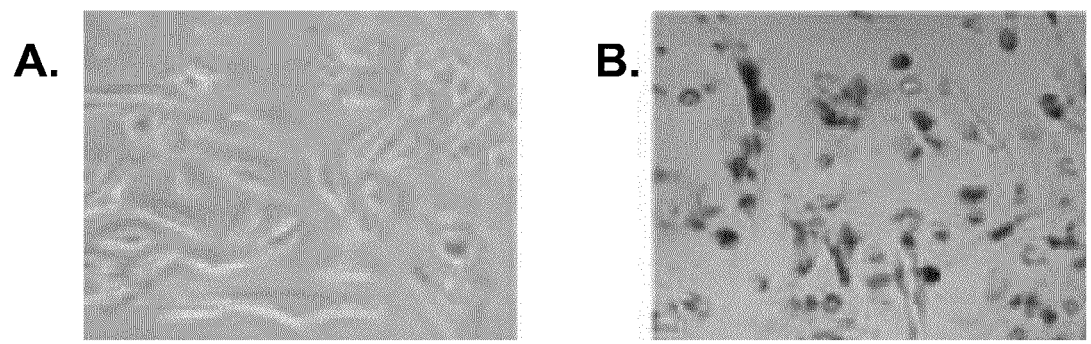
FIG. 30 includes microscope images of a single cancer cell incubated with unconjugated magnetic nanoparticles (FIG. 30A) and of a single cancer cell incubated with conjugated magnetic nanoparticles (FIG. 30B).
Figure 31:
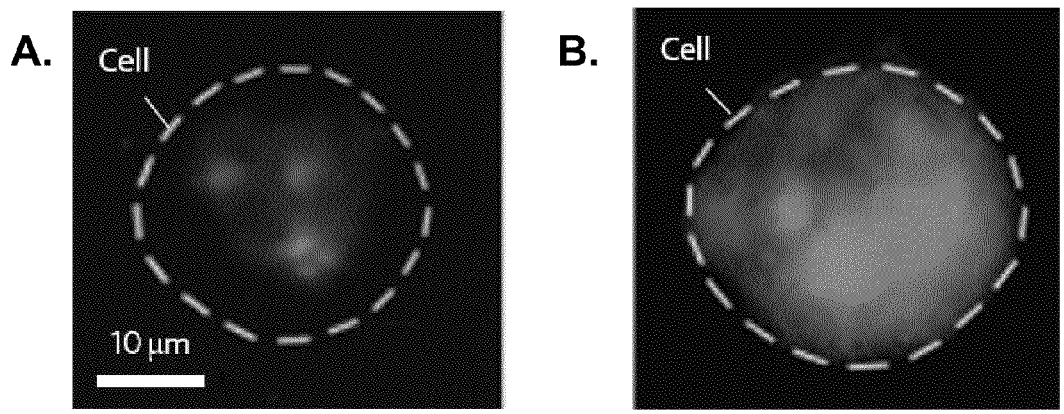
FIG. 31 contains fluorescent microscope images of a single cancer cell incubated with fluoroscein-stained unconjugated gold nanotubes (FIG. 31A) and a single cancer cell incubated with fluoroscein-stained, folate-conjugated gold nanotubes (FIG. 31B).

The human breast cancer cell line MDA-MB-231, which is positive for both the urokinase plasminogen activator and the folate receptor, were used in these experiments. To verify the target specificity of the conjugated MNP nanoparticles in vitro, the cancer cells were incubated with unconjugated MNP and with conjugated MNP-ATF nanoparticles for two hours at 37° C. After incubation, the cells were subjected to Prussian Blue staining, which stained the iron cores of any MNPs attached to the cells. FIG. 30 includes microscope images of a single cancer cell incubated with unconjugated MNPs (FIG. 30A) and with MNP-ATF (FIG. 30B). To verify the target specificity of the conjugated GNTs in vitro, the cancer cells were incubated with GNTs conjugated with fluorescein only or with the conjugated GNT-FOL nanoparticles for two hours at 37° C. Fluorescent images of a single cell incubated with the fluoroscein-conjugated GNTs (FIG. 31A) and a single cell incubated with the GNT-FOL (FIG. 31B) indicated that the GNT-FOL attached specifically to the cancer cells.

Figure 32:
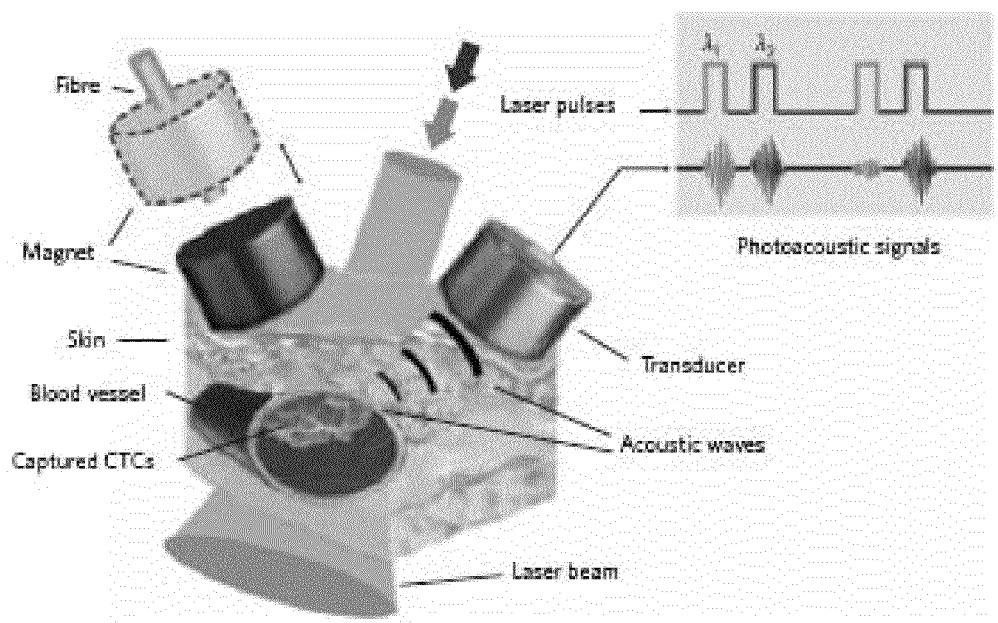
FIG. 32 is a schematic illustration of a PAFC system modified to provide the capability to attach a magnet near the area of interest of the PAFC system.

A PAFC system similar to that described in Example 10 was used with the following modifications, illustrated in FIG. 32. A diode laser (905-FD1S3J08S, Frankfurt Laser Company) and associated driver (IL30C, Power Technology) was used to deliver laser pulses at a wavelength of 905 nm, a pulsewidth of 15 ns and a pulse repetition rate of 10 kHz. In addition, a second co-linear probe pulse from a Raman shifter was delivered at a wavelength of 639 nm, a pulse duration of 12 ns and at a 10-ms delay relative to the 905 nm pump pulse. The delivery of laser radiation to the area of interest was performed either with microscope optics or using a 330-mm fiber with focusing tip.

The laser-induced photoacoustic waves were detected using 3.5 MHz ultrasound transducers having a diameter of 4.5 mm (model 6528101, Imasonic). The transducer was gently attached to the external surface of the sample containing the labeled cells or nanoparticles to be detected and warmed water or ultrasound gel was topically applied to the surface to enhance the acoustic matching between the transducer and the samples. The detected signal was amplified using a 2 MHz, 60 dB gain amplifier (model 5660B, Panametrics), and the amplified signal was digitized, recorded, and analyzed as described in Example 2.

Also shown in FIG. 32 is a magnet similar to the magnet described in Example 20 that was used to apply an external magnetic field to the area of interest. In selected experiments, a similar magnet was used that incorporated a custom-made 0.7-mm hole through which the 330-mm fiber was threaded to deliver the laser radiation. The magnet was gently attached to the surface of the sample containing the nanoparticles or labeled cells to be detected. In those cases in which the sample was a live mouse, the distances between the magnet and examined vessels ranged from 50 to 100 mm (mouse ear) or 0.3 to 0.5 mm (abdominal area).

Figure 33:
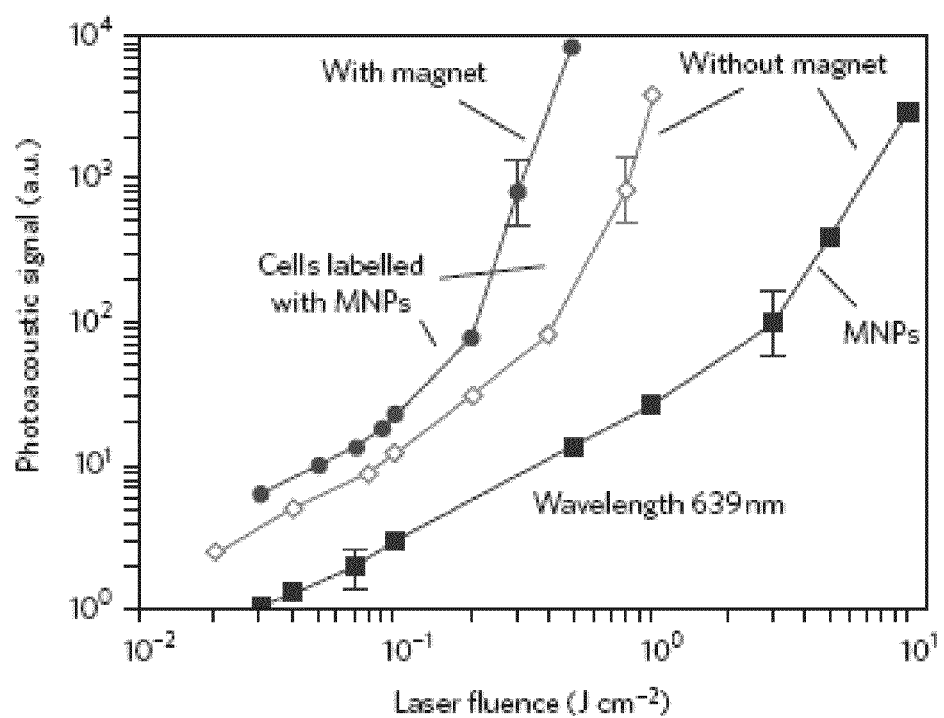
FIG. 33 is a summary of the PA signal rates produced by three different samples at a range of laser fluences: a suspension of magnetic nanoparticles, a suspension of cells labeled with magnetic nanoparticles, and a suspension of cells labeled with magnetic nanoparticles in an external magnetic field.

Samples containing suspensions of either $10^{11}$ MNPs/ml of 10-nm MNPs in PBS, or a single MDA-MB-231 cell labeled with the MNPs as described above were placed onto 120-mm-thick microscope slides. The PAFC system detected PA signals generated using laser fluences ranging from about $10^{-2}$ to about $10^1$ J/cm$^2$, either in the presence or absence of an external magnetic field that was applied for 10 minutes prior to PA detection. As shown in FIG. 33, the PA signals from the MNP-labeled cells were significantly higher than the PA signals from unbound MNPs, particularly at the higher laser fluences and after exposure to the magnetic field for 10 min. This signal amplification may be due to magnet-induced MNP clustering within the labeled cells and laser-induced microbubbles around the MNP clusters.

Figure 34:
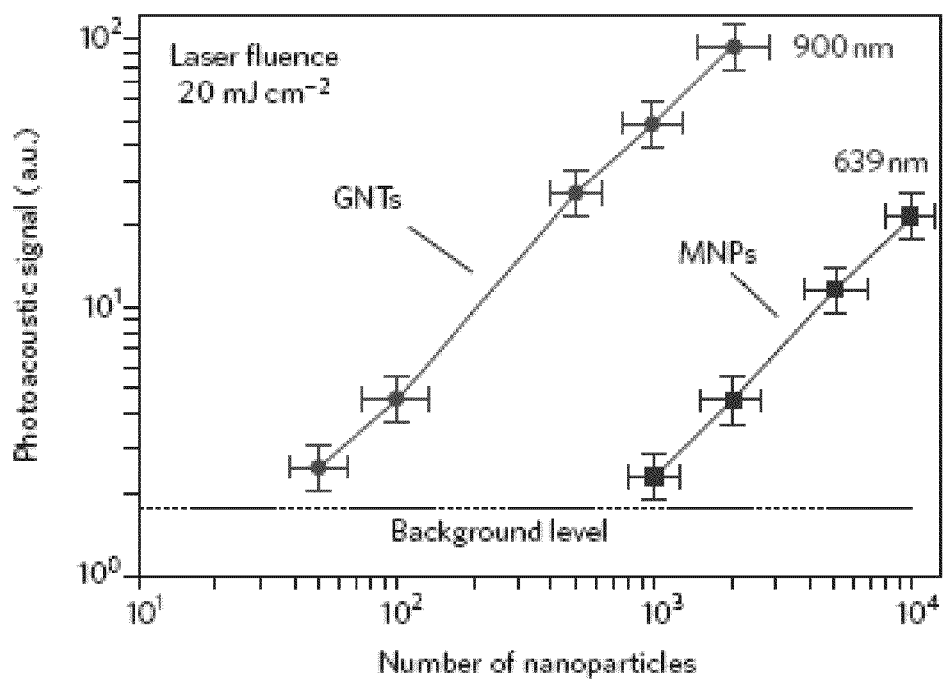
FIG. 34 is a summary of the PA signal rates from samples of gold nanotubes and magnetic nanoparticles spiked into mouse blood at a range of nanoparticle concentrations.

MNPs and GNPs were spiked into mouse blood samples at a range of concentrations and PA signals of the spiked samples were obtained using laser pulses at a laser fluence of 20 mJ/cm² and pulse wavelengths of 639 nm and 900 nm for the MNP and GNP samples, respectively. The photoacoustic signals measured for the two sample types are summarized in FIG. 34; the lowest detectable concentrations of nanoparticles above the background PA signals from other blood components were determined to be 35 GNTs and 720 MNPs.

Labeling efficiency of the MDA-MB-231 cells using different combinations of unconjugated and conjugated nanoparticles was assessed using the PAFC system on static cell cultures. The samples to be labeled included MDA-MB-231 cells suspended in PBS, MDA-MB-231 cells spiked into mouse blood, and unspiked mouse blood with no added MDA-MB-231 cells. The labeling particles added to the samples included: 1) unconjugated MNPs, 2) unconjugated GNTs, 3) a 20:80 ratio mixture of GNTs and MNPs, 4) conjugated MNP-ATF particles, 5) conjugated GNT-FOL particles, and 6) a 20:80 ratio mixture of GNT-FOL and MNP-ATF particles. The samples were treated with the labeling particles for one hour at 37° C. Table 3 summarizes the labeling efficiencies obtained using the PAFC system. The conjugated nanoparticle mixture cocktail showed the best targeting efficiency (96±2.1%) for the cells on mouse blood under static conditions.

TABLE 3

Labeling Efficiency of Unconjugated vs. Conjugated Nanoparticles

| Nanoparticles | Labeling Efficiency (%) | | |
|---|---|---|---|
| | Cells in PBS | Cells in Mouse Blood | Normal Mouse Blood (control) |
| MNP | 5 | 3 | 5 |
| GNT | 15 | 8 | 4 |
| MNP + GNT | 18 | 11 | 8 |
| MNP-ATF | 85 | 71 | 98 |
| GNT-FOL | 89 | 76 | 96 |
| MNP-AFT + GNT-FOL | 98 | 96 | 9 |

Figure 35:
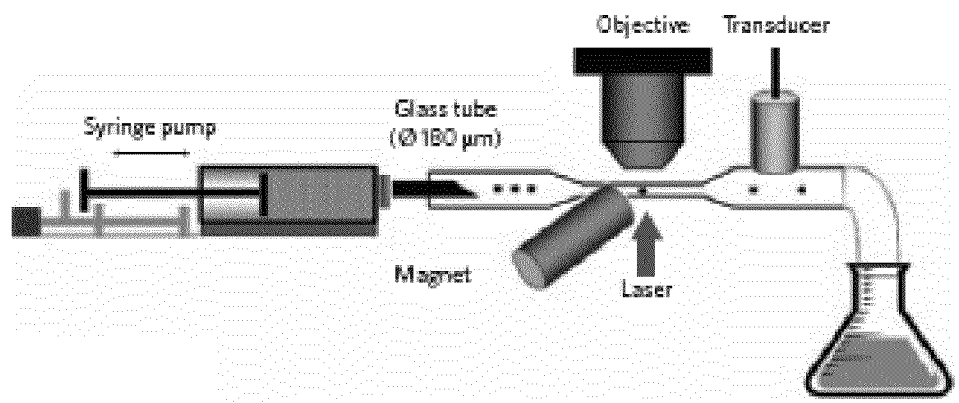
FIG. 35 is a schematic illustration of a PAFC flow simulation system.
Figure 36:
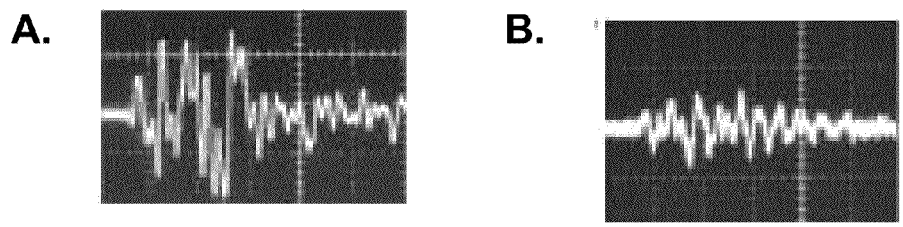
FIG. 36 includes non-linear photothermal (PT) signals obtained from labeled cancer cells (FIG. 36A) and from the surrounding suspension medium (FIG. 36B) using a PAFC flow simulation system.
Figure 37:
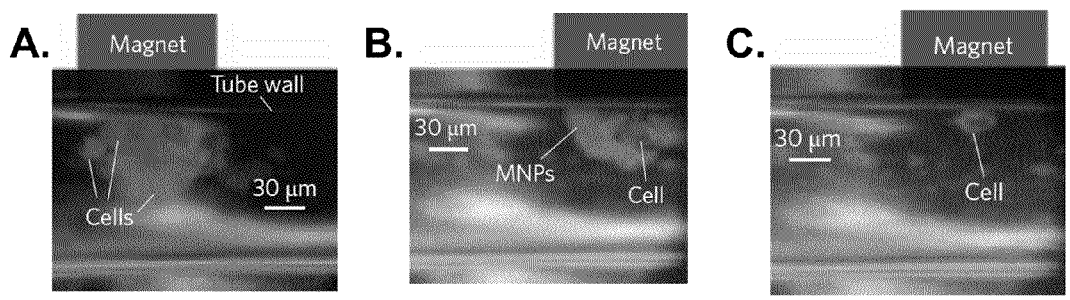
FIG. 37 includes fluorescent microscopic images of cancer cells labeled with conjugated magnetic nanoparticles in the vicinity of a magnet showing the labeled cancer cells suspended in PBS at a flow velocity of 0.5 cm/s (FIG. 37A), the labeled cancer cells with additional conjugated magnetic nanoparticles at flow velocities of 0.1 cm/s (FIG. 37B) and 5 cm/s (FIG. 37C).

To assess the ability to capture cancer cells labeled with MNP-AFT particles using a magnetic field, a PAFC flow simulation system, shown in FIG. 35 was used visualize the capture of the labeled cancer cells and to measure PA signals generated by labeled cancer cells at different flow velocities ranging from 0.1-10 cm/s. The PAFC flow simulation system included a syringe pump attached to a 180 μm diameter glass tube. The glass tube directed the flow of the sample exiting the syringe pump past a magnet and laser and into a flask. A microscope objective and an ultrasound transducer were also attached to the glass tube in close proximity to the magnet and laser to obtain microscopic images and PA signals, respectively. Labeled cancer cells were suspended in PBS either with or without additional MNP-AFT particles and observed as they flowed through the glass tube at a range of flow velocities. The PA signals produced by the labeled cancer cells and the surrounding suspension medium are shown in FIGS. 36A and 36B, respectively. FIG. 37 is a series of fluorescent microscopic images taken in the vicinity of the magnet of labeled cancer cells in PBS at a flow velocity of 0.5 cm/s (FIG. 37A), for labeled cancer cells with additional MNP-AFT particles at flow velocities of 0.1 cm/s (FIG. 37B) and 5 cm/s (FIG. 37C).

Figure 38:
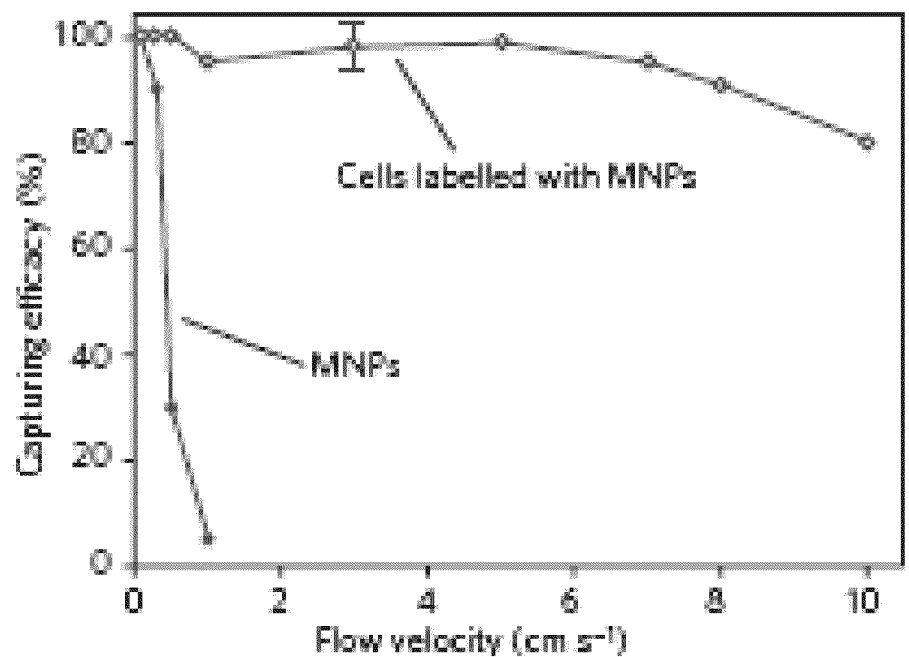
FIG. 38 is a summary of the capture efficiency (the number of cells or particles captured at a flow velocity as a percentage of the number of cells or particles captured at 0.1 cm/s.

The attached magnet of the PAFC flow simulation system captured the MNP-labeled cancer cells at a broad range of flow velocities (0.1-10 cm/s), accompanied by strong PA signals from the area under the magnet is excess of those signals outside the magnet corresponding to rare uncaptured cells and unbound MNPs. Both the additional MNPs and the MNP-labeled cells were captured at a flow velocity of 0.1 cm/s, as shown in FIG. 37B. However, increasing the flow velocity to 5 cm/s removed most of the free MNPs but the MNP-labeled cell remained captured, as shown in FIG. 37C. FIG. 38 summarizes the capture efficiency of the labeled cells and the MNPs, defined as the relative number of cells or MNPs captured at different flow velocities as a percentage of the corresponding number captured at a flow velocity of 0.1 cm/s. The capture efficiency of the unbound MNPs falls off rapidly as flow velocity increases above 0.1 cm/s, while the capture efficiency is maintained at a level of at least 90% for all but the highest flow velocities. Because magnetic force is proportional to the density of magnetic material within a particular volume, the randomly distributed free MNPs were more likely to be removed from the magnetic field by flow drag forces than the labeled cancer cells that contained a higher local MNP concentration or dense MNP clusters.

Figure 39:
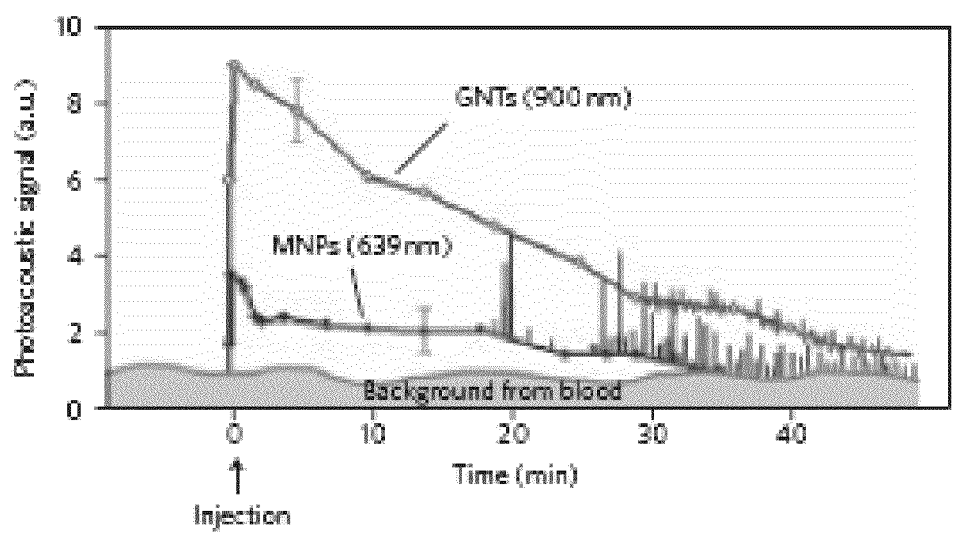
FIG. 39 is a summary of the PA signal rates produced by circulating gold nanotubes and magnetic nanoparticles in a mouse ear vein after an initial injection of the nanoparticles into the tail vein of the mouse.

To determine the depletion kinetics of the nanoparticles in vivo, MNPs and GNTs were separately injected through mouse tail vein of nude mice (nu/nu) and the circulation of the nanoparticles was monitored using the mouse ear model described in Example 2. The nanoparticles were injected in two separate samples consisting of MNPs in 10 mL of PBS at a concentration of $10^9$ nanoparticles/mL, and GNTs in 10 mL of PBS at a concentration of $10^{11}$ nanoparticles/mL. Photoacoustic monitoring of vessels in the mouse ear was conducted using laser pulses at 639 and 900 nm to detect concentration of the circulating nanoparticles. As summarized in FIG. 39, the half-life of both nanoparticles in circulation was about 15-20 minutes. At later times, rare flashes of PA signals appeared, preferentially from the MNPs, which were likely associated with random fluctuation of nanoparticle numbers in the detected volume and the non-specific uptake of the nanoparticles by circulating blood cells such as macrophages. No photoacoustic signals were detected from either nanoparticle at a concentration of less than $10^9$ nanoparticles/mL, suggesting that the PA signals from unbound or non-specifically bound nanoparticles fell below the background level from the blood.

Figure 40:
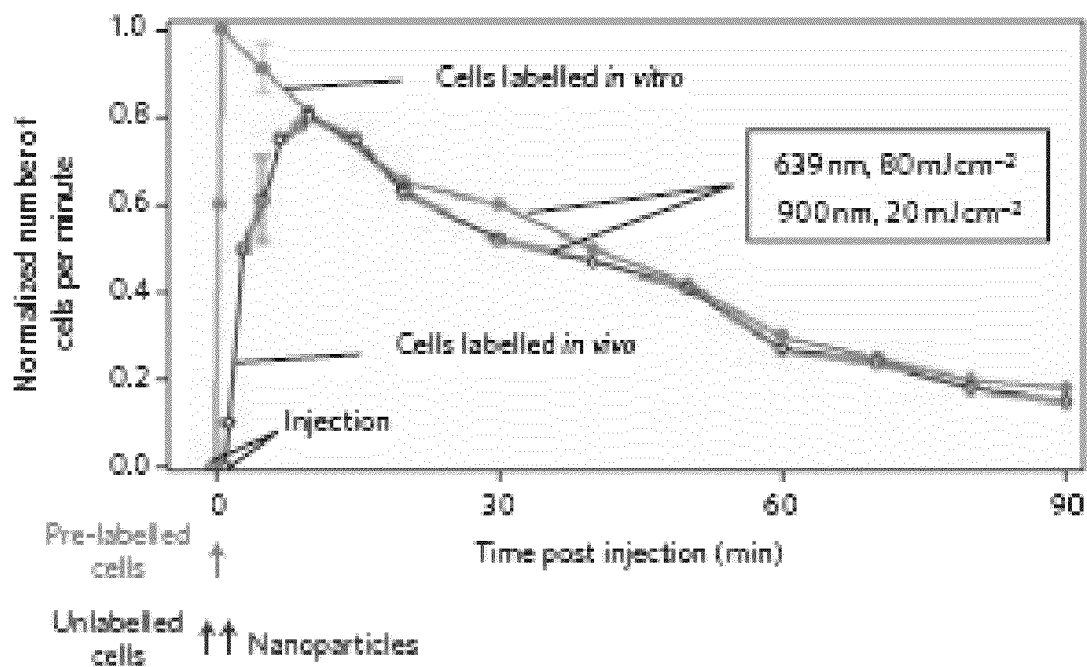
FIG. 40 is a summary of the PA signal rates produced by circulating cancer cells that were labeled with nanoparticles either in vitro or in vivo measured from a mouse abdominal vein an initial injection of the labeled cells (in vitro) or after an initial injection of unlabeled cancer cells followed by a separate injection of conjugated nanoparticles (in vivo) into the tail vein of the mouse.

The depletion kinetics of simulated circulating tumor cells (CTCs) that were labeled in vitro and in vivo were similarly assessed. The in vitro labeled cancer cells were cultured with a 20:80 ratio mixture of GNT-FOL and MNP-ATF particles and then injected into the tail vein of the nude mice. The in vivo labeled cancer cells were formed by first injecting unlabeled cancer cells into the tail vein of the nude mice, followed by an injection of 10 μL of PBS in which a 20:80 ratio mixture of GNT-FOL and MNP-ATF particles was suspended. The labeled cancer cells were monitored in an abdominal vessel of the mice using the PAFC with laser pulses of 639 nm and 900 nm transmitted to the vicinity of the abdominal vessel via laser fiber at laser fluences of 80 mJ/cm² and 20 mJ/cm² respectively. FIG. 40 summarizes the results of the PA detection of the in vitro and in vivo labeled CTCs.

After intravenous injection of $10^5$ cancer cells labeled with the nanoparticles in vitro, flashes of photoacoustic signals at both 639 and 900 nm with dominant amplitude at 900 nm were observed immediately after injection, corresponding to the detection of labeled CTCs. The frequency of detected PA signals subsequently declined and disappeared 60-90 minutes after the initial injection of the in vitro labeled CTCs. After the initial injection of the nanoparticles in the in vivo labeling case, photoacoustic signals at both 639 and 900 nm gradually increased in frequency within 8-10 min to approximately the same detection frequency observed from cells labeled in vitro. The subsequent decline in detection frequency of the in vivo labeled CTCs followed a similar pattern of decline as the clearance of the in vitro labeled CTCs. Infrequent PA signals associated with the 900 nm pulse only or the 639 nm pulse only were detected, which may be associated with the targeting of infrequently-occurring CTCs that express only one of the selected biomarkers targeted by the nanoparticle conjugates. The blood surrounding the circulating CTCs produced weak background signals with consistent and comparable amplitudes at both laser pulse wavelengths, and no PA signals with consistent amplitudes consistently above the background signal of the blood was detected other than the CTC detection signals, indicating a negligible background signal originating from unbound circulating nanoparticles.

The results of this experiment indicated that conjugated magnetic nanoparticles and gold nanotubes, particularly in combination, may be used to label circulating tumor cells with high specificity and efficiency, rendering the labeled CTCs amenable to in vivo detection using photoacoustic detection methods.

Example 22

Magnet-Induced Amplification and Visualization of Labeled CD44+ Circulating Tumor Cells targeted by MNPs To assess the in vivo detection of circulating tumor cells (CTCs) originating from a primary tumor using the in vivo photoacoustic flow cytometry (PAFC) methods described above in combination with cell labeling using conjugated nanoparticles and magnet-induced signal amplification, the following experiments were conducted.

Tumors were induced in nude mice (nu/nu) by inoculating breast cancer xenografts consisting of $5 \times 10^6$ MDA-MB-231 cells subcutaneously into the mice. At 2, 3, and 4 weeks after initial tumor development, a 20:80 ratio mixture of conjugated MNPs and CNTs (described previously in Example 21) was injected into the tail vein of the mice. After allowing 20 minutes for clearing the majority of unbound injected nanoparticles, photoacoustic detection of the labeled CTCs circulating in an abdominal vessel and in an ear vessel was performed using the PAFC device and methods described in Example 21. The results of these measurements are summarized in Table 4.

TABLE 4

Circulating Tumor Cells Detected After Inoculation of Nude Mice With Cancer Xenografts

| | Rate of CTCs Detected (cells/min) | | |
| --- | --- | --- | --- |
| Week | Ear Vessel | Abdominal Vessel | Ear:Abdominal CTC Ratio |
| 2 | 0.9 ± 0.3 | 6 ± 2.1 | 0.15 |
| 3 | 7.2 ± 0.3 | 26 ± 0.3 | 0.27 |
| 4 | 15.1 ± 2.7 | 47 ± 6.4 | 0.32 |

Figure 41:
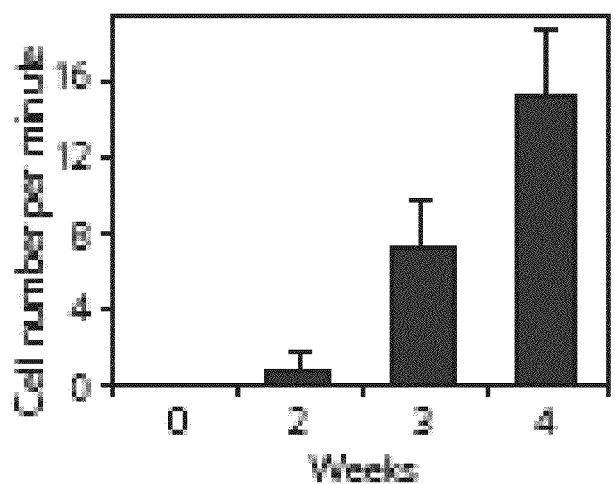
FIG. 41 is a summary of the PA signal rates from circulating tumor cells in a mouse abdominal vein measured at 2, 3, and 4 weeks of tumor development. The circulating tumor cells were labeled in vivo using conjugated magnetic nanoparticles and gold nanotubes.
Figure 42:
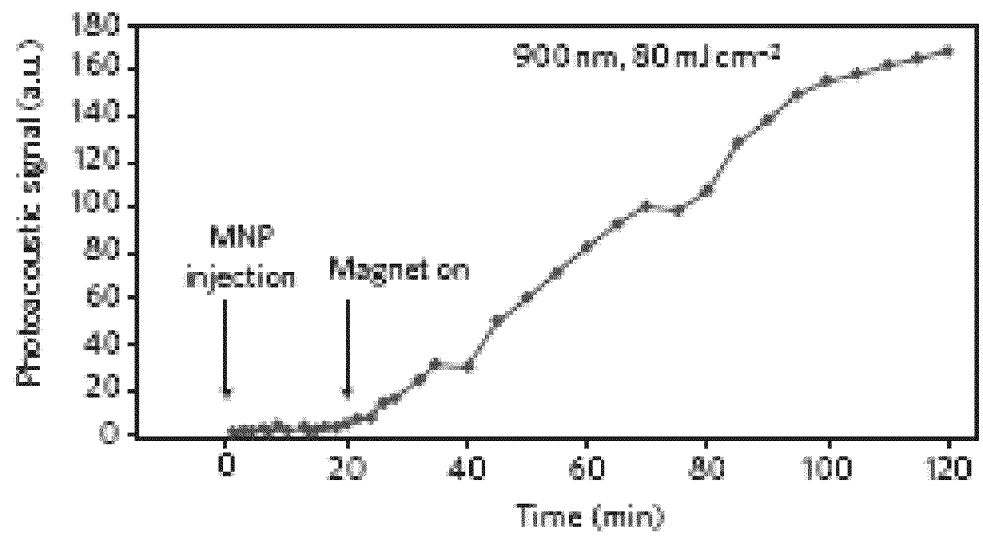
FIG. 42 is a summary of the PA signal rates from circulating tumor cells in an abdominal vein after one week of tumor development. The circulating tumor cells were labeled with magnetic nanoparticles in vivo and an external magnetic field was applied near the area of interest in the abdominal vein 20 minutes after initial injection of conjugated magnetic nanoparticles.
Figure 43:
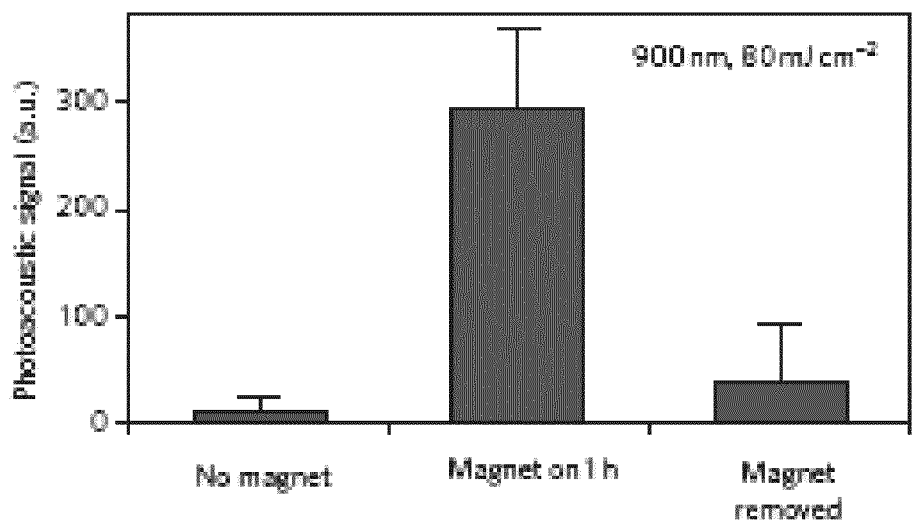
FIG. 43 is a summary of the PA signal rates from circulating tumor cells in an abdominal vein after two weeks of tumor development. The circulating tumor cells were labeled with magnetic nanoparticles in vivo. PA signals were measured before the application of a magnetic field, one hour after the initial application of an external magnetic field, and after the removal of the magnetic field.

As shown in Table 4, the ratio of the CTC detection rate in the mouse ear vessel to the CTC detection rate in the abdominal vessels increased from 2 weeks to 4 weeks. The CTC detection rate in the mouse ear vein, summarized in FIG. 41, was roughly correlated with the stage of the primary tumor progression and vessel sizes. Attaching a magnet similar to the magnet described in Example 21 in the vicinity of the abdominal blood vessel 20 min after the injection of conjugated nanoparticle into the mice at week 1 of tumor development changed the character of the photoacoustic signal from infrequent flashes of signals to a continuous increase of photoacoustic signals, as summarized in FIG. 42. Similar patterns were observed after 2 to 4 weeks of tumor development. As shown in FIG. 43, the signal amplitude in the abdominal vessels of mice at week 2 of tumor development increased 88-fold within one hour of the application of an external magnetic field. Removal of the magnet led to the release of the trapped CTCs bound to nanoparticles, resulting in a decrease in the PA signal amplitudes. This partial decrease in PA signal amplitude may be due to the remaining CTCs left adhered to the vessel wall.

The results of this experiment indicated that duplex molecular targeting of CTCs with functionalized nanoparticles followed by CTC capture and detection using dual magnetic-photoacoustic flow cytometry technology may be feasible for the detection of CTCs circulating in the bloodstream, in vivo, in real time.

Example 23

Magnetic Manipulation and Detection of Blood Cells Using an Extracorporeal Shunt To assess the efficacy of in vivo detection of circulating blood cells in an extracorporeal shunt using the in vivo photoacoustic flow cytometry (PAFC) methods described above, in combination with cell labeling using conjugated nanoparticles and magnet-induced signal amplification, the following experiments were conducted.

Figure 52:
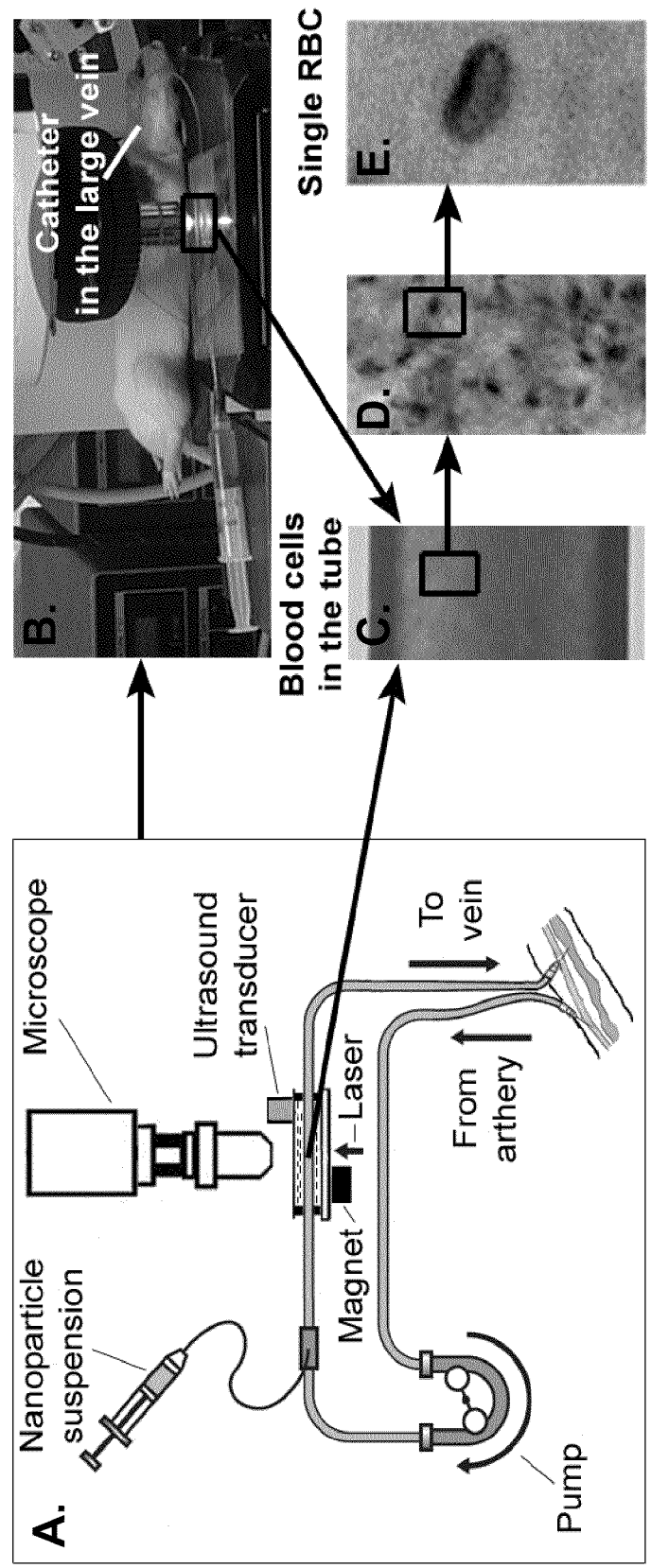
FIG. 52A is a diagram of an extracorporeal shunt.
FIG. 52B is a photograph of an extracorporeal shunt attached to a white rat.
FIG. 52C-FIG. 52E are microscope images of the blood flow through the extracorporeal shunt at magnifications of 4×, 20×, and 100×, respectively.

An extracorporeal shunt, illustrated in FIG. 52A, was used to label, magnetically manipulate, and detect circulating tumor cells from a white rat. Catheters were inserted into a large artery and a jugular vein of the rat as shown in FIG. 52B. Blood from the rat entered the extracorporeal shunt through the arterial catheter and exited the shunt through the jugular catheter. Functionalized magnetic 10-nm nanoparticles were injected into the shunt upstream of the detection point near the magnet and laser and ultrasound transducer. The distances between injection site and detection points may be varied by change of tube length in order to enhance the binding of the functionalized magnetic nanoparticles to the circulating tumor cells. The magnetically labeled in-flow tumor cells were captured by the magnetic field produced by the magnet. Laser irradiation of the detection area near the magnet generated photoacoustic signals which were detected with the ultrasound transducer attached to the tube. The photoacoustic amplitude signals were found to be correlated with concentration of the magnetically captured circulating tumor cells (not shown).

Conventional transmission imaging in the detection area provided information used to control the position of the laser beam, magnet, and ultrasound transducer. Using the high speed high resolution imaging mode of the optical system also provided visualization of individual moving cells at the single cell level, as shown in FIG. 53C-FIG. 53E for magnifications of 4×, 20× and 100×, respectively.

The results of this experiment demonstrated that the extracorporeal shunt provided photoacoustic continuous monitoring of shunted blood flow in an external tube, and the efficient capture of magnetically labeled abnormal circulating objects (e.g., tumor cells, bacteria, toxin, or drug) targeted by the magnetic nanoparticles within the extracorporeal flow. In addition, the magnetic capture of both magnetically-labeled abnormal objects and unbound magnetic nanoparticles prevented their further introduction into the systematic circulation of the rat.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

REFERENCES

1. Ara, G. Anderson, R. R., Mandel K. G., Ottesen, M, Oseroff, A. R., (1990), "Irradiation of pigmented melanoma cells with high intensity pulsed radiation generates acoustic waves and kills cells", Lasers Surg Med, 10, 52-59.
2. Kim, J. W., Kotagiri, N., Kim, J. H., and Deaton, R, (2006), "In situ fluorescence microscopy visualization and characterization of nanometer-scale carbon nanotubules labeled with 1-pyrenebutanoic acid, succinimdylester", Appl. Phys. Lett., 88, 213110.
3. D. O. Lapotko and V. P. Zharov (2005). "Spectral evaluation of laser-induced cell damage with photothermal microscopy", Laser Surg. Med. 36, 22-33.
4. H. Liao and J. H. Hafner (2005). "Gold nanorod bioconjugates", Chem. Mater. 17, 4636-4641.
5. Weight, R. M., Viator, J. A., Dale, P. S., Caldwell, C. W., Lisle, A. E. (2006), "Photoacoustic detection of metastatic melanoma cells in the human circulatory system", Opt Lett. 31, 2998-3000.
6. V. P. Zharov and D. O. Lapotko (2005). "Photothermal imaging of nanoparticles and cells (review)", IEEE J. Sel. Topics Quant. Electron. 11, 733-751
7. Zharov, V. P., Galanzha, E. I., Tuchin, V. V. (2006), "In vivo photothermal flow cytometry: imaging and detection of individual cells in blood and lymph flow", J Cell Biochem. 97, 916-932.

What is claimed is:

1. A device for the manipulation and detection of a magnetic target object within a moving biofluid of a living organism, comprising:
    an in vivo flow cytometer for detecting the magnetic target object within an area of interest; and
    at least one magnet for producing a magnetic field that manipulates the magnetic target object within the area of interest wherein the in vivo flow cytometer is an in vivo photoacoustic flow cytometer comprising a laser fiber for delivering at least one laser pulse to the area of interest, wherein the laser fiber comprises a focusing tip to transmit the at least one laser pulse to the area of interest; and
    wherein the at least one magnet comprises a magnetic material forming a channel, wherein the laser fiber passes through the channel and the focusing tip is situated at a laser pulse location that is essentially coincident to a corresponding magnetic field location.

2. The device of claim 1, wherein the manipulation of the magnetic target object is chosen from enrichment, capture, sorting, separation, concentration within a selected region of the biofluid, or any combination thereof of the target object within the area of interest.

3. The device of claim 1, wherein the at least one magnet is situated at a distance between about 0.1 mm and about 20 cm from the area of interest.

4. The device of claim 1, wherein the device detects the magnetic target object at a detection sensitivity ranging from about 1 to about 100 target objects per L of the moving biofluid.

5. The device of claim 1, wherein the at least one magnet produces a field that captures the magnetic target object within the area of interest.

6. The device of claim 1, wherein the moving biofluid is chosen from blood, lymph, cerebrospinal fluid, urine, chyme, cytosol, tears, or interstitial fluid.

7. The device of claim 1, wherein the magnetic target object is chosen from an intrinsically magnetic target object or a target object labeled with a magnetic particle.

8. The device of claim 7, wherein the magnetic particle is chosen from a magnetic nanoparticle or a magnetic microparticle having a size ranging from about 5 nm to about 10 μm.

9. The device of claim 1, wherein the magnetic target object is labeled with a contrast agent selected from an ultrasound contrast agent, a photoacoustic contrast agent, a hybrid contrast agent, a fluorescent contrast agent, a Raman contrast agent, an MRI contrast agent, a superconductivity quantum interference device contrast agent, a PET contrast agent, and a CT contrast agent.

10. The device of claim 9, wherein the hybrid contrast agent is a nanoparticle complex or a microparticle complex chosen from a gold-magnetic complex, a quantum dot-magnetic complex, a carbon nanotube-magnetic complex, a radionucleotide-magnetic complex, a surface enhanced resonance scattering-magnetic complex, or any combination thereof.

11. The device of claim 1, wherein the magnetic field has a strength ranging from about 0.1 T to about 20 T.

12. The device of claim 11, wherein the magnetic field is chosen from a permanent field and a pulsed field.

13. The device of claim 1, wherein the at least one magnet comprises two or more magnets situated along a direction of movement of the moving biofluid.

14. The device of claim 13, further comprising a securing cuff including the two or more magnets.

15. The device of claim 1, wherein at least one magnet is configured to be in contact with the external integument of the living organism.

16. The device of claim 15, further comprising a magnetic cuff including the at least one magnet.

17. The device of claim 1, wherein the at least one magnet is configured to be invasively situated in the vicinity of the moving biofluid.

18. The device of claim 17, further comprising an invasive insertion device chosen from a needle or a catheter, wherein the invasive insertion device includes the at least one magnet.

19. The device of claim 1, further comprising an extracorporeal shunt including a circulatory bypass tube for continuously withdrawing the moving biofluid out of the living organism, directing the moving biofluid through the circulatory bypass tube, and returning the moving biofluid back into the organism, wherein the area of interest includes a cross-section of the circulatory bypass tube.

20. A method of manipulating and detecting magnetic target objects within a moving biofluid of a living organism, comprising:
    situating at least one magnet to manipulate the magnetic target objects within a magnetic field produced by the at least one magnet in an area of interest; and
    detecting the magnetic target objects using an in vivo flow cytometer wherein the in vivo flow cytometer is an in vivo photoacoustic flow cytometer comprising a laser fiber for delivering at least one laser pulse to the area of interest, wherein the laser fiber comprises a focusing tip to transmit the at least one laser pulse to the area of interest; and wherein the at least one magnet comprises a magnetic material forming a channel, wherein the laser fiber passes through the channel and the focusing tip is situated at a laser pulse location that is essentially coincident to a corresponding magnetic field location.

21. The method of claim 20, wherein the manipulation of the magnetic target objects is chosen from enrichment, capture, sorting, separation, concentration within a selected region of the biofluid, or any combination thereof of the target objects within the area of interest.

22. The method of claim 20, wherein the at least one magnet is situated at a distance between about 0.1 mm and about 20 cm from the area of interest.

23. The method of claim 20, wherein the device detects the magnetic target objects at a detection sensitivity ranging from about 1 to about 100 target objects per L of the moving biofluid.

24. The method of claim 20, wherein the at least one magnet produces a field that captures the magnetic target objects within the area of interest.

25. The method of claim 20, wherein the moving biofluid is chosen from blood, lymph, cerebrospinal fluid, urine, chyme, cytosol, tears, or interstitial fluid.

26. The method of claim 20, wherein the magnetic target objects are chosen from intrinsically magnetic target objects or target objects labeled with magnetic particles.

27. The method of claim 26, further comprising labeling target objects with magnetic particles to obtain the target objects labeled with magnetic particles.

28. The method of claim 27, wherein the target objects are additionally labeled with contrast agents chosen from ultrasound contrast agents, photoacoustic contrast agents, hybrid contrast agents, fluorescent contrast agents, Raman contrast agents, MRI contrast agents, superconductivity quantum interference device contrast agents, PET contrast agents, or CT contrast agents.

29. The method of claim 28, wherein the hybrid contrast agents are nanoparticle complexes or a microparticle complexes chosen from gold-magnetic complexes, quantum dot-magnetic complexes, carbon nanotube-magnetic complexes, radionucleotide-magnetic complexes, surface enhanced resonance scattering-magnetic complexes, or any combination thereof.

30. The method of claim 28, wherein the contrast agents used to additionally label the target objects are conjugated with second targeting moieties chosen from antibodies, ligands, antigens, or cell marker proteins, wherein the second targeting moieties are different from the first targeting moieties.

31. The method of claim 30, further comprising injecting the conjugated contrast agent into the moving biofluid prior to situating the at least one magnet.

32. The method of claim 26, wherein the magnetic particles are chosen from magnetic nanoparticles or magnetic microparticles having a size ranging from about 5 nm to about 10 μm.

33. The method of claim 26, wherein the magnetic particles used to label the target objects comprise magnetic nanoparticles conjugated with first targeting moieties chosen from antibodies, ligands, antigens, or cell marker proteins.

34. The method of claim 33, further comprising injecting the magnetic particles conjugated with targeting moieties into the moving biofluid prior to situating the at least one magnet.

35. The method of claim 26, wherein the target objects are labeled with magnetic particles and the target objects are chosen from biomarkers, drugs, toxins, microparticles, nanoparticles, viruses, or cells.

36. The method of claim 35, wherein the biomarkers are chosen from proteins, antibodies, hormones, single-stranded DNA fragments, double-stranded DNA fragments, or RNA fragments.

37. The method of claim 35, wherein the cells are chosen from pathogenic bacteria, pathogenic fungi, pathogenic protists, or cancer cells.

38. The method of claim 37, wherein the cancer cells are metastatic cancer stem cells resulting from a cancer chosen from melanoma, leukemia, brain cancer, breast cancer, colon cancer, prostate cancer, ovarian cancer, pancreatic cancer, or testicular cancer.

39. The method of claim 20, wherein the moving biofluid flows through a circulatory vessel chosen from a blood vessel, a lymphatic vessel, an extracorporeal shunt, or any combination thereof.

40. The method of claim 39, wherein the at least one magnet is invasively situated in the vicinity of the circulatory vessel.

41. The method of claim 40, wherein the at least one magnet is incorporated into an invasive insertion device chosen from a needle device or a catheter device.

42. The method of claim 20, further comprising subjecting the detected magnetic target objects to an additional process chosen from removal for biochemical or genetic analysis; non-invasive eradication using high-energy pulses chosen from laser pulses, microwave pulses, or ultrasound pulses; magnetic purging; mechanical removal; needle extraction; or any combination thereof.

43. A method of detecting the presence of target cells within a biofluid of a living organism moving through a circulatory vessel, comprising:
    injecting magnetic nanoparticles conjugated with first targeting moieties into the circulatory vessel to produce magnetic target cells comprising the magnetic particles attached to the target cells;
    injecting photoacoustic contrast agents conjugated with second targeting moieties different than the first targeting moieties into the circulatory vessel producing magnetic target cells labeled with the photoacoustic contrast agents;
    situating at least one magnet to manipulate the magnetic target cells within a magnetic field produced in an area of interest by the at least one magnet;
    detecting the magnetic target cells in the area of interest using an in vivo photoacoustic flow cytometer; and,
    subjecting the magnetic target cells to an additional process chosen from removal for biochemical or genetic analysis; non-invasive eradication using high-energy pulses chosen from laser pulses, microwave pulses, or ultrasound pulses; magnetic purging; mechanical removal; needle extraction; or any combination thereof.

44. The method of claim 43, wherein the manipulation of the magnetic target cells is chosen from enrichment, capture, sorting, separation, concentration within a selected region of the biofluid, or any combination thereof of the magnetic target cells within the area of interest.

45. The method of claim 43, wherein the at least one magnet produces a field that captures the magnetic target cells within the circulatory vessel.

46. The method of claim 43, wherein the at least one magnet is situated at a distance ranging from about 0.1 mm to about 20 cm from the area of interest.

47. The method of claim 43, wherein the first targeting moieties and the second targeting moieties are chosen from antibodies, ligands, antigens, or cell marker proteins.

48. The method of claim 43, wherein the moving biofluid is chosen from blood, lymph, cerebrospinal fluid, urine, chyme, cytosol, tears, or interstitial fluid.

49. The method of claim 43, wherein the target cells are chosen from abnormal cells chosen from sickle cells, inflamed cells, or cancer cells; pathogenic bacteria; pathogenic fungal cells; or pathogenic protists.

50. The method of claim 49, wherein the cancer cells are metastatic cancer stem cells resulting from a cancer chosen from melanoma, leukemia, brain cancer, breast cancer, colon cancer, prostate cancer, ovarian cancer, pancreatic cancer, or testicular cancer.

* * * * *